TO

US009428465B2

(12) United States Patent
Piomelli et al.

(10) Patent No.: US 9,428,465 B2
(45) Date of Patent: Aug. 30, 2016

(54) ACID CERAMIDASE INHIBITORS AND THEIR USE AS MEDICAMENTS

(71) Applicants: FONDAZIONE ISTITUTO ITALIANO DI TECHNOLOGIA, Genoa (IT); THE REGENTS OF THE UNIVERSITY OF CALIFORNIA, Oakland, CA (US); UNIVERSITA'DEGLI STUDI DI PARMA, Parma (IT)

(72) Inventors: Daniele Piomelli, Irvine, CA (US); Natalia Realini, Valmorea (IT); Marco Mor, Ghedi (IT); Chiara Pagliuca, Arezzo (IT); Daniela Pizzirani, Genoa (IT); Rita Scarpelli, Rome (IT); Tiziano Bandiera, Gambolo (IT)

(73) Assignee: Fondazione Istituto Italiano Di Technologia, Genoa (IT)

( * ) Notice: Subject to any disclaimer, the term of this patent is extended or adjusted under 35 U.S.C. 154(b) by 0 days.

(21) Appl. No.: 14/404,226

(22) PCT Filed: May 27, 2013

(86) PCT No.: PCT/EP2013/060846
§ 371 (c)(1),
(2) Date: Nov. 26, 2014

(87) PCT Pub. No.: WO2013/178576
PCT Pub. Date: Dec. 5, 2013

(65) Prior Publication Data
US 2015/0111892 A1      Apr. 23, 2015

(30) Foreign Application Priority Data

May 28, 2012   (IT) .............. MI2012A0921

(51) Int. Cl.
*A61K 31/515* (2006.01)
*C07D 239/54* (2006.01)
*C07D 239/545* (2006.01)
*C07D 239/553* (2006.01)
*C07D 239/557* (2006.01)
*A61K 31/513* (2006.01)
*A61K 31/5377* (2006.01)
*A61K 45/06* (2006.01)
*A61N 5/10* (2006.01)
*C07D 239/60* (2006.01)
*C07D 401/04* (2006.01)
*C07D 403/04* (2006.01)

(52) U.S. Cl.
CPC ......... *C07D 239/54* (2013.01); *A61K 31/513* (2013.01); *A61K 31/5377* (2013.01); *A61K 45/06* (2013.01); *A61N 5/10* (2013.01); *C07D 239/545* (2013.01); *C07D 239/553* (2013.01); *C07D 239/557* (2013.01); *C07D 239/60* (2013.01); *C07D 401/04* (2013.01); *C07D 403/04* (2013.01); *A61N 2005/1098* (2013.01)

(58) Field of Classification Search
CPC ............ C07D 239/54; C07D 239/545; C07D 239/553; C07D 239/557; C07D 239/60; C07D 401/04; C07D 403/04; A61K 31/513; A61K 31/5377; A61K 45/06; A61N 5/10; A61N 2005/1098
See application file for complete search history.

(56) References Cited

FOREIGN PATENT DOCUMENTS

| EP | 0186452 A2 * | 7/1986 | ............ C07F 7/0818 |
|---|---|---|---|
| GB | 968666 | 9/1964 | |
| GB | 2016921 | 10/1979 | |
| JP | 53130679 A * | 11/1978 | |
| JP | S55-136267 | 10/1980 | |
| JP | 2001064179 | 3/2001 | |
| WO | 2010054223 | 5/2010 | |
| WO | 2010078247 | 7/2010 | |

OTHER PUBLICATIONS

Cas Registry No. 1348517-90-7 (Dec. 4, 2011).*
CAS Abstract JP 53130679 (May 12, 1984).*
D. Sawada et al., 47 Tetrahedron Letters, 7219-7223 (2006).*
C. Arnal-Herault et al., 13 Chemistry—A European Journal, 6792-6800 (2007).*
Registry file [online], Jul. 3, 2001, RN:344408-74-8.
International Search Report dated Aug. 27, 2013 corresponding to International PCT Application No. PCT/EP2013/060846; 2 pages.
Written Opinion dated Aug. 27, 2013 corresponding to International PCT Application No. PCT/EP2013/060846; 6 pages.
International Preliminary Report on Patentability dated Jul. 14, 2014 corresponding to International PCT Application No. PCT/EP2013/060846; 26 pages.
Hedayatullah, et al. "Synthese De Nouvelles Structures D'interet Biologique Renfermant Un Bloc Adamantane Par Monoalkylation Et Monocarbamoylation L'uracile, De La Thymine Et Du 5-Fluorouracile" Mar. 31, 1995; 1 page.
Bedia et al.; "Cytotoxicity and acid ceramidase inhibiroty activity of 2-substituted aminoethanol amides"; Chemistry and Physics of Lipids, 156, 2008, pp. 33-40.
Biswal et al.; "Changes in ceramide and sphingomyelin following fludarabine treatment of human chronic B-cell leukemia cells"; Toxicology, 154, 2000, pp. 45-53.
Bose et al.; "Ceramide Synthase Mediates Daunorubicin-Induced Apoptosis: An Alternative Mechanism for Generating Death Signals"; Cell, vol. 82, Aug. 11, 1995; pp. 405-414.
Chalfant et al.; "Mechanisms of Signal Transduction: De Novo Ceramide Regulates the Alternative Splicing of Caspase 9 and Bcl-x in A549 Lung Adenocarcinoma Cells: Dependent on Protein Phosphatase-1"; The Journal of Biological Chemistry; 2002, 277:12587-12595.

(Continued)

*Primary Examiner* — Alexander R Pagano
(74) *Attorney, Agent, or Firm* — Ohlandt, Greeley, Ruggiero & Perle, LLP

(57) ABSTRACT

The present invention concerns, in a first aspect, compounds of Formula I as defined herein, pharmaceutically acceptable salts thereof and pharmaceutical compositions containing such compounds. The present invention also relates to compounds of Formula I for use as acid ceramidase inhibitors, and in the treatment of cancer and other disorders in which modulation of the levels of ceramide is clinically relevant.

5 Claims, 3 Drawing Sheets

(56) References Cited

OTHER PUBLICATIONS

Chauvier et al.; "Ceramide involvement in homocamptothecin- and camptothecin-induced cytotoxicity andapoptosis in colon HT29 cells"; Int. J. Oncol.; Apr. 2002; 20(4):855-63; http://www.spandidos-publications.com/ijo/20/4/855.

Elojeimy et al; "Role of Acid Ceramidase in Resistance to FasL: Therapeutic Approaches Based on Acid Ceramidase Inhibitors and FasL Gene Therapy", The American Society of Gene Therapy; Molecular Therapy, Jul. 2007; vol. 15 No. 7; pp. 1259-1263.

Gangoiti et al.; "Control of metabolism and signaling of simple bioactive sphingolipids: Implications in disease"; Progress in Lipid Research, 49, 2010, pp. 316-334.

Hannun et al.; "Principles of bioactive lipid signalling: lessons from sphingolipids"; Nature Reviews, Molecular Cell Biology, vol. 9, Feb. 2008, pp. 139-150.

Holman et al.; "Lysosomotropic acid ceramidase inhibitor induces apoptosis in prostate cancer cells"; Cancer Chemother Pharmacol, 2008, 61:231-242.

Mahdy et al.; "Acid Ceramidase Upregulation in Prostate Cancer Cells Confers Resistance to Radiation: AC Inhibition, a Potential Radiosensitizer"; The American Society of Gene Therapy; vol. 17 No. 3, Mar. 2009; pp. 430-438.

Mao et al.; "Ceramidases: regulators of cellular responses mediated by ceramide, sphingosine, and sphingosine-1-phosphate"; Biochimica et Biophysica Acta; 1781, 2008, pp. 424-434.

Musumarra et al.; "A bioinformatic approach to the identification of candidate genes for the development of new cancer diagnostics"; Biol Chem., Feb. 2003, 384(2):321-7; http://www.degruyter.com/view/j/bchm.2003.384.issue-2/bc.2003.037/bc.2003.037.xml;jsessionid=24C967FCE986893A14C6603FE5119FF1.

Norris et al.; "Combined therapeutic use of AdGFPFasL and small molecule inhibitors of ceramide metabolism in prostate and head and neck cancers: a status report"; Cancer Gene Therapy, 2006, 13, pp. 1045-1051.

Ogretmen et al.; "Biologically active sphingolipids in cancer pathogensis and treatment"; Nature Reviews Cancer; 4, Aug. 2004; pp. 604-616; http://www.nature.com/nrc/journal/v4/n8/full/nrc1411.html.

Seelan et al.; "Human Acid Ceramidase Is Overexpressed But Not Mutated in Prostate Cancer"; Genes, Chromosomes & Cancer, 2000, 29:137-146.

Selzner et al.; "Induction of Apoptotic Cell Death and Prevention of Tumor Growth by Ceramide Analogues in Metastatic Human Colon Cancer"; Cancer Research, 61, Feb. 1, 2001, pp. 1233-1240.

Wymann et al.; "Lipid signalling in disease"; Nature Publishing Group; Feb. 2008, vol. 9, pp. 162-176.

Callahan B P et al. "A Raman-active competitive inhibitor of OMP decarboxylase", Bioorganic Chemistry, vol. 34, No. 2, Apr. 1, 2006, pp. 59-65, XP024896888.

* cited by examiner

ACID CERAMIDASE INHIBITORS AND THEIR USE AS MEDICAMENTS

STATEMENT AS TO RIGHTS TO INVENTIONS MADE UNDER FEDERALLY SPONSORED RESEARCH OR DEVELOPMENT

This research was made, in part, with government support under NIH Grant R01 DA12413 awarded by the National Institutes of Health; the United States Government has certain rights in the invention.

CROSS-REFERENCES TO RELATED APPLICATIONS

Not applicable.

FIELD OF INVENTION

The present invention relates to acid ceramidase inhibitors and their use as medicaments.

In particular, the present invention concerns acid ceramidase inhibitors, pharmaceutical compositions containing them and methods for preparing these inhibitors.

The present invention also provides methods of inhibiting acid ceramidase for the treatment of cancer and other disorders in which modulation of the levels of ceramide is clinically relevant.

BACKGROUND OF THE INVENTION

The sphingolipids are a family of membrane lipids derived from the aliphatic amino alcohol sphingosine and its related sphingoid bases. They are present in eukaryote membranes, where they exert important structural roles in the regulation of fluidity and subdomain structure of the lipid bilayer. In addition to that, they have emerged as key effectors in many aspects of cell biology including inflammation, cell proliferation and migration, senescence and apoptosis [see, for instance, Hannun Y A, Obeid L M. *Principles of bioactive lipid signalling: lessons from sphingolipids. Nat. Rev. Mol. Cell Biol.* 2008, 9, 139-150].

Ceramide is considered a central molecule in sphingolipid catabolism. The generic term "ceramide" comprises a family of several distinct molecular species deriving from the N-acylation of sphingosine with fatty acids of different chain length, typically from 14 to 26 carbon atoms. Ceramide can be synthesized de novo from condensation of serine with palmitate, catalyzed by serine palmitoyltransferase, to form 3-keto-dihydrosphingosine. In turn, 3-keto-dihydrosphingosine is reduced to dihydrosphingosine, followed by acylation by a (dihydro)-ceramide synthase. Ceramide is formed by the desaturation of dihydroceramide. Alternatively, ceramide can be obtained by hydrolysis of sphingomyelin by sphingomyelinases. Ceramide is metabolized by ceramidases to yield sphingosine and fatty acid [Hannun Y A, Obeid L M, *Nat. Rev. Mol. Cell Biol.* 2008, 9, 139-150].

Ceramide plays an important role in a variety of cellular processes. Ceramide concentrations increase in response to cellular stress, such as DNA damage, exposure to cancer chemotherapeutic agents and ionizing radiation, and increased ceramide levels can trigger senescence and apoptosis in normal cells, [Wymann M P, Schneiter R. *Lipid signalling in disease. Nat. Rev. Mol. Cell. Biol.* 2008, 9, 162-176]. Moreover, ceramide is also involved in the regulation of cancer cell growth, differentiation, senescence and apoptosis [Ogretmen B and Hannun Y A. *Biologically active sphingolipids in cancer pathogenesis and treatment. Nat Rev. Cancer* 2004, 4, 604-616]. Many anticancer drugs increase ceramide levels in cells by stimulating its de novo synthesis and/or hydrolysis of sphingomyelin. For example, daunorubicin elicits ceramide production through the de novo pathway [Bose R et al., *Ceramide synthase mediates daunorubicin-induced apoptosis; an alternative mechanism for generating death signals. Cell* 1995, 82, 405-414]. De novo ceramide induction was observed in various human cancer cells after treatment with camptothecin and fludarabine [Chauvier D et al. *Ceramide involvement in homo-camptothecin-and camptothecin induced cytotoxicity and apoptosis in colon HT29 cells. Int. J. Oncol.* 2002, 20, 855-863; Biswal S S et al., *Changes in ceramide and sphingomyelin following fludarabine treatment of human chroni chronic B-cell leukemia cells. Toxicology* 2000, 154, 45-52], and with gemcitabine [Chalfant C E et al., *De novo ceramide regulates the alternative splicing of caspase 9 and Bcl-x in A549 lung adenocarcinoma cells. Dependence on protein phosphatase-1. J. Biol. Chem.* 2002, 277, 12587-12595]. In many of these studies, inhibition of de novo ceramide synthesis was found to prevent, at least in part, the cytotoxic responses to these agents, thus indicating that the de novo pathway might function as a common mediator of cell death. Therefore, increasing or sustaining the levels of ceramide in cancer cells could be envisaged as a novel therapeutic strategy to induce cell death.

An approach to increasing or sustaining the levels of ceramide in cells consists in the inhibition of enzymes responsible for ceramide clearance. Enzymes that contribute to decreasing the intracellular levels of ceramide are glucosylceramide synthase, which incorporates ceramide into glucosylceramide, sphingomyelin synthase, which synthesizes sphingomyelin, and ceramidases, which hydrolyze ceramide to sphingosine and fatty acid. Currently, there are five known human ceramidases; acid ceramidase, neutral ceramidase, alkaline ceramidase 1, alkaline ceramidase 2, and alkaline ceramidase 3 [Mao C, Obeid L M. *Ceramidases: regulators of cellular responses mediated by ceramide, sphingosine, and sphingosine-1-phosphate. Biochim. Biophys. Acta* 2008, 1781, 424-434]. Among them, acid ceramidase is emerging as an important enzyme in the progression of cancer and in the response to tumor therapy [Gangoiti P at al., *Control of metabolism and signaling of simple bioactive sphingolipids: Implications in disease. Prog. Lipid Res.* 2010, 49, 316-34]. Messenger RNA and protein levels of acid ceramidase are heightened in a wide variety of cancers including prostate cancer [Seelan R S et al., *Human acid ceramidase is overexpressed but not mutated in prostate cancer, Genes Chromosomes Cancer* 2000, 29, 137-146], head and neck cancer [Norris J S et al., *Combined therapeutic use of AdGFPFasL and small molecule inhibitors of ceramide metabolism in prostate and head and neck cancers: a status report. Cancer Gene Ther* 2006, 13, 1045-1051; Elojeimy S et al., *Role of acid ceramidase in resistance to FasL: therapeutic approaches based on acid ceramidase inhibitors and FasL gene therapy. Mol. Ther.* 2007, 15, 1259-1263], and melanoma [Musumarra G et al., *A bioinformatic approach to the identification of candidate genes for the development of new cancer diagnostics. Biol. Chem.* 2003, 384, 321-327]. In prostate cancer, acid ceramidase expression correlates with the malignant stage of the disease [Seelan R S et al., *Human acid ceramidase is overexpressed but not mutated in prostate cancer. Genes Chromosomes Cancer* 2000, 29, 137-146]. Up-regulation of acid ceramidase has also been observed in prostate cancer cells in response to radiotherapy, and this mechanism desensitizes cells to both chemotherapy and radiotherapy. Restoration of acid ceramidase levels in radio-resistant cells by either gene silencing or inhibition of acid ceramidase activity confers radiation sensitivity to prostate cancer cells. Improvement of tumor sensitivity to ionizing radiation by inhibition of acid ceramidase has been shown in vivo in a PPC-1 xenograft model [Mandy A E at al., *Acid ceramidase upregulation in prostate cancer cells confers resistance to radiation: AC inhibition, a potential radiosensitizer. Mol. Ther.* 2009, 17, 430-438]. Together, these data suggest that acid ceramidase provides a growth advantage to cancer cells and contributes to the altered balance between proliferation and death eventually leading to tumor progression. Therefore, inhibition of acid ceramidase appears to be a promising strategy for cancer treatment.

Certain methods for inhibiting ceramidase activity by compound containing a sphingoid base, a derivative of a sphingoid base, or a salt of a sphingoid base are described in the European patent application EP1287815. Other methods for inhibiting ceramidase activity using cyclopropenyl-sphingosine derivatives are described in the patent application WO2005/051891. Still other methods for inhibiting ceramidase activity in cells using cationic ceramide derivatives are reported in the patent application WO2006/050264. Further methods for inhibiting or modulating add ceramidase activity are disclosed in the patent application WO2007/136635 and in the patent application WO2010/054223.

Acid ceramidase inhibitors disclosed in the scientific and patent literature, such as B13 [Selzner M et al., *Induction of apoptotic cell death and prevention of tumor growth by ceramide analogues in metastatic human colon cancer. Cancer Res.* 2001, 61, 1233-1240], LCL 204 [Holman D H et al., *Lysosomotropic acid ceramidase inhibitor induces apoptosis in prostate cancer cells. Cancer Chemother. Pharmacol.* 2008, 61, 231-242,] or E-tb [Bedia C et al., *Cytotoxicity and acid ceramidase inhibitory activity of 2-substituted aminoethanol amides. Chem. Phys. Lipids* 2008, 156, 33-40], are ceramide analogs that inhibit acid ceramidase activity in cell-free assays and proliferation of cancer cell lines only at high micromolar concentrations.

There is therefore still a substantial need for novel acid ceramidase inhibitors with improved potency and drug-likeness. Accordingly, one of the aims of the present invention resides in the provision of novel acid ceramidase inhibitors for use in the prevention or treatment of disorders or diseases in which the modulation of the levels of ceramide is clinically relevant.

SUMMARY OF THE INVENTION

The inventors have discovered that specific compounds bearing a uracil moiety inhibit acid ceramidase and are useful in the treatment of cancer.

In a first aspect, the present invention provides a compound of Formula I or pharmaceutically acceptable salts thereof

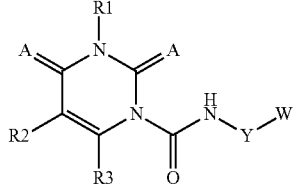

Formula I wherein:

A represents O or S;

Y represents a bond, an optionally substituted alkyl, an optionally substituted alkenyl, an optionally substituted alkynyl, an optionally substituted cycloalkyl, an optionally substituted heterocyclyl, or a group —$(CR_aR_b)_n$-Q-$(CR_cR_d)_m$—;

W represents hydrogen, an optionally substituted aryl, an optionally substituted heteroaryl, an optionally substituted heterocyclyl, an optionally substituted cycloalkyl, a group —$(CR_eR_f)_p$—$CR_gR_hR_i$ or a group Z—$R_4$;

$R_1$ represents hydrogen, an optionally substituted alkyl, an optionally substituted alkenyl, an optionally substituted cycloalkyl, an optionally substituted aryl, an optionally substituted heteroaryl, an optionally substituted heterocyclyl, or a group C(=O)$R_5$;

$R_2$ represents hydrogen, chlorine, bromine, iodine, an optionally substituted lower alkyl, an optionally substituted heterocyclyl, an optionally substituted aryl, an optionally substituted heteroaryl, or a group selected from —CN, O—$R_6$, S—$R_6$, or N$R_7R_8$;

$R_3$ represents hydrogen, halogen, or an optionally substituted alkyl;

Q represents O, S, N$R_9$, C(=O);

Z represents O, S, N$R_9$;

$R_4$ represents hydrogen, an optionally substituted alkyl, an optionally substituted cycloalkyl, an optionally substituted aryl, an optionally substituted heteroaryl, an optionally substituted heterocyclyl;

$R_5$ represents hydrogen, an optionally substituted lower alkyl, an optionally substituted cycloalkyl, an optionally substituted aryl, an optionally substituted heteroaryl, an optionally substituted heterocyclyl, or a group selected from O—$R_{10}$ or S—$R_{10}$;

$R_6$ represents hydrogen, an optionally substituted alkyl, an optionally substituted cycloalkyl, an optionally substituted heterocyclyl;

$R_7$ and $R_8$ independently represent hydrogen, an optionally substituted lower alkyl, an optionally substituted cycloalkyl an optionally substituted aryl, an optionally substituted heteroaryl, an optionally substituted heterocyclyl, a group (C=O)$R_5$, or when taken together with the nitrogen atom to which they are bound they represent an optionally substituted heterocyclyl;

$R_9$ represents hydrogen, an optionally substituted alkyl, an optionally substituted cycloalkyl, an optionally substituted aryl, an optionally substituted heterocyclyl;

$R_{10}$ represents an optionally substituted alkyl, an optionally substituted cycloalkyl, an optionally substituted aryl, an optionally substituted heteroaryl, or an optionally substituted heterocyclyl;

$R_a$, $R_b$, $R_c$, $R_d$, $R_e$, $R_f$, $R_g$, $R_h$, and $R_i$ are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;

m is an integer from 0 to 12;

p is an integer from 0 to 6;

or a pharmaceutically acceptable salt thereof, with the proviso that:

when A represents oxygen, $R_1$, $R_2$ and $R_3$ represent hydrogen, then the group Y—W does not represent methyl, n-propyl, n-hexyl, n-dodecyl, n-hexadecyl, cyclohexyl or phenyl;

when A represents oxygen, $R_1$ represents methyl, $R_2$ and $R_3$ represent hydrogen, then the group Y—W does not represent n-hexyl;

when A represents oxygen, $R_1$ represents hydrogen, $R_2$ represents methyl and $R_3$ represents hydrogen, then the group Y—W does not represent methyl, n-hexyl, 2-propen-1-yl, cyclohexyl, phenyl, or a lysine or ornithine residue;

when A represents oxygen, $R_1$ represents hydrogen, $R_2$ represents fluoromethyl and $R_3$ represents hydrogen, then the group Y—W does not represent n-hexyl;

when A represents oxygen, $R_1$ represents hydrogen, $R_2$ represents bromine, and $R_3$ represents hydrogen, then the group Y—W does not represent methyl;

when A represents oxygen, $R_1$ represents i-propyl, $R_2$ represents bromine, and $R_3$ represents methyl, then the group Y—W does not represent phenyl;

when A represents oxygen, $R_1$ represents hydrogen, $R_2$ represents iodine, and $R_3$ represents hydrogen, then the group Y—W does not represent phenyl.

In certain preferred embodiments compounds of Formula I are provided wherein A is O.

In a second aspect the invention concerns a compound of Formula I as a medicament, in particular it concerns compounds of Formula I for use in the treatment of pathologies where modulation or inhibition of acid ceramidase is needed, such as in the treatment of cancer and other disorders where modulation of ceramide levels is clinically relevant.

In a third aspect the invention concerns pharmaceutical compositions comprising a compound of Formula I and a pharmaceutically acceptable carrier and/or excipient. In a fourth aspect, the present invention provides a method for modulating the levels of ceramides in a subject by administering a compound of Formula I or a pharmaceutical composition containing such compound.

In some embodiments, the present invention provides methods for treating conditions associated with reduced levels of ceramides, including various cancers and hyperproliferative diseases, by administering a therapeutically effective amount of a compound of Formula I.

In a fifth aspect, the present invention provides methods for preparing compounds of Formula I, as defined above, through a process consisting of suitable synthetic transformations.

Concentration-response curve of prolonged (72 hrs) treatment with compound 4 (A) or compound 5 (B) on SW403 cell viability as measured by trypan blue assay. (C-D) Isobolographic analysis of data obtained after prolonged treatment of SW403 cells with compound 4 or compound 5 and 5FU. Isobolograms were constructed with median effective dose ($ED_{50}$) data measured by trypan blue assay. (E-F) Isobolographic analysis of data obtained after prolonged treatment of SW403 cells with compound 4 or compound 5 and taxol. Isobolograms were constructed with $ED_{50}$ data measured by trypan blue assay.

Figure 3:
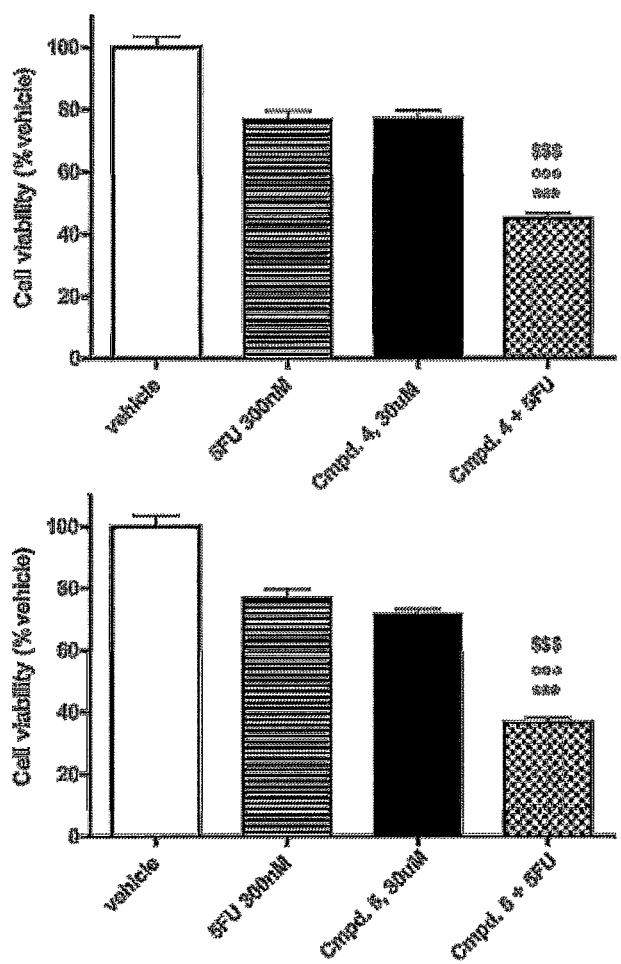

FIG. 3 shows bar graphs illustrating the effect of compound 4 and compound 5 on SW403 cell viability, and synergism with 5FU (MTT assay). Sub-chronic treatment (72 hrs) of SW403 cells with 5FU (300 nM), compound 4 (30 μM, upper panel), and compound 5 (30 μM, lower panel) reduced cell viability as measured by the MTT assay. Compounds 4 and 5 showed a synergistic effect with 5FU in reducing cell viability.

DETAILED DESCRIPTION OF THE INVENTION

The present invention origins from the finding that compounds represented by Formula I inhibit or modulate acid ceramidase activity. Therefore, such compounds can be used advantageously for the treatment of diseases associated with reduced levels of ceramide in an organ or body compartment.

I. COMPOUNDS OF FORMULA I

Thus, in accordance with the first aspect of the present invention, a compound of Formula I or pharmaceutically salts thereof are provided

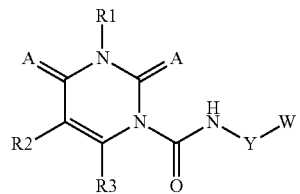

Formula I wherein:

A represents O or S;

Y, if present, represents an optionally substituted alkyl, an optionally substituted alkenyl, an optionally substituted alkynyl, an optionally substituted cycloalkyl, an optionally substituted heterocyclyl, or a group —$(CR_aR_b)_n$-Q-$(CR_cR_d)_m$—;

W represents hydrogen, an optionally substituted aryl, an optionally substituted heteroaryl, an optionally substituted heterocyclyl, an optionally substituted cycloalkyl, a group —$(CR_eR_f)_p$—$CR_gR_hR_i$ or a group Z—$R_4$;

$R_1$ represents hydrogen, an optionally substituted alkyl, an optionally substituted alkenyl, an optionally substituted cycloalkyl, an optionally substituted aryl, an optionally substituted heteroaryl, an optionally substituted heterocyclyl, or a group C(=O)$R_5$;

$R_2$ represents hydrogen, chlorine, bromine, iodine, an optionally substituted lower alkyl, an optionally substituted heterocyclyl, an optionally substituted aryl, an optionally substituted heteroaryl, or a group selected from —CN, O—$R_6$, S—$R_6$, or N$R_7R_8$;

$R_3$ represents hydrogen, halogen, or an optionally substituted alkyl;

Q represents O, S, N$R_9$, C(=O);

Z represents O, S, N$R_9$;

$R_4$ represents hydrogen, an optionally substituted alkyl, an optionally substituted cycloalkyl, an optionally substituted aryl, an optionally substituted heteroaryl, an optionally substituted heterocyclyl;

$R_5$ represents hydrogen, an optionally substituted lower alkyl, an optionally substituted cycloalkyl, an optionally substituted aryl, an optionally substituted heteroaryl, an optionally substituted heterocyclyl, or a group selected from O—$R_{10}$ or S—$R_{10}$;

$R_6$ represents hydrogen, an optionally substituted alkyl, an optionally substituted cycloalkyl, an optionally substituted heterocyclyl;

$R_7$ and $R_8$ independently represent hydrogen, an optionally substituted lower alkyl, an optionally substituted cycloalkyl an optionally substituted aryl, an optionally substituted heteroaryl, an optionally substituted heterocyclyl, a group (C=O)$R_6$, or when taken together with the nitrogen atom to which they are bound they represent an optionally substituted heterocyclyl;

$R_9$ represents hydrogen, an optionally substituted alkyl, an optionally substituted cycloalkyl, an optionally substituted aryl, an optionally substituted heterocyclyl;

$R_{10}$ represents an optionally substituted alkyl, an, optionally substituted cycloalkyl, an optionally substituted aryl, an optionally substituted heteroaryl, or an optionally substituted heterocyclyl;

Ra, Rb, Rc, Rd, Re, Rf, Rg, Rh, and Ri are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy;

n is an integer from 1 to 12;
m is an integer from 0 to 12;
p is an integer from 0 to 6;

or a pharmaceutically acceptable salt thereof, with the proviso that:

when A represents oxygen, $R_1$, $R_2$ and $R_3$ represent hydrogen, then the group Y—W does not represent methyl, n-propyl, n-hexyl, n-dodecyl, n-hexadecyl, cyclohexyl or phenyl;

when A represents oxygen, $R_1$ represents methyl, $R_2$ and $R_3$ represent hydrogen, then the group Y—W does not represent n-hexyl;

when A represents oxygen, $R_1$ represents hydrogen, $R_2$ represents methyl and $R_3$ represents hydrogen, then the group Y—W does not represent methyl, n-hexyl, 2-propen-1-yl, cyclohexyl, phenyl, or a lysine or ornithine residue;

when A represents oxygen, $R_1$ represents hydrogen, $R_2$ represents fluoromethyl and $R_3$ represents hydrogen, then the group Y—W does not represent n-hexyl;

when A represents oxygen, $R_1$ represents hydrogen, $R_2$ represents bromine, and $R_3$ represents hydrogen, then the group Y—W does not represent methyl;

when A represents oxygen, $R_1$ represents i-propyl, $R_2$ represents bromine, and $R_3$ represents methyl, then the group Y—W does not represent phenyl;

when A represents oxygen, $R_1$ represents hydrogen, $R_2$ represents iodine, and $R_3$ represents hydrogen, then the group Y—W does not represent phenyl.

Compounds of Formula I containing a carbon-carbon double bond can exist as E and Z geometric isomers. Geometric isomers of compounds of Formula I containing one or more carbon-carbon double bonds are within the scope of the present invention.

Compounds of Formula I may contain one or more chiral centers. Compounds containing one chiral, center can occur as single enantiomers or mixtures of the two enantiomers. Such mixtures occur as racemates or racemic mixtures. Compounds containing more than one chiral center can occur as single enantiomers and pairs of enantiomers, and as stereoisomers which are not enantiomers, referred to as diastereoisomers. Compounds of Formula I are meant to encompass all possible stereoisomers and mixtures thereof.

Some of the compounds described herein may exist with different points of attachment of a hydrogen atom, referred to as tautomers. Such an example may be a ketone and its enol form known as keto-enol tautomers. The individual tautomers as well as mixture thereof are encompassed by the Formula I.

The compounds of Formula I may have unnatural ratios of atomic isotopes at one or more of their atoms. For example, the compounds may be radiolabeled with isotopes such as tritium or carbon-14. All isotopic variations of the compounds of the present invention, whether radioactive or not, are within the scope of the present invention.

Compounds of Formula I may be isolated in the form of their pharmaceutically acceptable acid addition salts, such as the salts derived from inorganic and organic acids. The term "pharmaceutically acceptable salts" refers to salts prepared from pharmaceutically acceptable, non-toxic acids including inorganic or organic acids. Such acids include hydrochloric, sulfuric, phosphoric, glycolic, malic, maleic, tartaric, succinic, citric, malonic acid and the like.

The present invention also encompasses active metabolites of compounds of Formula I.

In certain embodiments compounds of Formula I as defined above are provided wherein:

A represents O or S;

Y, if present, represents an optionally substituted alkyl, an optionally substituted cycloalkyl, an optionally substituted heterocyclyl, or a group —$(CR_aR_b)_n$-Q-$(CR_cR_d)_m$;

W represents hydrogen, an optionally substituted aryl, an optionally substituted heteroaryl, an optionally substituted cycloalkyl a group —$(CR_eR_f)_p$—$CR_gR_hR_i$ or a group Z—$R_4$;

$R_1$ represents hydrogen, an optionally substituted alkyl, an optionally substituted alkenyl, an optionally substituted cycloalkyl, an optionally substituted heterocyclyl, or a group C(=O)$R_5$;

$R_2$ represents hydrogen, chlorine, bromine, iodine, an optionally substituted lower alkyl, an optionally substituted heterocyclyl, an optionally substituted aryl, or a group selected from O—$R_6$ or $NR_7R_8$;

$R_3$ represents hydrogen, halogen, or an optionally substituted alkyl;

Q represents O, $NR_9$, C(=O);

Z represents O, $NR_9$;

$R_4$ represents hydrogen, an optionally substituted alkyl, an optionally substituted cycloalkyl, an optionally substituted aryl, an optionally substituted heteroaryl, an optionally substituted heterocyclyl;

$R_5$ represents an optionally substituted lower alkyl, an optionally substituted cycloalkyl, an optionally substituted aryl, an optionally substituted heteroaryl, an optionally substituted heterocyclyl, or a group O—$R_{10}$;

$R_6$ represents hydrogen, an optionally substituted alkyl, an optionally substituted cycloalkyl, an optionally substituted heterocyclyl;

$R_7$ and $R_8$ independently represent hydrogen, an optionally substituted lower alkyl, an optionally substituted cycloalkyl, an optionally substituted aryl, an optionally substituted heteroaryl, an optionally substituted heterocyclyl, a group (C=O)$R_5$, or when taken together with the nitrogen atom to which they are bound they represent an optionally substituted heterocyclyl;

$R_9$ represents hydrogen, an optionally substituted alkyl, an optionally substituted cycloalkyl, an optionally substituted aryl;

$R_{10}$ represents an optionally substituted alkyl, an optionally substituted cycloalkyl, an optionally substituted aryl, an optionally substituted heteroaryl, or an optionally substituted heterocyclyl;

$R_a$, $R_b$, $R_c$, $R_d$, $R_e$, $R_f$, $R_g$, $R_h$, and $R_i$ are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;
m is an integer from 0 to 12;
p is an integer from 0 to 6;

or a pharmaceutically acceptable salt thereof.

In these embodiments certain compounds of Formula I are provided wherein A is O.

According to some embodiments, compounds of Formula I are provided wherein:

A represents O;

Y, if present, represents an optionally substituted alkyl, an optionally substituted cycloalkyl, an optionally substituted heterocyclyl, or a group —$(CR_aR_b)_n$-Q-$(CR_cR_d)_m$—;

W represents hydrogen, an optionally substituted aryl, an optionally substituted heteroaryl, an optionally substituted cycloalkyl, a group —$(CR_eR_f)_p$—$CR_gR_hR_i$ or a group Z—$R_4$;

$R_1$ represents hydrogen, an optionally substituted alkyl, an optionally substituted alkenyl, an optionally substituted cycloalkyl, an optionally substituted heterocyclyl, or a group C(=O)$R_5$;

$R_2$ represents hydrogen, chlorine, bromine, iodine, an optionally substituted lower alkyl, an optionally substituted heterocyclyl, an optionally substituted aryl, or a group selected from O—$R_6$ or $NR_7R_8$;

$R_3$ represents hydrogen or halogen;

Q represents O, $NR_9$;

Z represents O, $NR_9$, $R_4$ represents hydrogen, an optionally substituted alkyl, an optionally substituted cycloalkyl, an optionally substituted aryl, an optionally substituted heteroaryl, an optionally substituted heterocyclyl;

$R_5$ represents an optionally substituted lower alkyl, an optionally substituted cycloalkyl, an optionally substituted aryl, an optionally substituted heteroaryl, an optionally substituted heterocyclyl, or a group O—$R_{10}$;

$R_6$ represents hydrogen, an optionally substituted alkyl, an optionally substituted cycloalkyl, an optionally substituted heterocyclyl;

$R_7$ and $R_8$ independently represent hydrogen, an optionally substituted lower alkyl, an optionally substituted cycloalkyl, an optionally substituted aryl, an optionally substituted heteroaryl, a group (C=O)$R_5$, or when taken together with the nitrogen atom to which they are bound they represent an optionally substituted heterocyclyl;

$R_9$ represents hydrogen, an optionally substituted alkyl, an optionally substituted cycloalkyl, an optionally substituted aryl;

$R_{10}$ represents an optionally substituted alkyl, an optionally substituted cycloalkyl, an optionally substituted aryl, an optionally substituted heteroaryl, or an optionally substituted heterocyclyl;

$R_a$, $R_b$, $R_c$, $R_d$, $R_e$, $R_f$, $R_g$, $R_h$, and $R_i$ are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;
m is an integer from 0 to 12;
p is an integer from 0 to 6.

In certain embodiments a suitable aryl group is selected from phenyl, alpha- or beta-naphthyl, indanyl, and biphenyl.

In accordance with certain embodiments compounds of Formula I are provided wherein:

A represents O;

Y, if present, represents an optionally substituted alkyl, an optionally substituted cycloalkyl or a group —$(CR_aR_b)_n$-Q-$(CR_cR_d)_m$—;

W represents hydrogen, an optionally substituted aryl, an optionally substituted heteroaryl, an optionally substituted cycloalkyl, a group —$(CR_eR_f)_p$—$CR_gR_hR_i$ or a group Z—$R_4$;

$R_1$ represents hydrogen, an optionally substituted alkyl, an optionally substituted cycloalkyl, an optionally substituted heterocyclyl, or a group C(=O)$R_5$;

$R_2$ represents hydrogen, chlorine, bromine, iodine, an optionally substituted lower alkyl, an optionally substituted heterocyclyl, an optionally substituted aryl, or a group selected from O—$R_6$ or $NR_7R_8$;

$R_3$ represents hydrogen;

Q represents O, $NR_9$;

Z represents O, $NR_9$;

$R_4$ represents hydrogen, an optionally substituted alkyl, an optionally substituted cycloalkyl, an optionally substituted aryl, an optionally substituted heteroaryl, an optionally substituted heterocyclyl;

$R_5$ represents an optionally substituted lower alkyl, an optionally substituted cycloalkyl, an optionally substituted aryl, an optionally substituted heteroaryl, or a group O—$R_{10}$;

$R_6$ represents hydrogen, an optionally substituted alkyl or an optionally substituted cycloalkyl;

$R_7$ and $R_8$ independently represent hydrogen an optionally substituted lower alkyl, an optionally substituted cycloalkyl, an optionally substituted aryl, an optionally substituted heteroaryl, a group (C=O)$R_5$;

$R_9$ represents hydrogen, an optionally substituted alkyl, an optionally substituted cycloalkyl, an optionally substituted aryl;

$R_{10}$ represents an optionally substituted alkyl, an optionally substituted cycloalkyl, an optionally substituted aryl, an optionally substituted heteroaryl, or an optionally substituted heterocyclyl;

$R_a$, $R_b$, $R_c$, $R_d$, $R_e$, $R_f$, $R_g$, $R_h$, and $R_i$ are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;
m is an integer from 0 to 12;
p is an integer from 0 to 6.

In certain embodiments of this first aspect of the invention compounds of Formula I are selected from the group comprising:

2,4-dioxo-N-(4-phenylbutyl)-pyrimidine-1-carboxamide
N-(2,2-diphenylethyl)-2,4-dioxo-pyrimidine-1-carboxamide
5-chloro-N-hexyl-2,4-dioxo-pyrimidine-1-carboxamide
N-hexyl-2,4-dioxo-5-(trifluoromethyl)pyrimidine-1-carboxamide
5-bromo-N-hexyl-2,4-dioxo-pyrimidine-1-carboxamide
N-hexyl-5-(hydroxymethyl)-2,4-dioxo-pyrimidine-1-carboxamide
N-hexyl-5-morpholino-2,4-dioxo-pyrimidine-1-carboxamide
5-[benzyl(methyl)amino]-N-hexyl-2,4-dioxo-pyrimidine-1-carboxamide
N-hexyl-5-methylamino-2,4-dioxo-pyrimidine-1-carboxamide
N-hexyl-5-(4-methylpiperazin-1-yl)-2,4-dioxo-pyrimidine-1-carboxamide
N-hexyl-2,4-dioxo-5-phenyl-pyrimidine-1-carboxamide
5-[benzoyl(methyl)amino]-N-hexyl-2,4-dioxo-pyrimidine-1-carboxamide
N-hexyl-5-iodo-2,4-dioxo-pyrimidine-1-carboxamide
N-hexyl-5-methoxy-2,4-dioxo-pyrimidine-1-carboxamide
3-(cyclopropylmethyl)-N-hexyl-5-methyl-2,4-dioxo-pyrimidine-1-carboxamide
3-buten-3-yl-N-hexyl-5-methyl-2,4-dioxo-pyrimidine-1-carboxamide
5-cyano-N-hexyl-2,4-dioxo-pyrimidine-1-carboxamide
N-hexyl-5,6-dimethyl-2,4-dioxo-pyrimidine-1-carboxamide
5-(4-fluorophenyl)-N-hexyl-2,4-dioxo-pyrimidine-1-carboxamide
N-hexyl-5-(4-methoxyphenyl)-2,4-dioxo-pyrimidine-1-carboxamide
N-hexyl-2,4-dioxo-5-(p-tolyl)pyrimidine-1-carboxamide
N-hexyl-2,4-dioxo-5-[4-(trifluoromethyl)phenyl]pyrimidine-1-carboxamide
N-hexyl-5-(2-naphthyl)-2,4-dioxo-pyrimidine-1-carboxamide
Methyl 5-bromo-3-(hexylcarbamoyl)-2,6-dioxo-pyrimidine-1-carboxylate
Isobutyl 5-bromo-3-(hexylcarbamoyl)-2,6-dioxo-pyrimidine-1-carboxylate
5-Bromo-N-hexyl-3-methyl-2,4-dioxo-pyrimidine-1-carboxamide
Isobutyl 3-(hexylcarbamoyl)-2,6-dioxo-5-phenyl-pyrimidine-1-carboxylate
N-Hexyl-3-methyl-2,4-dioxo-5-phenyl-pyrimidine-1-carboxamide
N-hexyl-5-(hydroxymethyl)-3-methyl-2,4-dioxo-pyrimidine-1-carboxamide
Isobutyl 3-(hexylcarbamoyl)-5-(hydroxymethyl)-2,6-dioxo-pyrimidine-1-carboxylate
Isobutyl 5-chloro-3-(hexylcarbamoyl)-2,6-dioxo-pyrimidine-1-carboxylate
N-hexyl-2,4-dioxo-5-(3-pyridyl)pyrimidine-1-carboxamide
N-octyl-2,4-dioxo-5-(trifluoromethyl)pyrimidine-1-carboxamide
2,4-dioxo-N-(5-phenylpentyl)pyrimidine-1-carboxamide
N-[5-(4-fluorophenyl)pentyl]-2,4-dioxo-pyrimidine-1-carboxamide
N-[(4-butylphenyl)methyl]-2,4-dioxo-pyrimidine-1-carboxamide
N-[(4-propylcyclohexyl)methyl]-2,4-dioxo-pyrimidine-1-carboxamide
N-hexyl-5-(2-methylpyrazol-3-yl)-2,4-dioxo-pyrimidine-1-carboxamide
N-hexyl-5-(2-methoxyphenyl)-2,4-dioxo-pyrimidine-1-carboxamide In other embodiments of this first aspect of the invention compounds of Formula I are selected from the group comprising:

N-(4-cyclohexylbutyl)-2,4-dioxo-pyrimidine-1-carboxamide
N-hexyl-2,4-dioxo-5-(2-pyridyl)pyrimidine-1-carboxamide
N-hexyl-2,4-dioxo-5-[2-(trifluoromethyl)phenyl]pyrimidine-1-carboxamide
5-(2-cyclohexylethyl)-N-hexyl-2,4-dioxo-pyrimidine-1-carboxamide
N-hexyl-2,4-dioxo-5-phenethyl-pyrimidine-1-carboxamide
N-hexyl-2,4-dioxo-5-(4-pyridyl)pyrimidine-1-carboxamide
5-chloro-N-hexyl-3-(methoxymethyl)-2,4-dioxo-pyrimidine-1-carboxamide
N-(1-methylhexyl)-2,4-dioxo-pyrimidine-1-carboxamide
N-hexyl-2,4-dioxo-5-(1-piperidyl)pyrimidine-1-carboxamide

II. SUBSET OF COMPOUNDS OF FORMULA IA

The inventors have also found that specific uracil derivatives where the 5 and 6 positions of the uracil are unsubstituted, and the 1-carboxamide moiety bears an alkyl chain ending with a lipophilic group, show an effective therapeutical activity, specifically an anticancer activity.

In accordance with certain embodiments of the invention, a subset of compounds of Formula Ia wherein A is O is provided.

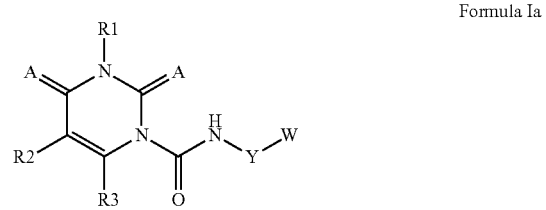

Formula Ia and wherein
$R_1$ represents hydrogen, an optionally substituted alkyl, an optionally substituted alkenyl, an optionally substituted cycloalkyl, an optionally substituted heterocyclyl, or a group $C(=O)R_5$;
$R_2$ and $R_3$ represent hydrogen;
Y, if represent, represents an optionally substituted alkyl, an optionally substituted cycloalkyl or a group $-(CR_aR_b)_n$-Q-$(CR_cR_d)_m-$;
W represents hydrogen, an optionally substituted aryl, an optionally substituted heteroaryl, an optionally substituted cycloalkyl, a group $-(CR_eR_f)_p-CR_gR_hR_i$ or a group $Z-R_4$;
Q represents O, $NR_9$;
Z represents O, $NR_9$;
$R_4$ represents hydrogen, an optionally substituted alkyl, an optionally substituted cycloalkyl, an optionally substituted aryl, an optionally substituted heteroaryl, an optionally substituted heterocyclyl;
$R_5$ represents an optionally substituted lower alkyl, an optionally substituted cycloalkyl, an optionally substituted aryl, an optionally substituted heteroaryl, or a group $O-R_{10}$;

$R_9$ represents hydrogen, an optionally substituted alkyl, an optionally substituted cycloalkyl, an optionally substituted aryl;

$R_{10}$ represents an optionally substituted alkyl, an optionally substituted cycloalkyl, an optionally substituted aryl, an optionally substituted heteroaryl, or an optionally substituted heterocyclyl;

$R_a$, $R_b$, $R_c$, $R_d$, $R_e$, $R_f$, $R_g$, $R_h$, and $R_i$ are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;

m is an integer from 0 to 12;

p is an integer from 0 to 6;

with the proviso that when W represents hydrogen, Y represents a group —$(CR_aR_b)_n$-Q-$(CR_cR_d)_m$—.

In certain embodiments $R_1$ is C(=O)$R_5$.

In certain embodiments of the compound of Formula Ia, A represents O.

In certain embodiments of the compounds of Formula Ia,

A represents O, $R_1$ represents hydrogen, an optionally substituted C1-C6 alkyl, an optionally substituted cycloalkyl selected from cyclopropane, cyclobutane, cyclopentane, or cyclohexane, an optionally substituted heterocyclyl selected from oxetane, tetrahydrofuran or tetrahydropyran, or a group C(=O)$R_5$, wherein $R_5$ is an optionally substituted C1-C6 alkyl, an optionally substituted cycloalkyl selected from cyclopropane, cyclobutane, cyclopentane, or cyclohexane, an optionally substituted aryl selected from phenyl or biphenyl, an optionally substituted heteroaryl selected from thiophene, oxazole, thiazole, oxadiazole, imidazole, pyrazole, pyridine, pyridazine, pyrimidine, and pyrazine, or a group O—$R_{10}$;

R2 and R3 represent hydrogen;

Y represents an optionally substituted alkyl, preferably a $C_1$-$C_8$ alkyl, or a group —$(CR_aR_b)_n$-Q-$(CR_cR_d)_m$—;

W represents an optionally substituted aryl selected from phenyl or, biphenyl, an optionally substituted heteroaryl selected from thiophene, thiazole, oxadiazole, pyrazole, pyridine pyridazine or pyrimidine, or an optionally substituted cycloalkyl selected from cyclopropane, cyclobutane, cyclopentane, or cyclohexane;

Q represents O;

$R_{10}$ represents an optionally substituted C1-C6 alkyl, an optionally substituted cycloalkyl selected from cyclopropane, cyclobutane, cyclopentane, or cyclohexane, an optionally substituted aryl selected from phenyl or biphenyl, an optionally substituted heteroaryl selected from pyrazole or pyridine, or an optionally substituted heterocyclyl selected from oxetane, tetrahydrofuran, tetrahydropyran, azetidine, pyrrolidine, piperidine, morpholine, or piperazine;

$R_a$, $R_b$, $R_c$, $R_d$, are independently selected from the group consisting of hydrogen, halogen, an optionally substituted C1-C6 alkyl, an optionally substituted cycloalkyl selected from cyclopropane, cyclobutane, cyclopentane, or cyclohexane, an optionally substituted heterocyclyl selected from oxetane, tetrahydrofuran, or tetrahydropyran, an optionally substituted aryl selected from phenyl or biphenyl, an optionally substituted heteroaryl selected from thiophene, oxazole, thiazole, oxadiazole, imidazole, pyrazole, pyridine, pyridazine, pyrimidine, and pyrazine, alkoxy, cycloalkyloxy, aryloxy, heteroaryloxy, heterocyclyloxy, or trifluoromethoxy.

n is an integer from 1 to 12;

m is an integer from 0 to 12.

In certain embodiments n is an integer from 1 to 6, m is an integer from 0 to 6.

In certain embodiments, the compounds of Formula Ia are provided wherein,

A represents O, $R_1$ represents hydrogen, an optionally substituted cycloalkyl or a group C(=O)$R_5$ in which $R_5$ represents an optionally substituted lower alkyl, an optionally substituted aryl selected from phenyl, alpha- or beta-naphthyl, indanyl, and biphenyl, and an optionally substituted heteroaryl selected from thiophene, oxazole, thiazole, oxadiazole, imidazole, pyrazole, pyridine, pyridazine, pyrimidine, and pyrazine, or a group O—$R_{10}$;

$R_2$ and $R_3$ represent hydrogen;

Y, if present, is an optionally substituted alkyl or a group —$(CR_aR_b)_n$-Q-$(CR_eR_d)_m$—;

W is an optionally substituted aryl or heteroaryl, or an optionally substituted cycloalkyl;

Q represents O;

$R_{10}$ represents an optionally substituted C1-C6 alkyl, an optionally substituted cycloalkyl, an optionally substituted aryl, an optionally substituted heteroaryl, or an optionally substituted heterocyclyl;

$R_a$, $R_b$, $R_c$, $R_d$, are independently selected from the group consisting of hydrogen, halogen, an optionally substituted C1-C6 alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;

m is an integer from 0 to 12.

In certain embodiments a compound of Formula Ia is provided wherein

W is an optionally substituted aryl selected from phenyl, alpha- or beta-naphthyl, indanyl, biphenyl, or an optionally substituted heteroaryl selected from thiophene, thiazole, oxadiazole, pyrazole, pyridine pyridazine or pyrimidine, or an optionally substituted cycloalkyl selected from cyclopropane, cyclobutane, cyclopentane, or cyclohexane.

III. SUBSET OF COMPOUNDS OF FORMULA IB

The Inventors have also found that specific uracil derivatives where the 5 position of the uracil is substituted, the 6 position is unsubstituted, and the 1-carboxamide moiety bears an alkyl chain ending with a lipophilic group, retains an effective therapeutically activity, specifically an anticancer activity.

In accordance with this additional aspect of the invention, a subset of compounds of Formula Ib wherein A is O is provided

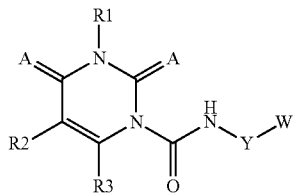

Formula Ib and wherein

Y, if present, represents an optionally substituted alkyl, an optionally substituted cycloalkyl or a group —$(CR_aR_b)_n$-Q-$(CR_cR_d)_m$—;

W represents hydrogen, an optionally substituted aryl, an optionally substituted heteroaryl, an optionally substituted cycloalkyl, a group —$(CR_eR_f)_p$—$CR_gR_hR_i$ or a group Z—$R_4$;

$R_1$ represents hydrogen, an optionally substituted alkyl, an optionally substituted alkenyl, an optionally substituted cycloalkyl, an optionally substituted heterocyclyl, or a group C(=O)$R_5$;

$R_2$ represents chlorine, bromine, iodine, an optionally substituted lower alkyl, an optionally substituted heterocyclyl, an optionally substituted aryl, or a group selected from O—$R_6$ or $NR_7R_8$;

$R_3$ represents hydrogen;

Q represents O, $NR_9$;

Z represents O, $NR_9$;

$R_4$ represents hydrogen, an optionally substituted alkyl, an optionally substituted cycloalkyl, an optionally substituted aryl, an optionally substituted heteroaryl, an optionally substituted heterocyclyl;

$R_5$ represents an optionally substituted lower alkyl, an optionally substituted cycloalkyl, an optionally substituted aryl, an optionally substituted heteroaryl, or a group O—$R_{10}$;

$R_6$ represents hydrogen, optionally substituted alkyl or an optionally substituted cycloalkyl;

$R_7$ and $R_8$ independently represent hydrogen, an optionally substituted lower alkyl, an optionally substituted cycloalkyl, an optionally substituted aryl, an optionally substituted heteroaryl, a group (C=O)$R_5$, or when, taken together with the nitrogen atom to which they are bound they represent an optionally substituted heterocyclyl;

$R_9$ represents hydrogen, an optionally substituted alkyl, an optionally substituted cycloalkyl, an optionally substituted aryl;

$R_{10}$ represents an optionally substituted alkyl, an optionally substituted cycloalkyl, an optionally substituted aryl, an optionally substituted heteroaryl, or an optionally substituted heterocyclyl;

$R_a$, $R_b$, $R_e$, $R_d$, $R_e$, $R_f$, $R_g$, $R_h$, and $R_i$ are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;
m is an integer from 0 to 12;
p is an integer from 0 to 6.

In certain embodiments of the subset of compounds of Formula Ib, the optionally substituted alkyl is a $C_1$-$C_8$ alkyl, optionally substituted with a group selected from halogen, cyano, trifluoromethyl, hydroxy, alkoxy, cycloalkyloxy, aryloxy, heteroaryloxy, heterocyclyloxy, or trifluoromethoxy.

In certain embodiments A represents O.

In certain embodiments of the subset of Formula Ib

A represents O,

Y, if present, represents an optionally substituted alkyl, preferably a lower alkyl, an optionally substituted cycloalkyl, or a group —$(CR_aR_b)_n$-Q-$(CR_cR_c)_m$—;

W represents hydrogen, an optionally substituted aryl, or an optionally substituted cycloalkyl;

$R_1$ represents hydrogen, an optionally substituted alkyl, an optionally substituted alkenyl, an optionally substituted cycloalkyl, an optionally substituted heterocyclyl, or a group C(=O)$R_5$;

$R_2$ represents chlorine, bromine, iodine, an optionally substituted lower alkyl, an optionally substituted heterocyclyl, an optionally substituted aryl, or a group selected from O—$R_6$ or $NR_7R_8$;

$R_3$ represents hydrogen;

Q represents O, $NR_9$;

$R_5$ represents an optionally substituted lower alkyl, an optionally substituted cycloalkyl, an optionally substituted aryl, an optionally substituted heteroaryl, or a group O—$R_{10}$;

$R_6$ represents hydrogen, an optionally substituted alkyl or an optionally substituted cycloalkyl;

$R_7$ and $R_8$ independently represent hydrogen, an optionally substituted lower alkyl, an optionally substituted cycloalkyl, an optionally substituted aryl, an optionally substituted heteroaryl, or when taken together with the nitrogen atom to which they are bound they represent an optionally substituted heterocyclyl;

$R_9$ represents hydrogen, an optionally substituted alkyl, an optionally substituted cycloalkyl, an optionally substituted aryl;

$R_{10}$ represents an optionally substituted alkyl, an optionally substituted cycloalkyl, an optionally substituted aryl, an optionally substituted heteroaryl, or an optionally substituted heterocyclyl;

$R_a$, $R_b$, $R_c$, $R_d$, are independently selected from the group consisting of hydrogen, halogen, an optionally substituted lower alkyl, an optionally substituted cycloalkyl, an optionally substituted heterocyclyl, an optionally substituted aryl, an optionally substituted heteroaryl, alkoxy, cycloalkyloxy, aryloxy, heteroaryloxy, heterocyclyloxy, or trifluoromethoxy.

n is an integer from 1 to 12;
m is an integer from 0 to 12.

In accordance with certain embodiments in the subset of Formula Ib,

A represents O,

Y represents an optionally substituted $C_1$-$C_8$ alkyl, or a group —$(CR_aR_b)_n$-Q-$(CR_cR_d)_m$—;

W represents hydrogen, an optionally substituted aryl, selected from phenyl, alpha- or beta-naphthyl, or biphenyl, an optionally substituted cycloalkyl selected from cyclopropane, cyclobutane, cyclopentane, or cyclohexane;

$R_1$ represents hydrogen, an optionally substituted C1-C8 alkyl, an optionally substituted cycloalkyl selected from cyclopropane, cyclobutane, cyclopentane, or cyclohexane, an optionally substituted heterocyclyl, or a group C(=O)$R_5$;

$R_2$ represents chlorine, bromine, iodine, an optionally substituted C1-C6 alkyl, an optionally substituted heterocyclyl selected from azetidine, pyrrolidine, piperidine, morpholine, or piperazine, an optionally substituted aryl selected from phenyl, alpha- or beta-naphthyl, or biphenyl, or a group selected from O—$R_6$ or $N1R_7R_8$;

$R_3$ represents hydrogen;

Q represents O;

$R_5$ represents an optionally substituted C1-C6 alkyl, an optionally substituted cycloalkyl selected from cyclopropane, cyclobutane, cyclopentane, or cyclohexane, an optionally substituted aryl selected from phenyl or biphenyl, an optionally substituted heteroaryl selected from thiophene, thiazole, oxadiazole, imidazole, pyrazole or pyridine, or a group O—$R_{10}$;

$R_6$ represents hydrogen, an optionally substituted C1-C8 alkyl or an optionally substituted cycloalkyl selected from cyclopropane, cyclobutane, cyclopentane, or cyclohexane;

$R_7$ and $R_8$ independently represent hydrogen, an optionally substituted C1-C6 alkyl, an optionally substituted cycloalkyl selected from cyclopropane, cyclobutane, cyclopentane, or cyclohexane, an optionally substituted aryl selected from phenyl, alpha- or beta-naphthyl, indanyl, or biphenyl, an optionally substituted heteroaryl selected from thiophene, thiazole, oxadiazole, imidazole, pyrazole or pyridine, or when taken together with the nitrogen atom to which they are bound they represent an optionally substituted heterocyclyl selected from azetidine, pyrrolidine, piperidine, morpholine, or piperazine.

$R_{10}$ represents an optionally substituted C1-C6 alkyl, an optionally substituted cycloalkyl selected from cyclopropane, cyclobutane, cyclopentane, or cyclohexane, an optionally substituted aryl selected from phenyl or biphenyl, an optionally substituted heteroaryl selected from pyrazole or pyridine, or an optionally substituted heterocyclyl selected from oxetane, tetrahydrofuran, tetrahydropyran, azetidine, pyrrolidine, piperidine, morpholine, or piperazine;

$R_a$, $R_b$, $R_c$, $R_d$, are independently selected from the group consisting of hydrogen, halogen, an optionally substituted C1-C6 alkyl, an optionally substituted cycloalkyl selected from cyclopropane, cyclobutane, cyclopentane, or cyclohexane, an optionally substituted heterocyclyl selected from oxetane, tetrahydrofuran, or tetrahydropyran, an optionally substituted aryl selected from phenyl or biphenyl, an optionally substituted heteroaryl selected from thiophene, oxazole, thiazole, oxadiazole, imidazole, pyrazole, pyridine, pyridazine, pyrimidine, and pyrazine, alkoxy, cycloalkyloxy, aryloxy, heteroaryloxy, heterocyclyloxy, or trifluoromethoxy.

n is an integer from 1 to 12;

m is an integer from 0 to 12.

According to certain embodiments of the subset of compounds of Formula Ib, n is an integer from 1 to 6, m is an integer from 0 to 6.

In accordance with some embodiments a compound of Formula Ib is provided wherein A represents O, Y represents an optionally substituted C1-C8 alkyl, or a group —$(CR_aR_b)_n$-Q-$(CR_cR_d)_m$—;

W represents hydrogen, an optionally substituted aryl, or an optionally substituted cycloalkyl;

$R_1$ represents hydrogen, an optionally substituted C1-C8 alkyl, an optionally substituted cycloalkyl, or a group C(=O)$R_5$;

$R_2$ represents chlorine, bromine, iodine, an optionally substituted C1-C6 alkyl, an optionally substituted heterocyclyl selected from azetidine, pyrrolidine, piperidine, piperazine, and morpholine, an optionally substituted aryl selected from phenyl, alpha- or beta-naphthyl, indanyl, and biphenyl, or a group selected from O—$R_6$ or NR$_7$R$_8$;

$R_3$ represents hydrogen;

Q represents O;

$R_5$ represents an optionally substituted C1-C6 alkyl, an optionally substituted cycloalkyl selected from cyclopropyl, cyclobutyl, cyclopentyl or cyclohexyl, an optionally substituted aryl selected from phenyl, or biphenyl, an optionally substituted heteroaryl selected from thiophene, thiazole, oxadiazole, imidazole, pyrazole or pyridine, or a group O—$R_{10}$;

$R_6$ represents hydrogen, an optionally substituted C1-C8 alkyl or an optionally substituted cycloalkyl;

$R_7$ and $R_8$ independently represent hydrogen, an optionally substituted C1-C6 alkyl, an optionally substituted cycloalkyl selected from cyclopropyl, cyclobutyl, cyclopentyl or cyclohexyl, an optionally substituted aryl selected from phenyl, alpha- or beta-naphthyl, indanyl, and biphenyl, an optionally substituted heteroaryl selected from thiophene, oxazole, thiazole, oxadiazole, imidazole, pyrazole, pyridine, pyridazine, pyrimidine or pyrazine, or when taken together with the nitrogen atom to which they are bound they represent an optionally substituted heterocyclyl selected from azetidine, pyrrolidine, piperidine, piperazine, and morpholine.

$R_{10}$ represents an optionally substituted C1-C6 alkyl, an optionally substituted cycloalkyl selected from cyclopropane, cyclobutane, cyclopentane, or cyclohexane, an optionally substituted aryl selected from phenyl or biphenyl, an optionally substituted heteroaryl selected from pyrazole or pyridine, or an optionally substituted heterocyclyl selected from oxetane, tetrahydrofuran, tetrahydropyran, azetidine, pyrrolidine, piperidine, morpholine, or piperazine;

$R_a$, $R_b$, $R_c$, $R_d$, are independently selected from the group consisting of hydrogen, halogen, an optionally substituted C1-C6 alkyl, an optionally substituted cycloalkyl selected from cyclopropane, cyclobutane, cyclopentane, or cyclohexane, an optionally substituted heterocyclyl selected from oxetane, tetrahydrofuran, or tetrahydropyran, an optionally substituted aryl selected from phenyl or biphenyl, alkoxy, cycloalkyloxy, aryloxy, heteroaryloxy, heterocyclyloxy, or trifluoromethoxy.

n is an integer from 1 to 12;

m is an integer from 0 to 12.

Typically, the subset of compounds of Formula Ia and Ib may exist as (R)- and (S)-enantiomer and as racemic mixture. This invention includes in its scope of protection all the possible isomers and racemic mixtures thereof. Wherever should be present further symmetry centers, this invention includes all the possible diastereoisomers and relative mixtures as well.

IV. DEFINITIONS

All technical and scientific terms used herein have the same meaning as commonly understood by a person of ordinary skill in the art, unless otherwise defined.

The following terms, used in the specification and claims of this application have the meaning specified hereunder, unless otherwise defined.

The term "alkyl", as used herein, indicates a saturated aliphatic hydrocarbon radical, including straight chain and branched chain radicals of 1 to 16 carbon atoms. In certain embodiments, alkyl refers, in particular to 1 to 12 carbon atoms. The term "lower alkyl", as used herein, refers to straight chain and branched chain radicals of 1 to 6 carbon atoms. Non-limiting examples of alkyl are, for instance, methyl, ethyl, propyl, isopropyl, n-butyl, iso-butyl, tert-butyl, n-amyl, iso-amyl, n-hexyl, n-heptyl, n-octyl and the like.

Any alkyl group may be unsubstituted or substituted by one or more substituents. Thus, the term "substituted alkyl" comprises alkyl groups as defined hereinabove in which one or more atoms or functional groups of the alkyl moiety are replaced with another atom or functional group including, by way of example, alkyl, halogen, aryl, substituted aryl, hydroxyl, amino, alkoxyl, alkylamino, sulfate. In certain embodiments alkyl is substituted by one or more substituents independently selected from the group consisting of halogen, trifluoromethyl, hydroxy, alkoxy, trifluoromethoxy, amino, monoalkylamino, or dialkylamino.

The term "alkenyl", as used herein, indicates an alkyl group, as defined herein, consisting of at least two carbon atoms and containing at least one carbon-carbon double bond. Representative examples include, but are not limited to, ethenyl, 1-propenyl, 2-propenyl, 1- or 2-butenyl, and the like. Any alkenyl group may be unsubstituted or substituted by one or more substituents independently selected from the group consisting of halogen, trifluoromethyl, hydroxy, alkoxy, trifluoromethoxy, amino, monoalkylamino, or dialkylamino.

The term "alkynyl", as used herein, indicates an alkyl group, as defined herein, consisting of at least two carbon atoms and containing at least one carbon-carbon triple bond. Representative examples include, but are not limited to, ethynyl, 1-propynyl, 2-propynyl, 1- or 2-butynyl, and the like. Any alkynyl group may be unsubstituted or substituted by one or more substituents independently selected from the group consisting of halogen, trifluoromethyl, hydroxy, alkoxy, trifluoromethoxy, amino, monoalkylamino, or dialkylamino.

The term "cycloalkyl", as used herein, indicates a 3- to 7-membered all-carbon monocyclic ring, which may contain one or more double bonds but does not have a completely conjugated pi-electron system.

Examples of cycloalkyl groups include, without limitation, cyclopropane, cyclobutane, cyclopentane, cyclopentene, cyclohexane, cyclohexene, cyclohexadiene, and cycloheptane.

In certain embodiments a suitable cycloalkyl group is selected from cyclopropane, cyclobutane, cyclopentane, cyclohexane, and cycloheptane.

A cycloalkyl group may be unsubstituted or substituted by one to three substituents independently selected from the group comprising lower alkyl, halogen, trifluoromethyl, hydroxy, alkoxy, trifluoromethoxy, amino, monoalkylamino, or dialkylamino.

The term "aryl", as used herein, indicates a hydrocarbon consisting of a mono-, bi- or tricyclic ring system, wherein the rings are fused together or linked to each other covalently and at least one of the carbocyclic rings is aromatic. In particular embodiments, the term "aryl" means a cyclic aromatic such as a 6-membered hydrocarbon, a two six-membered fused hydrocarbon, and a two six-membered hydrocarbon covalently bonded.

Not limiting examples of aryl groups include, but are not limited to, phenyl, alpha- or beta-naphthyl, 9,10-dihydroanthracenyl, indanyl, fluorenyl, biphenyl and the like. The aryl group may be optionally substituted ("substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NK'K", wherein K' and K" can each be independently hydrogen, alkyl, substituted alkyl, aryl, substituted aryl, and aralkyl.

The term "heteroaryl", as used herein, indicates a mono-, bi- or tricyclic ring system containing from one to three heteroatoms selected from nitrogen, oxygen and sulfur, wherein the rings are fused together or linked to each other covalently and at least one of the rings is aromatic.

Not limiting examples of heteroaryl groups include pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl.

In certain embodiments a suitable heteroaryl group is selected from thiophenyl, furoyl, oxazolyl, thiazolyl, imidazolyl, pyrazolyl, benzofuranyl, benzothiophenyl, oxadiazolyl, pyridyl, pyrazinyl, pyrimidinyl, pyridazinyl, and quinazolinyl.

A heteroaryl group may be unsubstituted or substituted (substituted heteroaryl) with one or more heteroaryl group substituents, which can be the same or different, wherein "heteroaryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NK'K", wherein K' and K" can each be independently hydrogen, alkyl, substituted alkyl, aryl, substituted aryl, and aralkyl, The terms "heterocyclyl" or "heterocyclic ring", as used herein, mean a 3- to 7-membered, saturated or partially unsaturated carbocyclic ring wherein one or more carbon atoms are independently replaced by nitrogen, oxygen and sulfur. The heteroatom nitrogen and sulfur are optionally oxidized, and the nitrogen atom(s) are optionally quaternized. Not limiting examples of heterocyclyl groups include, for instance, radicals derived from oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, examethyleneimine, homopiperazine, and the like.

A heterocyclyl group or a heterocyclic ring may be unsubstituted or substituted by one to three substituents independently selected from the group consisting of lower alkyl, halogen, trifluoromethyl, hydroxy, alkoxy, trifluoromethoxy, amino, monoalkylamino, or dialkylamino.

In certain embodiments a suitable heterocyclyl group is selected from oxetane, tetrahydrofuran, pyran, dihydropyran, tetrahydropyran, dioxane, oxazoline, azetidine, pyrrolidine, piperidine, piperazine, and morpholine.

The term "aromatic" refers to a moiety wherein the constituent atoms make up an unsaturated ring system, all atoms in the ring system are sp2 hybridized and the total number of pi electrons is equal to 4n+2, wherein n is an integer.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like.

The term "amino" means a —NH$_2$ radical.

The term "aryloxy", as used herein, means an unsubstituted or substituted aryl group linked to the remainder of the molecule through an oxygen atom. Examples of aryloxy include, but are not limited to, phenoxy, alpha- or beta-naphthyloxy, biphenyloxy and the like.

The term "cycloalkyloxy", as used therein, means an unsubstituted or substituted cycloalkyl group linked to the remainder of the molecule through an oxygen atom. Examples of cycloalkyloxy include, but are not limited, to cyclopropyloxy, cyclobutyloxy, cyclopentyloxy, cyclopentenyloxy, cyclohexyloxy, cyclohexenyloxy, cyclohexadienyloxy, cycloheptanyloxy and the like.

The term "heteroaryloxy", as used therein, means an unsubstituted or substituted heteroaryl group linked to the remainder of the molecule through an oxygen atom.

The term "heterocyclyloxy", used therein, means an unsubstituted or substituted heterocyclyl group linked to the remainder of the molecule through an oxygen atom.

The term "halogen", as used herein, indicates fluorine (F), chlorine (Cl), bromine (Br) or iodine (I).

The term "hydroxyl" means a —OH radical.

The term "monoalkylamino", as used herein, represents an amino group wherein one of the hydrogen atoms is substituted by an alkyl chain. Not limiting examples of monoalkylamino include methylamino, ethylamino, propylamino, butylamino and the like.

The term "dialkylamino", as used herein, represents an amino group wherein both hydrogen atoms are substituted by an alkyl chain. The two alkyl chains can be the same or different. Not limiting examples of dialkylamino include dimethylamino, diethylamino, dipropylamino, methylethylamino, methylisopropylamino and the like.

The term "trifluoromethyl" means a CF$_3$ radical.

The term "trifluoromethoxy" means a OCF$_3$ radical.

V. PHARMACEUTICALLY ACCEPTABLE SALTS

It will be understood that, as used herein, references to the compounds of Formula I, Ia, Ib are meant to include also the pharmaceutically acceptable salts or derivatives thereof.

Furthermore, the compound of the Formula I, Ia, Ib may form an acid addition salt or a salt with a base, depending on the kind of the substituents, and these salts are included in the present invention, as long as they are pharmaceutically acceptable salts.

The terms "the compound of the invention" and "the compounds of the present invention" and "the compounds of Formula I" refer to each of the compounds of Formulae I, Ia, Ib, and are meant to include their pharmaceutically acceptable salts, hydrates, solvates, and crystalline forms and also any suitable forms as illustrated hereinafter.

As used herein, the term "salt" refers to any salt of a compound according to the present invention prepared from an inorganic or organic acid or base and internally formed salts. Typically, such salts have a physiologically acceptable anion or cation.

Suitably physiologically or pharmaceutically acceptable salts of the compounds of the present invention include the hydrochloride, acetate, citrate, gluconate, lactate, tartrate, phosphate, borate, maleate, sulphate and nitrate, the hydrochloride being preferred.

The salts of compounds of Formula I, Ia, Ib may be prepared by reacting a basic compound with the desired acid in solution.

Physiologically or pharmaceutically acceptable salts are particularly suitable for medical applications because of their greater aqueous solubility relative to the parent compounds.

Pharmaceutical acceptable salts may also be prepared from other salts, including other pharmaceutically acceptable salts, of the compounds of Formula I, Ia, Ib, using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of Formula I may readily be isolated in association with solvent molecules by crystallisation or evaporation of an appropriate solvent to give the corresponding solvates.

The compounds of Formulae I, Ia, Ib of the invention may be in crystalline forms. In certain embodiments, the crystalline forms of the compounds of Formulae I, Ia, Ib are polymorphs.

The subject invention also includes isotopically-labelled compounds, which are identical to those recited in Formula I and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{35}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I and following of this invention can generally be prepared by carrying out the procedures disclosed in the Schemes and/or in the Examples below, by substituting, a readily available isotopically labelled reagent for a non-isotopically labelled reagent.

Certain groups/substituents included in the present invention may be present as isomers or in one or more tautomeric forms. Accordingly, in certain embodiments, the compound of the Formulae I, Ia, Ib may exist in the form of other tautomers or geometrical isomers in some cases, depending on the kinds of the substituents. In the present specification, the compound may be described in only one form of such isomers, but the present invention includes such isomers, isolated forms of the isomers, or a mixture thereof. Furthermore, the compound of the Formulae I, Ia, Ib may have asymmetric carbon atoms or axial asymmetries in some cases, and correspondingly, it may exist in the form of optical isomers such as an (R)-form, an (S)-form, and the like. The present invention includes within its scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formulae I, Ia, Ib, include all the stereoisomeric forms, unless otherwise indicated. In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

VI. METHODS FOR PREPARING COMPOUNDS OF FORMULA I, IA, IB

In a further aspect the present invention provides methods for preparing compounds of Formula I, including those of Formulae Ia, Ib.

The compounds of Formula I, can be prepared through a process including synthetic transformations reported, for instance, in Michael Smith, Jerry March—*March's Advanced Organic Chemistry: reactions mechanisms and structure*—6th Edition, John Wiley & Sons Inc., 2007, which is herein incorporated as reference. It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W Green and Peter G. M. Wuts—*Protective Groups in Organic Synthesis*, Fourth Edition, John Wiley & Sons Inc., 2006, which is herein incorporated as reference.

It will be understood that, as used herein, references to the compounds of Formula. I are meant to include also the subsets of compounds of Formulae Ia and Ib, as described hereinafter, where appropriate.

In certain embodiments, a compound of Formula I can be obtained by reaction of compound of Formula II, or a salt thereof, with an isocyanate of Formula III,

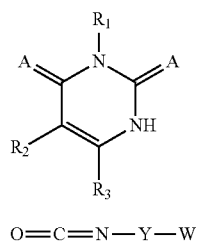

II

III

O=C=N—Y—W wherein A, $R_2$, $R_3$, Y, and W are as defined above, and $R_1$ represents hydrogen, an optionally substituted alkyl, an optionally substituted alkenyl, an optionally substituted cycloalkyl, an optionally substituted aryl, an optionally substituted heteroaryl, or an optionally substituted heterocyclyl.

Compounds of Formula II are either commercially available or can be prepared according to standard synthetic methods as reported, for instance, in Michael Smith, Jerry March—*March's Advanced Organic Chemistry: reaction mechanisms and structure*—6$^{th}$ Edition, John Wiley & Sons Inc, 2007; or in Javier I. Bardagl, Roberto A. Rossi—*Organic Preparations and Procedures International*, 2009, 41, 479-514 and references cited therein, which are incorporated herein as reference. In one embodiment, a compound of Formula II can be obtained by treating another compound represented by the same Formula II with suitable reagents in order to remove one or more protective groups introduced in one of the synthetic steps, as known to those skilled in the art. Protection of such reactive centers, and subsequent de-protection, can be accomplished following standard procedures described, for instance, in Theodora W. Greene and Peter G. M. Wuts—*Protective Groups in Organic Synthesis*, Fourth Edition, John Wiley & Sons Inc., 2006, which is herein incorporated as reference.

In another embodiment, a compound of Formula II can be obtained by treating another compound represented by the same Formula II with suitable reagents in order to transform one or more functional groups into one or more new functional groups.

An isocyanate of Formula III, as defined above, is either commercially available or can be prepared by synthetic methods as reported, for instance, in Molina P., Tarraga A., Argues A. in Katritzky A. R., Taylor R. J. k., *Comprehensive Organic Functional Group Transformations II*, Elsevier, 2004, Vol. 5, Pag. 949-973; or in Michael Smith, Jerry March—*March's Advanced Organic Chemistry reaction mechanisms and structure*—6$^{th}$ Edition, John Wiley & Sons Inc., 2007, and references cited therein, which are incorporated herein as reference.

A compound of Formula II, wherein $R_1$ and $R_3$ represent hydrogen, A is as defined above, and $R_2$ represents a group $NR_7R_8$, can be obtained by reaction of a compound of Formula IV, wherein A is as defined above, with a secondary amine of Formula V,

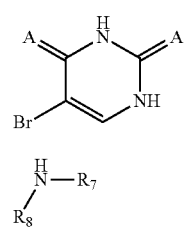

IV

V wherein $R_7$ and $R_8$ independently represent hydrogen, an optionally substituted alkyl, an optionally substituted cycloalkyl, an optionally substituted aryl, an optionally substituted heteroaryl, an optionally substituted heterocyclyl, or when taken together with the nitrogen atom to which they are bound they represent an optionally substituted heterocyclyl.

An amine of Formula V, as defined above, is either commercially available or can be prepared from suitable precursors, as known to a person skilled in the art, according to standard synthetic methods as reported, for instance, in Michael Smith, Jerry March—*March's Advanced Organic Chemistry: reaction mechanisms and structure*—6*th* Edition, John Wiley & Sons Inc., 2007, and references cited therein, which is incorporated herein as reference.

A compound of Formula II, wherein $R_1$ and A are as defined above, $R_3$ represents hydrogen, and $R_2$ represents an optionally substituted aryl, can be obtained by acid-mediated cleavage of the benzhydryl group of a compound of Formula VI

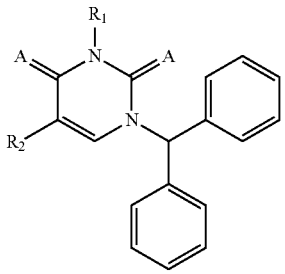

VI wherein $R_1$ and A are as defined above, and $R_2$ represents an optionally substituted aryl.

A compound of Formula VI, as defined above, can be obtained by metal-catalyzed cross coupling reaction between a compound of Formula VII, wherein $R_1$ and A are as defined above, and a boronic acid of Formula VIII

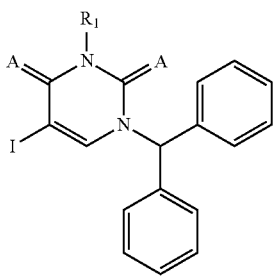

VII

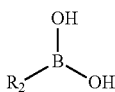

VIII wherein $R_2$ represents an optionally substituted aryl.

A compound of Formula VII, as defined above, can be, obtained by reaction of a compound of Formula II, wherein $R_1$ and A are as defined above, $R_2$ is iodine, and $R_3$ is hydrogen with bromodiphenyl methane, as known to those skilled in the art, according to standard synthetic procedures, as reported, for instance, in Fan Wu, Musole G. Buhendwa, Donald F. Weaver, *Journal of Organic Chemistry,* 2004, 69, 9307-9309, and references cited therein, which is incorporated herein as reference.

A boronic acid of Formula VIII, as defined above, is either commercially available or can be prepared from suitable precursors, as known to a person skilled in the art, according to standard synthetic methods as reported, for instance, in Norio Miyaura and Akira Suzuki, *Palladium-Catalyzed Cross-Coupling Reactions of Organoboron Compounds. Chemical Reviews* 1995, 95, 2457-2483, or in Michael Smith, Jerry March—*March's Advanced Organic Chemistry: reaction mechanisms and structure*—6*th* Edition, John Wiley & Sons Inc., 2007, and references cited therein, which are incorporated herein as references.

In another embodiment, a compound of Formula II, wherein $R_2$ and A are as defined above, $R_3$ represents hydrogen, and $R_1$ represents an optionally substituted alkyl, an optionally substituted alkenyl, an optionally substituted cycloalkyl, an optionally substituted aryl, an optionally substituted heteroaryl, or an optionally substituted heterocyclyl, can be obtained by base-mediated cleavage of the tert-butyloxycarbonyl group of a compound of Formula IX

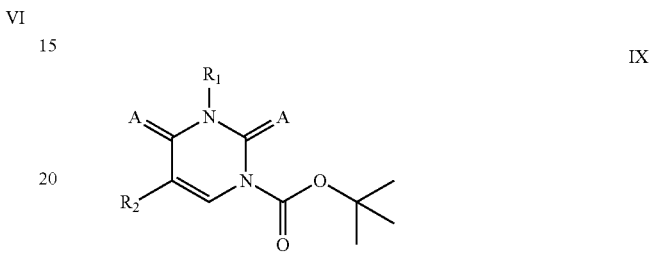

IX wherein $R_2$ and A are as defined above, and $R_1$ represents an optionally substituted alkyl, an optionally substituted alkenyl, an optionally substituted cycloalkyl, an optionally substituted aryl, an optionally substituted heteroaryl, or an optionally substituted heterocyclyl.

A compound of Formula IX, as defined above, can be obtained by reaction of compound of Formula X, wherein $R_2$ and A are as defined above, with an halide of Formula XI,

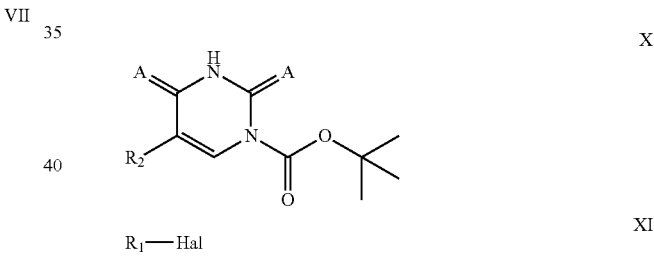

X

XI $R_1$—Hal wherein Hal represent bromine or iodine, and $R_1$ is an optionally substituted alkyl, an optionally substituted alkenyl, an optionally substituted cycloalkyl, or an optionally substituted aryl.

A compound of Formula X, as defined above, can be obtained by reaction of a compound of Formula II, wherein A and $R_2$ are as defined above, and $R_1$ and $R_3$ represent hydrogen, with di-tert-butyl dicarbonate, according to standard synthetic procedures, as known to those skilled in the art.

A halide of Formula XI, as defined above, is either commercially available or can be prepared from suitable precursors, as known to a person skilled in the art, according to standard synthetic methods as reported, for instance, in Michael Smith, Jerry March—*March's Advanced Organic Chemistry; reaction mechanisms and structure*—6*th* Edition, John Wiley & Sons Inc, 2007, and references cited therein, which is incorporated herein as reference.

In another embodiment, a compound of Formula I, wherein A, $R_1$, $R_2$, $R_3$, Y, and W are as defined above, can be obtained by activation of a compound of Formula II, wherein A, $R_1$, $R_2$, and $R_3$ are as defined above, as carbamoyl chloride and subsequent reaction with an amine of Formula XII,

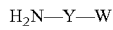   XII wherein Y and W are as defined above.

An amine of Formula XII is either commercially available or can be prepared from suitable precursors, as known to a person skilled in the art, according to standard synthetic methods as reported, for instance, in Michael Smith, Jerry March—*March's Advanced Organic Chemistry: reaction mechanisms and structure*—6$^{th}$ Edition, John Wiley & Sons Inc., 2007, and references cited therein which is incorporated herein as reference.

In another embodiment, a compound of Formula I can be obtained by a process which comprises converting a compound of Formula I into another compound represented by the same Formula I. Such a conversion is illustrated by, but is not limited to, the following examples.

A compound of Formula I, wherein $R_3$, Y and W are as defined above, $R_1$ represents a group (C=O)$R_5$, wherein $R_5$ is as defined above, and $R_2$ represents hydrogen, chlorine, bromine, iodine, an optionally substituted lower alkyl, an optionally substituted heterocyclyl, an optionally substituted aryl, an optionally substituted heteroaryl, or a group selected from —CN, O—$R_6$, S—$R_6$, or N$R_7R_8$, wherein $R_7$ and $R_8$ are different from hydrogen, can be obtained by treating another compound represented by the same Formula I, wherein $R_3$, Y and W are as defined above, $R_1$ represents hydrogen, and $R_2$ represents hydrogen, chlorine, bromine, iodine, an optionally substituted lower alkyl, an optionally substituted heterocyclyl, an optionally substituted aryl, an optionally substituted heteroaryl, or a group selected from —CN, O—$R_6$, S—$R_6$, or N$R_7R_8$, wherein $R_7$ and $R_8$ are different from hydrogen, with a suitable chloride of Formula XIII,

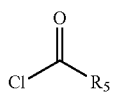   XIII wherein $R_5$ is as defined above.

A compound of Formula I, wherein $R_1$, $R_3$, Y and W are as defined above, $R_2$ represents a group N$R_7R_8$, wherein $R_7$ represents a group (C=O)$R_6$, wherein $R_5$ is as defined above, and $R_8$ represents hydrogen or an optionally substituted lower alkyl, an optionally substituted cycloalkyl an optionally substituted aryl, an optionally substituted heteroaryl, an optionally substituted heterocyclyl, can be obtained by treating another compound represented by the same Formula I, wherein $R_1$, $R_3$, Y and W are as defined above, $R_2$ represents a group N$R_7R_8$, wherein. $R_7$ represents hydrogen and $R_8$ represents hydrogen or an optionally substituted lower alkyl, an optionally substituted cycloalkyl an optionally substituted aryl, an optionally substituted heteroaryl, an optionally substituted heterocyclyl, with a suitable chloride of Formula XIII, wherein $R_5$ is as defined above.

A chloride of Formula XIII is either commercially available or can be prepared from suitable precursors, as known to a person skilled in the art, according to standard synthetic methods as reported, for instance, in Michael Smith, Jerry March—*March's Advanced Organic Chemistry: reaction mechanisms and structure*—6$^{th}$ Edition, John Wiley & Sons Inc., 2007, and references cited therein, which is incorporated herein as reference.

The synthesis of a compound of Formula I, according to the synthetic processes described above, can be conducted in a stepwise manner, whereby each intermediate is isolated and purified by standard placation techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds described above can be prepared as exemplified in the following procedures.

A compound of Formula I, wherein A, $R_2$, $R_3$, Y, and W are as defined above, and $R_1$ represents hydrogen, an optionally substituted alkyl, an optionally substituted alkenyl, an optionally substituted cycloalkyl, an optionally substituted aryl, an optionally substituted heteroaryl, or an optionally substituted heterocyclyl, can be obtained by reaction of a compound of Formula II, as defined above, with an isocyanate of Formula III, as defined above. The reaction is preferably conducted in anhydrous, polar aprotic solvents, such as pyridine, dimethylsulfoxide (DMSO), tetrahydrofuran (THF), dichloromethane, and the like, at a temperature ranging from room temperature to 100° C., and for a period of time from 10 minutes to 18 hours. The reaction can be conducted in the presence of tertiary amines such as 4-dimethylaminopyridine, di-isopropyl ethyl amine and the like.

A compound of Formula II, wherein $R_1$ and $R_3$ represent hydrogen, A is as defined above, and $R_2$ represents a group N$R_7R_8$, can be obtained by reaction of a compound of Formula IV, as defined above, with a secondary amine of Formula V, as defined above. The reaction is preferably conducted without solvent, under microwave irradiation at a temperature ranging from 90° C. to 160° C., and for a period of time from 10 minutes to 6 hours.

A compound of Formula II, wherein $R_1$ and A are as defined above, $R_3$ represents hydrogen, and $R_2$ represents an optionally substituted aryl, can be obtained treating a compound of Formula VI, as defined above, with strong inorganic acids, such as trifluoromethanesulfonic acid. The reaction is carried out preferably in trifluoroacetic acid (TFA), at a temperature ranging from −10° C. to room temperature, and for a period of time from 1 hour to 5 hours.

A compound of Formula VI, wherein $R_1$ and A are as defined above, and $R_2$ represents an optionally substituted aryl, can be obtained by metal-catalyzed cross coupling reaction between a compound of Formula VII, as defined above, and a boronic, acid of Formula VIII, as defined above. The reaction is preferably conducted in mixture of solvents such as toluene/ethanol, acetonitrile/water, tetrahydrofuran/water, or solvents such as N,N-dimethylformamide (DMF), dimethoxyethane (DME), dioxane, at a temperature ranging from room temperature to 160° C. and a period of time from 10 minutes to 48 hours. The reaction requires the presence of an inorganic base, such as sodium carbonate ($Na_2CO_3$), potassium carbonate ($K_2CO_3$), cesium carbonate ($Cs_2CO_3$), barium hydroxide (Ba(OH)$_2$), sodium hydroxide (NaOH); potassium fluoride (KF), and the like, and a catalyst containing palladium, such as tetrakis(triphenylphosphine) palladium(0), palladium (II) acetate, and the like.

A compound of Formula VII, wherein $R_1$ and A are as defined above, can be obtained by reaction of a compound of Formula wherein $R_1$ and A are as defined above, $R_2$ is iodine and $R_3$ is hydrogen, with bromodiphenyl methane. The reaction is carried out in a suitable solvent such as acetonitrile, tetrahydrofuran (THF), and the like, at a temperature ranging from room temperature to 90° C. and for a period of time from 2 hours to 10 hours. The reaction is conducted in the presence of silyl-containing O-protecting reagents, such as bis(trimethylsilyl)acetamide (BSA) and the like, and in the presence of catalysts, such as iodine ($I_2$) and tetrabutylammonium iodine, and the like.

A compound of Formula II, wherein $R_2$ and A are as defined above, $R_3$ represents hydrogen, and $R_1$ represents an optionally substituted alkyl, an optionally substituted alkenyl, an optionally substituted cycloalkyl, an optionally substituted aryl, an optionally substituted heteroaryl, or an optionally substituted heterocyclyl, can be obtained by base-mediated cleavage of the tert-butyloxycarbonyl group of a compound of Formula IX, as defined above. The reaction is conducted in a polar protic solvent such as water, methanol, ethanol, and the like, and in the presence of a base such as potassium carbonate ($K_2CO_3$), potassium tert-butoxide, and the like. The reaction is carried out at a temperature ranging from 0° C. to 100° C. and for a period of time from 15 minutes to 18 hours.

A compound of Formula IX, wherein $R_2$ and A are as defined above, and $R_1$ represents an optionally substituted alkyl, an optionally substituted alkenyl, an optionally substituted cycloalkyl, an optionally substituted aryl, an optionally substituted heteroaryl, or an optionally substituted heterocyclyl, can be obtained by reaction of a compound of Formula X, as defined above, with an halide of Formula XI, as defined above. The reaction is carried out in a suitable solvent such as N,N-dimethylformamide (DMF), acetonitrile (MeCN), tetrahydrofuran (THF), and the like, and in the presence of an inorganic base such as sodium hydride (NaH), sodium carbonate ($Na_2CO_3$), potassium carbonate ($K_2CO_3$), cesium carbonate ($Cs_2CO_3$), and the like, at a temperature ranging from 0° C. to 40° C. and for a period of time from 1 hour to 18 hours.

A compound of Formula X, wherein $R_2$ and A are as defined above, can be obtained by reaction of a compound of Formula II, wherein A is as defined above, and $R_1$ and $R_3$ represent hydrogen, with di-tert-butyldicarbonate. The reaction is conducted in a suitable solvent such as acetonitrile, tetrahydrofuran (THF), N,N-dimethylformamide (DMF), dichloromethane, dimethoxyethane (DME), and the like, at a temperature ranging from 0° C. to 50° C. and for a period of time from 1 hours to 18 hours. Occasionally, the reaction can be conducted in the presence of tertiary amines such as 4-dimethylaminopyridine, di-isopropyl ethyl amine, imidazole, triethylamine, and the like.

A compound of Formula I, as defined above, can be prepared by treating a compound of Formula II, as defined above, with an activating agent such as phosgene, ethyl chloroformate, p-nitrophenylchloroformate, 1,1'-carbonyldiimidazole, triphosgene, and the like, and subsequent reaction with an amine of Formula XII, as defined above. Such reaction is carried out in a so-called "one-pot" procedure, in a suitable solvent such as dichloromethane, chloroform, acetonitrile, tetrahydrofuran, pyridine, or mixtures thereof, and in the presence of a suitable base such as triethylamine, di-isopropylethylamine, or pyridine, at a temperature ranging from –10° C. to 40° C., and for a period of time from 1 hour to 72 hours.

A compound of Formula I, wherein $R_3$, Y and W are as defined above, represents a group (C=O)$R_6$, and $R_2$ represents hydrogen, chlorine, bromine, iodine, an optionally substituted lower alkyl, an optionally substituted heterocyclyl, an optionally substituted aryl, an optionally substituted heteroaryl, or a group selected from —CN, O—$R_6$, S—$R_6$, or N$R_7R_8$, wherein $R_7$ and $R_8$ are different from hydrogen, can be obtained by treating another compound represented by the same Formula I, wherein $R_1$, $R_3$, Y and W are as defined above, $R_2$ represents hydrogen, chlorine, bromine, iodine, an optionally substituted lower alkyl, an optionally substituted heterocyclyl, an optionally substituted aryl, an optionally substituted heteroaryl, or a group selected from —CN, O—$R_6$, S—$R_6$, or a group N$R_7R_8$, wherein $R_7$ and $R_8$ are different from hydrogen, with a chloride of Formula XIII, as defined above. Such reaction is conducted in a suitable solvent such as dichloromethane, chloroform, acetonitrile, tetrahydrofuran, pyridine, or mixtures thereof, and in the presence of a suitable base such as triethylamine, di-isopropyl ethyl amine, or pyridine, at a temperature ranging from –10° C. to 40° C., and for a period of time from 1 hour to 72 hours.

A compound of Formula I, wherein $R_1$, $R_3$, Y and W are as defined above, and $R_2$ represents a group N$R_7R_8$, wherein $R_7$ represents a group (C=O)$R_5$ and $R_8$ represents hydrogen, an optionally substituted lower alkyl, an optionally substituted cycloalkyl an optionally substituted aryl, an optionally substituted heteroaryl, or an optionally substituted heterocyclyl, can be obtained by treating another compound represented by the same Formula I, wherein $R_1$, $R_3$, Y and W are as defined above, $R_2$ represents a group N$R_7R_8$, wherein $R_7$ represents hydrogen and $R_8$ represents hydrogen or an optionally substituted lower alkyl, an optionally substituted cycloalkyl an optionally substituted aryl, an optionally substituted heteroaryl, an optionally substituted heterocyclyl, with a chloride of Formula XIII, as defined above. Such reaction is conducted in a suitable solvent such as dichloromethane, chloroform, acetonitrile, tetrahydrofuran, pyridine, or mixtures thereof, and in the presence of a suitable base such as triethylamine, di-isopropylethylamine, or pyridine, at a temperature ranging from –10° C. to 40° C., and for a period of time from 1 hour to 72 hours.

VII. MEDICAL USES OF COMPOUNDS OF FORMULA I, IA, IB

In accordance with a second aspect of the present invention compounds of Formula I, Ia, Ib are provided for use as a medicament.

In accordance with an additional aspect, the present invention provides the compounds of Formula I, Ia, Ib for use in treating diseases or disorders associated with increased (relative to physiological or desired) levels of acid ceramidase protein or function, for example in subjects where acid ceramidase is overactive or over-expressed.

In accordance with an additional aspect, a method of treatment of diseases or disorders associated with increased (relative to physiological or desired) levels of acid ceramidase protein or function, for example in subjects where acid ceramidase is overactive or over-expressed is also provided.

In some embodiments, the compounds of Formula I, Ia, Ib, and their pharmaceutical compositions and methods of administering them, are useful in treating diseases or disorders involving cell overproliferation and/or dysfunctional sphingolipid signal transduction.

These diseases and disorders include, but are not limited to, primary and metastatic neoplastic diseases. Diseases and disorders involving cell overproliferation include, but are not limited to, pre-malignant conditions, for example hyperplasia, metaplasia or dysplasia, cancer, cancer metastasis, benign tumors, hyperproliferative disorders and benign dysproliferative disorders.

The treatment may be prophylactic or therapeutic.

The subject to be treated may be an animal (e.g., mouse, rat, non-human primate and non-human mammal) or human.

Primary and metastatic neoplastic diseases and related disorders that can be treated and/or prevented by the methods, compounds and compositions of the presently disclosed subject matter include, but are not limited to, prostate cancer, colorectal cancer, liver cancer, head and neck cancer, breast cancer, melanoma, metastatic melanoma, precancerous skin conditions such as actinic keratosis, skin cancers such as squamous cell carcinoma and basal cell carcinoma, and hematological malignancies such as chronic myelogeneous leukemia. In accordance with certain embodiments the present invention provides a method for the treatment or prevention of cancer, cancer metastasis, or psoriasis, comprising the administration of a therapeutically effective compound of Formula I, Ia, Ib according to one or more of the embodiments described above, in a subject in need of treatment.

Cancers and related disorders that can be treated and/or prevented by the methods and compositions of the presently disclosed subject matter include, but are not limited to acute and chronic leukemia; polycythemia vera; lymphomas such as Hodgkin's disease, non-Hodgkin's disease; multiple myelomas, plasmacytoma; Waldenstrom's acroglobulinemia; gammopathy; heavy chain disease; bone and connective tissue sarcomas; brain tumors; breast cancer; adrenal cancer; thyroid cancer; pancreatic cancer; pituitary cancers; eye cancers; vaginal cancers; vulvar cancer; cervical cancers; uterine cancers; ovarian cancers; head and neck squamous cell cancers (HNSCCs), esophageal cancers; stomach cancers; colon cancers; rectal cancers; liver cancers; cholangiocarcinomas; testicular cancers, prostate cancers; penal cancers; oral cancers; basal cancers; salivary gland cancers; pharynx cancers; skin cancers; kidney cancers; Wilms' tumor; bladder cancers, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. In certain embodiments, the present invention provides for compounds of Formula I, Ia, Ib for the use in the treatment and/or prevention of breast cancer, prostate cancer, melanoma, alveolar cancer, or head and neck cancer.

In some embodiments, the compounds of Formula I, and their pharmaceutical compositions and methods of administering them, are useful in treating or preventing a disease or disorder when administered in combination with other treatments.

In an additional aspect the present invention also concerns combination therapies or treatment with a compound of Formula I, Ia, Ib or pharmaceutical composition containing them.

In some embodiments, the compounds of Formula I, and their pharmaceutical compositions and methods of administering them, are useful in treating cancer when administered in combination with other pharmacological agents or active ingredients.

In certain embodiments these pharmacological agents are chemotherapeutic agents including, but not limited to, doxorubicin, daunorubicin, etoposide, cisplatin, oxaliplatin, carboplatin, gemcitabine, 5-fluorouracil, capecitabine, tegafur-uracil (UFT), dacarbazine, fenretinide, camptothecin, irinotecan, fludarabine, vinblastine, taxol, mitomycin C.

In some embodiments, the compounds of Formula I, and their pharmaceutical compositions and methods of administering them, are useful in treating various cancers when administered before, during or after patient's treatment with radiation therapy.

In accordance with an additional aspect, the present invention provides a method of inhibiting ceramidase-related activity by contacting a biological sample with a compound of Formula I, Ia, Ib as described above.

In certain embodiments the biological sample is an in vitro cell sample or an in vivo cell sample. The biological sample includes cells in culture media or lysed cells containing acid ceramidase. The biological sample includes cells present in plasma, urine, a tissue or organ sample or present in a subject. Accordingly in certain embodiments the methods of the invention can be used in medical or scientific research related to acid ceramidase and ceramidase-related activity.

VIII. PHARMACEUTICAL COMPOSITIONS

In a third aspect, the invention provides pharmaceutical compositions of compounds of Formula I, Ia, Ib.

The pharmaceutical compositions of the present invention encompass any compositions made by admixing a compound of the present invention and a pharmaceutically acceptable carrier. Such compositions are suitable for pharmaceutical use in an animal or human.

The pharmaceutical compositions of the present invention comprise a therapeutically effective amount of one or more compounds of Formula I, Ia, or Ib, or a pharmaceutically acceptable salt thereof, and a pharmaceutically acceptable carrier. A pharmaceutical composition may optionally contain other active ingredients.

The term "carrier" refers to a vehicle, excipient, diluent, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for, parenteral including subcutaneous, intramuscular, and intravenous, pulmonary, nasal, rectal, topical or oral administration. Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy. The preferred compositions include compositions suitable for oral, parenteral, topical, subcutaneous, or pulmonary, in the form of nasal or buccal inhalation, administration. The compositions may be prepared by any of the methods well-known in the art of pharmacy.

The pharmaceutical compositions may be in the form of tablets, pills, capsules, solutions, suspensions, emulsion, powders, suppository and as sustained release formulations.

If desired, tablets may be coated by standard aqueous or non aqueous techniques. In certain embodiments such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that a therapeutically effective dosage will be obtained. The active compounds can also be administered intranasally as, for example, liquid drops or spray. The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the gastrointestinal tract, the composition may be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula I, Ia, Ib or a salt thereof, and the powder of a suitable carrier and/or lubricant. The compositions for pulmonary administration can be inhaled from any suitable dry powder inhaler device known to a person skilled in the art. Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula I, Ia, Ib per dosage unit for daily administration.

In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation. When used in combination with one or more other active ingredients, the compound of the present invention and the other active ingredients may be used in lower doses than when each is used singly.

With respect to formulations with respect to any variety of routes of administration, methods and formulations for the administration of drugs are disclosed in *Remington's Pharmaceutical Sciences*, 17$^{th}$ Edition, Gennaro et al. Eds., Mack Publishing Co., 1985, and *Remington's Pharmaceutical Sciences*, Gennaro A R ed. 20$^{th}$ edition, 2000, Williams & Wilkins P A, USA, and *Remington: The Science and Practice of Pharmacy*, 21$^{st}$ Edition, Lippincott Williams & Wilkins Eds., 2005; and in *Ansel's Pharmaceutical Dosage Forms and Drug Delivery Systems*, 8$^{th}$ Edition. Lippincott Williams & Wilkins Eds, 2005, which are herein incorporated as reference.

IX. METHODS FOR TESTING COMPOUNDS ON ACID CERAMIDASE

Rat Acid Ceramidase

A lysosomal rat acid ceramidase (rAC) protein preparation was obtained from cells stably expressing rAC resuspended in 20 mM Tris HCl (pH 7.5) with 0.32 M sucrose. Samples were sonicated and centrifuged at 800×g for 15 min at 4° C. Supernatants were then centrifuged at 12,000×g for 30 min at 4° C. Pellets were re-suspended in PBS pH 7.4 and subjected to 2 freeze-thaw cycles at −80° C. The suspension was finally centrifuged at 105,000×g for 1 hr at 4° C. and the supernatant containing rAC was then used in the enzymatic assay.

r-AC protein samples were pre-incubated with various concentrations of test compounds or vehicle control in 100 mM NaH$_2$PO$_4$/citrate buffer pH 4.5, 0.1% Nonidet P-40, 3 mM DTT for 30 min at 37° C. Samples were incubated with 100 µM N-lauroyl ceramide (Nu-Chek Prep, Elysian, Minn.) at 37° for 30 min. The reaction was stopped by addition of a mixture of chloroform/methanol (2:1 vol/vol) containing 1 nmol of heptadecanoic acid (HDA; NuChek Prep). The organic phases were collected, dried under nitrogen, and analyzed by LC/MS in the negative-ion mode using heptadecanoic acid (HDA) as internal standard (m/z=199 for lauric acid, m/z=269 for HDA). HDA was eluted on an XDB Eclipse C18 column isocratically at 2.2 mL/min for 1 min with a solvent mixture of 95% methanol and 5% water, both containing 0.25% acetic acid, and 5 mM ammonium acetate. The column temperature was 50° C. Electrospray ionization (ESI) was in the negative mode, capillary voltage was 4 kV, and fragmentor voltage was 100 V. Nitrogen was used as drying gas at a flow rate of 13 L/min and at a temperature of 350° C. Nebulizer pressure was set at 60 psi. We monitored [M-H]− in the selected-ion monitoring (SIM) mode using HDA as internal standard.

Inhibition of rAC activity was calculated as a reduction of lauric acid in the samples compared to vehicle controls. Median inhibitory concentration (IC$_{50}$) values were calculated by non-linear regression analysis of log [concentration]/inhibition curves using. GraphPad Prism 5 (GraphPad Software, Inc., CA, USA) applying a standard slope curve fitting.

Human Acid Ceramidase
Recombinant Human Acid Ceramidase Expression

Human acid ceramidase (hAC) cDNA was purchased from Open Biosystem (clone ID 3923451) and subcloned in the mammalian expression vector pCDNA3.1, containing the neomycin resistance gene. The cell line HEK293 was transfected with hAC-pCDNA3.1 construct using JetPEI reagent (Polypus Transfection™, Illkirch, FR) following the manufacturer instructions. A stable cell line of hAC-overexpressing HEK293 was generated by selection with G418

(1 mg/ml) and cell clones were derived by limited dilution plating. hAC-expressing clones were analyzed by western blot.

Protein Preparation

Hek293 cells overexpressing hAC were suspended in 20 mM Tris HCl (pH 7.5) containing 0.32M sucrose, sonicated and centrifuged at 800×g for 15 min at 4° C. The supernatants were centrifuged again at 12,000×g for 30 min at 4° C. The pellets were suspended in phosphate-buffered saline (PBS) and subjected to 2 freeze-thaw cycles at −80° C. The suspensions were centrifuged at 105,000×g for 1 h at 4° C. The supernatants containing hAC were kept at −80° C. until use. Protein concentration was measured using the bicinchoninic acid (BCA) assay (Pierce).

Acid Ceramidase Activity

A hAC protein preparation (10 μg) was preincubated with inhibitors (final DMSO concentration 1%) in assay buffer (100 mM sodium phosphate, 0.1% Nonidet P-40, 150 mM NaCl, 3 mM DTT, 100 mM sodium citrate, pH 4.5) for 30 min at 37° C. Reactions were started by the addition of 50 μM N-lauroyl ceramide (Nu-Chek Prep, Elysian, Minn.) and carried on for 30 min at 37° C. Reactions were stopped by addition of a mixture of chloroform/methanol (2:1, vol/vol) containing 1 nmol 11-lauroleic acid (NuChek Prep). The organic phases were collected, dried under nitrogen and analyzed by UPLC/MS (Acquity, Waters) in the negative-ion mode monitoring the reaction product (lauric acid, m/z=199) using 11-lauroleic acid as internal standard.

Lipids were eluted on an Acquity UPLC BEH C18 column (50 mm length, 2.1 mm i.d., 1.7 μm pore size, Waters) column at 0.5 mL·min$^{-1}$ for 1.5 min with a gradient of acetonitrile ($CH_3CN$) and water, both containing 0.25% acetic acid and 5 mM ammonium acetate (70% to 100% $CH_3CN$ in 0.5 min, 100% $CH_3CN$ for 0.5 min, 70% $CH_3CN$ for 0.4 min). The column temperature was 40° C. Electrospray ionization (ESI) was in the negative mode, capillary voltage was 1 kV and cone voltage was 50 V. Nitrogen was used as drying gas at a flow rate of 500 L/h and at a temperature of 400° C.

The [M-H]$^-$ ion was monitored in the selected-ion monitoring mode (m/z values: lauric acid 199, 11-lauroleic acid 19735). Calibration curves were generated with authentic lauric acid (Nu Check Prep). Inhibition of acid ceramidase activity was calculated as reduction of lauric acid in the samples compared to vehicle controls. $IC_{50}$ values were calculated by non-linear regression analysis of log [concentration]/inhibition curves using GraphPad Prism 5 (GraphPad Software Inc., CA, USA) applying a standard slope curve fitting.

The $IC_{50}$ values of selected compounds described in the Examples are reported in the following Table 1.

TABLE 1

$IC_{50}$ values or percent inhibition, at the indicated concentration, of selected compounds of the invention on rat (rAC) and human (hAC) acid ceramidase.

| Example | rAC $IC_{50}$ (μM) | hAC $IC_{50}$ (μM) |
|---|---|---|
| 1 | 65% inhib.@ 0.3 μM | |
| 3 | 0.067 | |
| 4 | 0.01 | |
| 5 | 0.051 | 0.035 |
| 7 | 0.42 | |
| 8 | 0.147 | |
| 9 | 1.1 | |
| 10 | 5.5 | |

TABLE 1-continued $IC_{50}$ values or percent inhibition, at the indicated concentration, of selected compounds of the invention on rat (rAC) and human (hAC) acid ceramidase.

| Example | rAC $IC_{50}$ (μM) | hAC $IC_{50}$ (μM) |
|---|---|---|
| 11 | 3.4 | |
| 12 | 0.88 | |
| 13 | 1.4 | |
| 14 | 0.177 | 0.155 |
| 16 | 0.04 | |
| 18 | | 74% inhib.@1 μM |
| 19 | | 52% inhib.@1 μM |
| 20 | | 54% inhib.@1 μM |
| 21 | | 86% inhib.@1 μM |
| 22 | | 64% inhib.@1 μM |
| 23 | | 0.270 |
| 24 | | 0.014 |
| 25 | | 96% inhib.@1 μM |
| 26 | | 100% inhib.@1 μM |
| 30 | | 100% inhib.@1 μM |
| 31 | | 99% inhib.@1 μM |
| 32 | 0.007 | |
| 33 | | 100% inhib.@1 μM |
| 34 | | 99% inhib.@0.5 μM |

Methods for Screening Compounds for a Therapeutic Activity.

Lipid Extraction and Ceramide Analysis.

Lipids were extracted using a chloroform/methanol mixture (2:1 vol/vol, 3 mL) containing internal standards. The organic phases were collected, dried under nitrogen, and dissolved in methanol/chloroform (3:1 vol/vol) for LC/MS analyses.

Ceramides were analyzed by LC/MS$^n$, using a 1100-LC system (Agilent Technologies) equipped with an Ion Trap XCT and interfaced with ESI (Agilent Technologies). They were separated on a Poroshell 300 SB C18 column (2.1×75 mm i.d., 5 μm; Agilent Technologies) maintained at 30° C. A linear gradient of methanol in water containing 5 mM ammonium acetate and 0.25% acetic acid (from 80% to 100% of methanol in 3 man) was applied at a flow rate of 1 mL/min. Detection was in the positive mode, capillary voltage was 4.5 kV, skimmer voltage at −40 V, and capillary exit −151 V. Nitrogen was used as drying gas at a flow rate of 10 L/min, temperature of 350° C., and nebulizer pressure of 80 psi. Helium was used as collision gas.

Tissue-derived ceramides were identified by comparison of their LC retention times and MS$^n$ fragmentation patterns with those of authentic standards (Avanti Polar Lipids). Extracted ion chromatograms were used to quantify myristoyl ceramide (C140, m/z 510.5>492.5>264.3), palmitoyl ceramide (C16:0, m/z 538.5>520.3>264.3), stearoyl ceramide (C18:0 m/z 566.5>548.3>264.3), lignoceroylceramide (C24:0 m/z 650.5>632.3>264.3), nervonoylceramide (C24:1 m/z 648.5>630.3>264.3) and using lauroyl ceramide standard (m/z 482.5>464.5>264.3). Detection and analysis were controlled by Agilent/Bruker Daltonics software version 5.2. MS spectra were processed using MS Processor from Advanced Chemistry Development.

Figure 1:
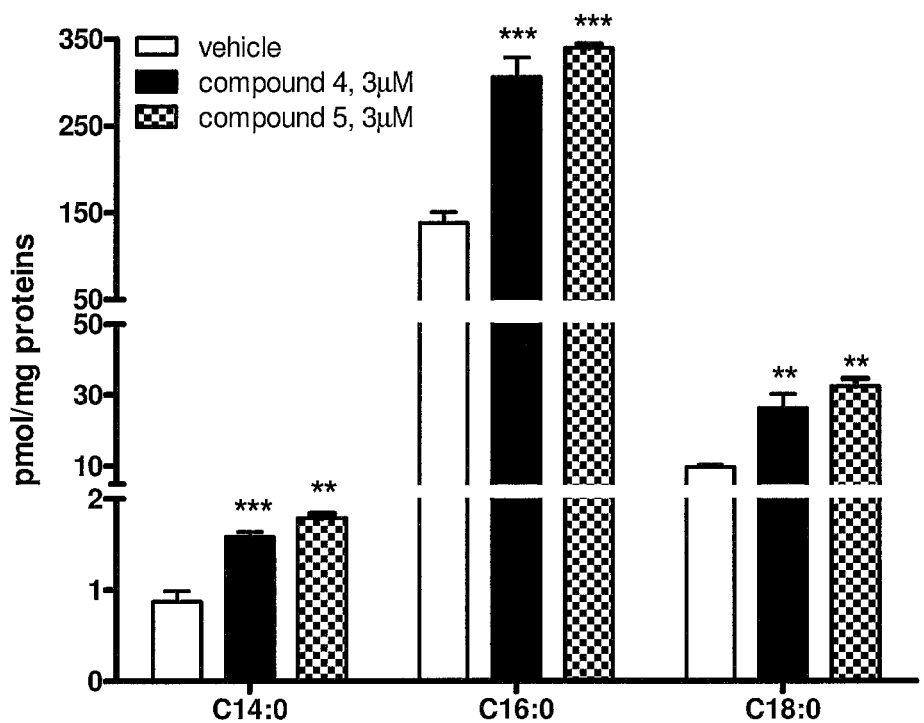
FIG. 1 shows a bar graph illustrating the effect of compound 4, compound 5 or vehicle (0.1% dimethylsulfoxide in Dulbecco's Modified Eagle's Medium, DMEM) on ceramide levels in the human colon adenocarcinoma cell line SW403. Treatment of SW403 cells, for 3 hr, with compounds 4 and 5, at the concentration of 3 μM, increased the levels of the most abundant endogenous ceramide species, C14:0, C16:0 and C18:0. Results are expressed as mean±SEM (n=3-6), with each assay performed in duplicate. *$p<0.001$, $p<0.01$ vs. vehicle, one-way ANOVA.

Compounds 4 and 5 increased the levels of C14:0, C16:0 and C18:0 ceramide in the human colon adenocarcinoma cell line SW403, as depicted in FIG. 1. Cells were treated for 3 hrs with compound 4 and compound 5, at the concentration of 3 μM, then ceramide levels were measured.

Cell Viability and Proliferation Assays.

Cell viability can be defined as the number of living cells in a sample. There are many well described and widely used methods to evaluate cell viability such as trypan blue dye exclusion, MTT reduction or crystal violet [for a review, see Stoddart M J, *Cell viability assays: introduction, Methods in Molecular Biology,* 2011, Vol. 740].

Cells were seeded in 12- or 96-well plates in complete medium 24 hrs before treatment and then incubated for 24 hrs (single treatment) or 72 hrs (multiple treatments) with different drug concentrations in media without serum. Cell viability was then evaluated.

The trypan blue exclusion assay is based on the principle that viable cells have intact cell membrane and can therefore exclude the trypan blue dye. Cell viability was measured after 24 hrs incubation with the drug. Cells were harvested, centrifuged at 1200 rpm for 10 min and pellets re-suspended in PBS. To evaluate viability, cells were diluted 1:1 with 0.4% trypan blue dye (Sigma), incubated for 1 min and white (viable) cells were counted with a hemacytometer.

Alternatively, cell viability was assessed measuring mitochondrial functionality by the MIT assay, which is based on the reduction of the soluble tetrazolium salt MTT [(3-(4,5-dimethylthiazol-2-yl)-2,5-diphenyltetrazolium bromide] into insoluble formazan by mitochondria. Briefly, after treatment, cells were washed with PBS and incubated with 0.5 mg/ml, MTT for 2 hrs at room temperature, MTT reduction was quantified by absorbance at 570 nm using a UV-visible plate reader.

Finally, crystal violet assay was used to evaluate cells morphology and proliferation: at specific time points (every 24 hrs for 7 days) media were removed, cells were washed once with PBS and fixed with 4% formaldehyde for 10 min. Cells were stained with 0.4% crystal violet in 50% MeOH for 20 min and extensively washed with water to remove excess dye. Crystal violet was dissolved in DMSO. The absorbance of the dissolved dye, corresponding to the number of viable cells, was measured in a UV-visible plate reader at 570 nm.

Isobolographic Analysis.

Interaction between drugs was assessed by isobolographic analysis, based on the concept of dose-equivalence which follows from the dose effect curves of the individual drugs (Tallarida R I, *Interactions between drugs and occupied receptors. Pharmacol. Ther.* 2007, 113, 197-209; Tallarida R J, Raffa R B, *The application of drug dose equivalence in the quantitative analysis of receptor occupation and drug combinations. Pharmacol. Ther.* 2010; 127, 165-174). Specifically, the individual drugs' potency and efficacy allow calculating the expected effect of a combination of the two drugs.

In the experiment of combined treatment, isobolograms were constructed by plotting on vertical and horizontal axes the $ED_{50}$ data of the single drugs measured by trypan blue assay after subcronic treatment for 72 hrs. The straight line with axial intercepts represents the isobole of additivity and allows calculating the theoretical additive dose. Synergism is indicated by an observed pair (x, y) that plots below the isobole for the specified effect, whereas sub-additivity is indicated when an observed pair (x, y) plots above the isobole.

Figure 2:
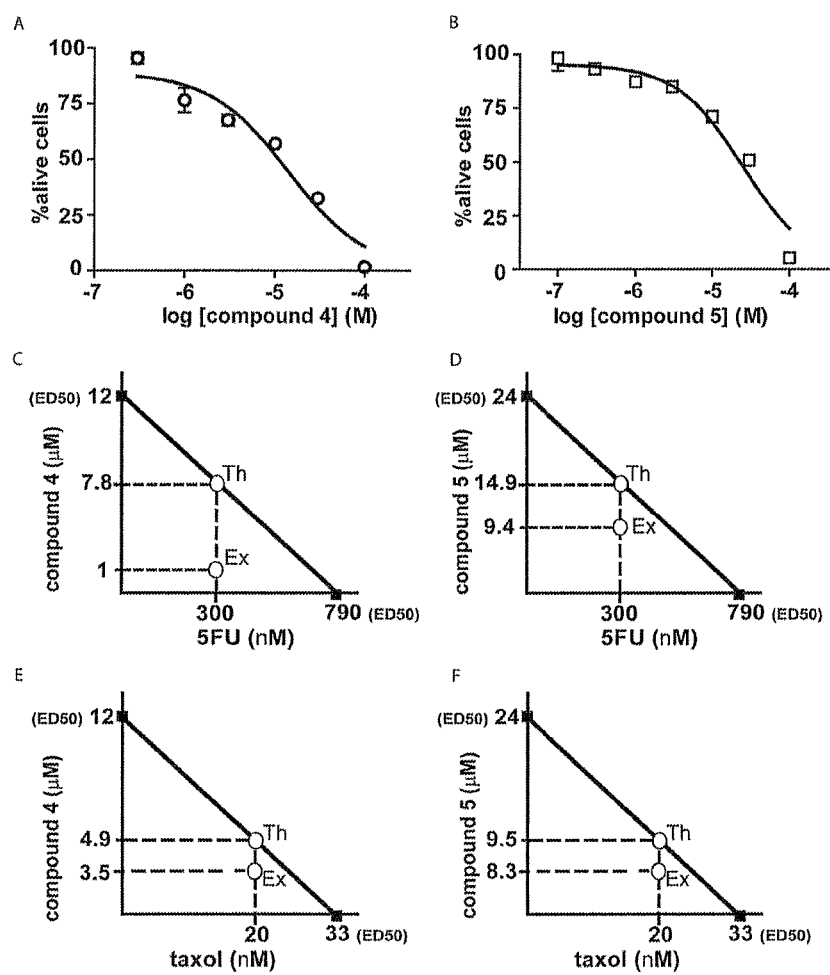
FIG. 2 shows six graphs illustrating the effects of compound 4 and compound 6 on SW403 cell viability, and synergism with antineoplastic agents, 5-fluorouracil (5FU) and taxol (trypan blue assay).

Compounds 4 and 5 caused a reduction of the viability of the human colon adenocarcinoma cell line SW403, as measured by the trypan blue assay (FIGS. 2A and 2B) or by the MTT assay (FIG. 3). FIG. 3 shows that sub-chronic treatment (72 hrs) of SW403 cells with 5-fluorouracil (5FU, 300 nM), compound 4 (30 µM, upper panel), and compound 5 (30 µM, lower panel) reduced cell viability as measured by the MTT assay. Compounds 4 and 5 showed a synergistic effect with 5FU in reducing cell viability.

Compounds 4 and 5 also showed a synergistic effect with two distinct anti-neoplastic agents, 5-fluorouracil (5FU, FIG. 2 and FIG. 3) and taxol (FIG. 2) in reducing the viability of SW403 cells. Isobolographic analysis of data obtained after prolonged treatment of SW403 cells with compound 4 or compound 5 and 5-FU are reported in FIGS. 2C and 2D. Isobolograms were constructed with median effective dose ($ED_{50}$) data measured by trypan blue assay. The theoretical doses ($T_h$) of compound 4 or compound 5 to be used with 300 nM 5FU to obtain an additive effect were 7.8 µM and 14.9 µM, respectively, higher than the experimental values ($E_x$). The effect was synergistic. Results are expressed as mean±SEM (n=3), with each experiment performed twice.

Isobolographic analysis of data obtained after prolonged treatment of SW403 cells with compound 4 or compound 5 and taxol are reported in FIGS. 2E and 2F. Isobolograms were constructed with $ED_{50}$ data measured by trypan blue assay. The theoretical doses ($T_h$) of compound 4 or compound 5 to be used with 20 nM taxol to obtain an additive effect were 4.9 µM and 9.5 µM, respectively, higher than the experimental values ($E_x$). The effect was synergistic. Results are expressed as mean±SEM (n=3), with each experiment performed twice.

Statistics.

GraphPad Prism software (GraphPad Software, Inc., USA) was used for statistical analysis. Data were analyzed using the Student's t-test or one-way ANOVA followed by Bonferroni post hoc test for multiple comparisons. Two-way ANOVA was used to compare the means of data with two independent variables. Differences between groups were considered statistically significant at values of p<0.05. Results are expressed as mean±SEM.

General Purification and Analytical Methods

UPLC-MS analyses were run on a Waters ACQUITY UPLC-MS instrument consisting of a SQD Single Quadrupole Mass Spectrometer equipped with an electrospray ionization interface and a photodiode array detector. The analyses were performed on an ACQUITY UPLC BEH C18 column (50×2.1 mmID, particle sin 1.7 µm) with a VanGuard BEH C18 pre-column (5×2.1 mmID, particle size 1.7 µm). The mobile phases were 10 mM ammonium acetate at pH 5 adjusted with acetic acid (A) and 10 mM ammonium acetate in acetonitrile-water (95:5) at pH 5 (B). Electrospray ionization in positive and negative mode was used in the mass scan range 100-500 Da.

Automated column chromatography purification was done using a Teledyne ISCO apparatus (CombiFlash® Rf) with, normal phase pre-packed silica gel columns of different sizes (from 4 g to 40 g). Typical silica gel column chromatography is intended as a purification performed using normal glass columns filled with Merck silica gel 60 (230-400 mesh) as stationary phase. In both cases, mixtures of increasing polarity of cyclohexane or petroleum ether and ethyl acetate were used as eluents.

Flash column chromatography was performed manually on pre-packed silica cartridges (2 g or 5 g) from Biotage or on glass columns using Merck silica gel 60 (230-400 mesh) as stationary phase.

Purifications by preparative HPLC-MS were run on a Waters Autopurification system consisting of a 3100 Single Quadropole Mass Spectrometer equipped with an electrospray ionization interface and a 2998 Photodiode Array Detector. The HPLC system included a 2747 Sample Manager, 2545 Binary Gradient Module, System XBridge™ Prep $C_{18}$ OBD column (100×19 mmID, particle size 5 µm) with a XBridge™ Prep $C_{18}$ (10×19 mmID, particle size 5

μm) Guard Cartridge. The mobile phases were either 1) water and acetonitrile (B) or 2) 10 mM ammonium acetate at pH 5 adjusted with acetic acid (A) and 10 mM ammonium acetate in acetonitrile-water (95:5) at pH 5 (B). Electrospray ionization in positive and negative mode was used in the mass scan range 100-500 Da.

Flow hydrogenation reactions were performed on the H-Cube apparatus, from Thalesnano Nanotechnology Inc. using cartridges of various commercial pre-packed heterogeneous catalysts. Small format (s-cart) cartridges were adopted (30×4 mm, containing ~140 mg catalyst). Microwave heating was performed using. Explorer®-48 positions instrument (CEM). NMR experiments were run on a Bruker Avance III 400 system (400.13 MHz for $^1$H, and 100.62 MHz for $^{13}$C), equipped with a BBI inverse probe and Z-gradients. Unless indicated, spectra were acquired at 300 K, using deuterated dimethylsulfoxyde (DMSO-$d_6$) and deuterated chloroform (CDCl$_3$) as solvents.

With the aim of better illustrating the present invention, without limiting it, the examples reported in the following Table 2 are provided.

TABLE 2

Examples of compounds of the invention

| Example | Structure | Formula | Name |
|---|---|---|---|
| 1 | 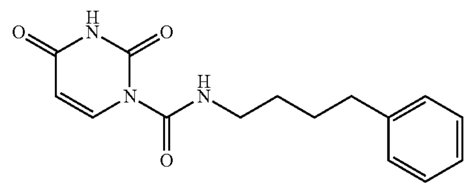 [SMILES: O=C(NCCCCc1ccccc1)n1ccc(=O)[nH]c1=O] | $C_{15}H_{17}N_3O_3$ | 2,4-dioxo-N-(4-phenylbutyl)pyrimidine-1-carboxamide |
| 2 | 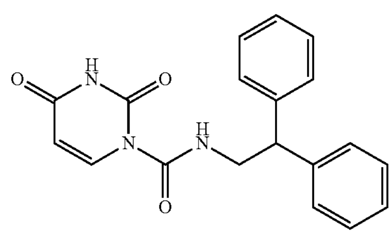 [SMILES: O=C(NCC(c1ccccc1)c1ccccc1)n1ccc(=O)[nH]c1=O] | $C_{19}H_{17}N_3O_3$ | N-(2,2diphenylethyl)-2,4-dioxopyrimidine-1-carboxamide |
| 3 | 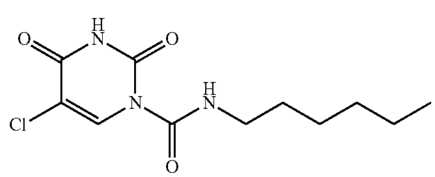 [SMILES: CCCCCCNC(=O)n1cc(Cl)c(=O)[nH]c1=O] | $C_{11}H_{16}ClN_3O_3$ | 5-chloro-N-hexyl-2,4-dioxo-pyrimidine-1-carboxamide |
| 4 | 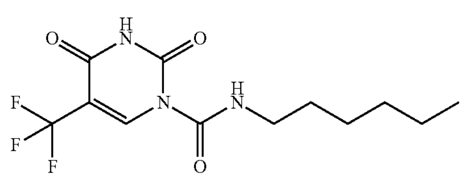 [SMILES: CCCCCCNC(=O)n1cc(C(F)(F)F)c(=O)[nH]c1=O] | $C_{12}H_{16}F_3N_3O_3$ | N-hexyl-2,4-dioxo-5-(trifluoromethyl)pyrimidine-1-carboxamide |
| 5 | 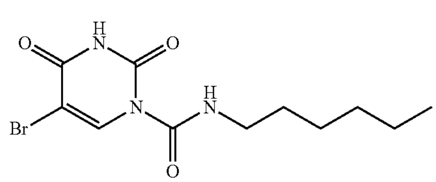 [SMILES: CCCCCCNC(=O)n1cc(Br)c(=O)[nH]c1=O] | $C_{11}H_{16}BrN_3O_3$ | 5-bromo-N-hexyl-2,4-dioxo-pyrimidine-1-carboxamide |
| 6 | 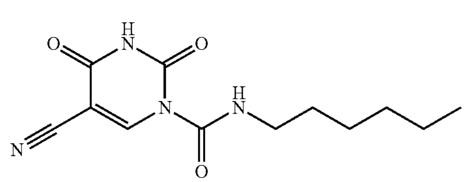 [SMILES: CCCCCCNC(=O)n1cc(C#N)c(=O)[nH]c1=O] | $C_{12}H_{16}N_4O_3$ | 5-cyano-N-hexyl-2,4-dioxo-pyrimidine-1-carboxamide |

TABLE 2-continued

Examples of compounds of the invention

| Example | Structure | Formula | Name |
| --- | --- | --- | --- |
| 7 | 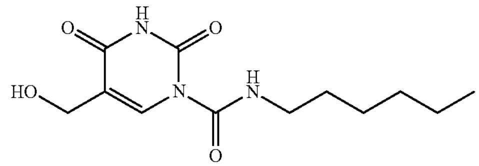 [SMILES: CCCCCCNC(=O)n1cc(CO)c(=O)[nH]c1=O] | $C_{12}H_{19}N_3O_4$ | N-hexyl-5-(hydroxymethyl)-2,4-dioxo-pyrimidine-1-carboxamide |
| 8 | 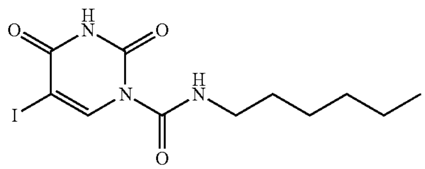 [SMILES: CCCCCCNC(=O)n1cc(I)c(=O)[nH]c1=O] | $C_{11}H_{16}IN_3O_3$ | N-hexyl-5-iodo-2,4-dioxo-pyrimidine-1-carboxamide |
| 9 | 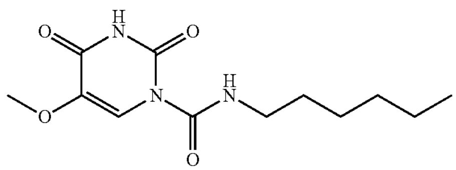 [SMILES: CCCCCCNC(=O)n1cc(OC)c(=O)[nH]c1=O] | $C_{12}H_{19}N_3O_4$ | N-hexyl-5-methoxy-2,4-dioxo-pyrimidine-1-carboxamide |
| 10 | 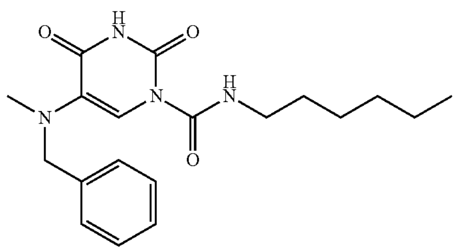 [SMILES: CCCCCCNC(=O)n1cc(N(C)Cc2ccccc2)c(=O)[nH]c1=O] | $C_{19}H_{26}N_4O_3$ | 5-(benzyl(methyl)amino)-N-hexyl-2,4-dioxo-pyrimidine-1-carboxamide |
| 11 | 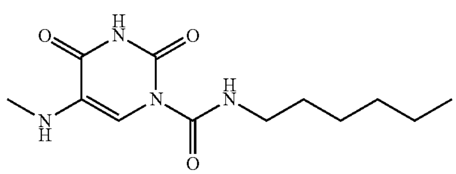 [SMILES: CCCCCCNC(=O)n1cc(NC)c(=O)[nH]c1=O] | $C_{12}H_{20}N_4O_3$ | N-hexyl-5-methylamino-2,4-dioxo-pyrimidine-1-carboxamide |
| 12 | 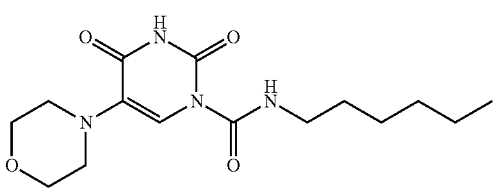 [SMILES: CCCCCCNC(=O)n1cc(N2CCOCC2)c(=O)[nH]c1=O] | $C_{15}H_{24}N_4O_4$ | N-hexyl-5-morpholino-2,4-dioxo-pyrimidine-1-carboxamide |
| 13 | 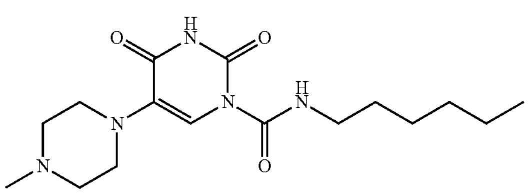 [SMILES: CCCCCCNC(=O)n1cc(N2CCN(C)CC2)c(=O)[nH]c1=O] | $C_{16}H_{27}N_5O_3$ | N-hexyl-5-(4-methylpiperazin-1-yl)-2,4-dioxo-pyrimidine-1-carboxamide |
| 14 | 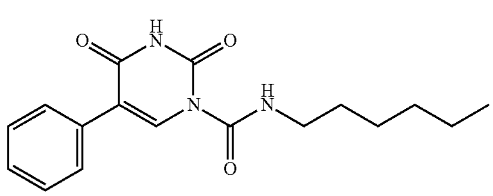 [SMILES: CCCCCCNC(=O)n1cc(-c2ccccc2)c(=O)[nH]c1=O] | $C_{17}H_{21}N_3O_3$ | N-hexyl-2,4-dioxo-5-phenyl-pyrimidine-1-carboxamide |

TABLE 2-continued

| Example | Structure | Formula | Name |
|---|---|---|---|
| 15 | 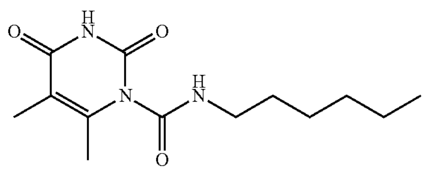 [SMILES: CCCCCCNC(=O)n1c(C)c(C)c(=O)[nH]c1=O] | $C_{13}H_{21}N_3O_3$ | N-hexyl-5,6-dimethyl-2,4-dioxo-pyrimidine-1-carboxamide |
| 16 | 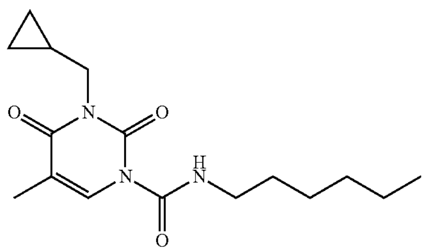 [SMILES: CCCCCCNC(=O)n1cc(C)c(=O)n(CC2CC2)c1=O] | $C_{16}H_{25}N_3O_3$ | 3(cyclopropylmethyl) N-hexyl-5-methyl-2,4-dioxopyrimidine-1-carboxamide |
| 17 | 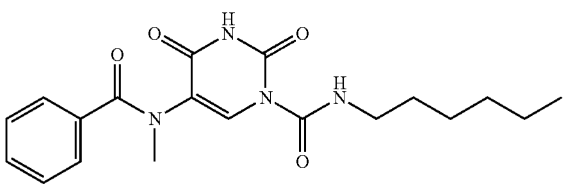 [SMILES: CCCCCCNC(=O)n1cc(N(C)C(=O)c2ccccc2)c(=O)[nH]c1=O] | $C_{19}H_{24}N_4O_4$ | 5-[benzoyl(methyl)amino]-N-hexyl-2,4-dioxo-pyrimidine-1-carboxamide |
| 18 | 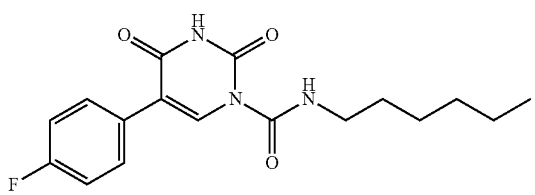 [SMILES: CCCCCCNC(=O)n1cc(-c2ccc(F)cc2)c(=O)[nH]c1=O] | $C_{17}H_{20}FN_3O_3$ | 5-(4-fluorophenyl)-N-hexyl-2,4-dioxo-pyrimidine-1-carboxamide |
| 19 | 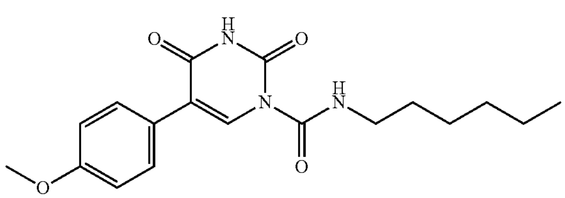 [SMILES: CCCCCCNC(=O)n1cc(-c2ccc(OC)cc2)c(=O)[nH]c1=O] | $C_{18}H_{23}N_3O_4$ | N-hexyl-5-(4-methoxyphenyl)-2,4-dioxo-pyrimidine-1-carboxamide |
| 20 | 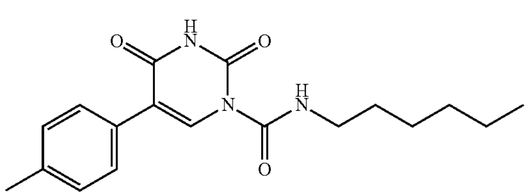 [SMILES: CCCCCCNC(=O)n1cc(-c2ccc(C)cc2)c(=O)[nH]c1=O] | $C_{18}H_{23}N_3O_3$ | N-hexyl-2,4-dioxo-5-(p-tolyl)pyrimidine-1-carboxamide |
| 21 | 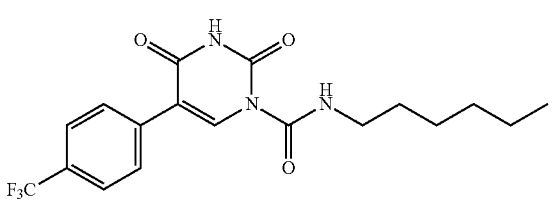 [SMILES: CCCCCCNC(=O)n1cc(-c2ccc(C(F)(F)F)cc2)c(=O)[nH]c1=O] | $C_{18}H_{20}F_3N_3O_3$ | N-hexyl-2,4-dioxo-5-[4-(trifluoromethyl)phenyl]pyrimidine-1-carboxamide |

TABLE 2-continued

Examples of compounds of the invention

| Example | Structure | Formula | Name |
|---|---|---|---|
| 22 | 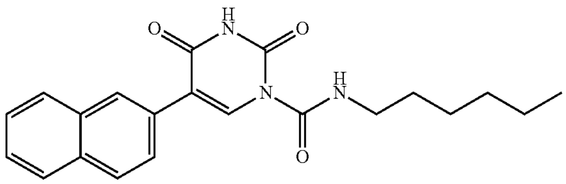 [SMILES: CCCCCCNC(=O)n1cc(-c2ccc3ccccc3c2)c(=O)[nH]c1=O] | $C_{21}H_{23}N_3O_3$ | N-hexyl-5-(2-naphthyl)-2,4-dioxo-pyrimidine-1-carboxamide |
| 23 | 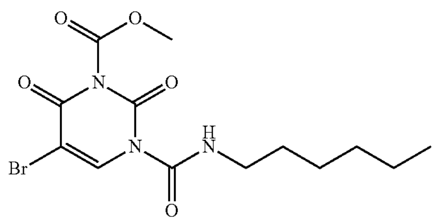 [SMILES: CCCCCCNC(=O)n1cc(Br)c(=O)n(C(=O)OC)c1=O] | $C_{13}H_{18}BrN_3O_5$ | Methyl 5-bromo-3-(hexylcarbamoyl)-2,6-dioxo-pyrimidine-1-carboxylate |
| 24 | 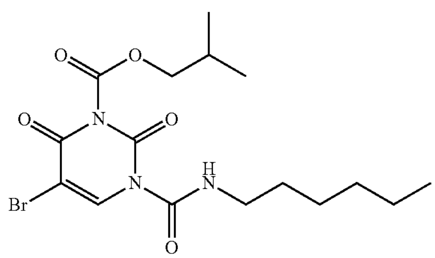 [SMILES: CCCCCCNC(=O)n1cc(Br)c(=O)n(C(=O)OCC(C)C)c1=O] | $C_{16}H_{24}BrN_3O_5$ | Isobutyl 5-bromo-3-(hexylcarbamoyl)-2,6-dioxo-pyrimidine-1-carboxylate |
| 25 | 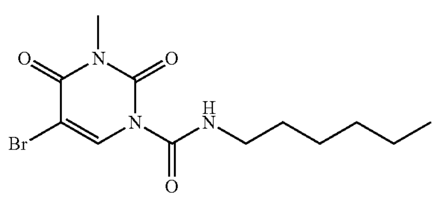 [SMILES: CCCCCCNC(=O)n1cc(Br)c(=O)n(C)c1=O] | $C_{12}H_{18}BrN_3O_3$ | 5-Bromo-N-hexyl-3-methyl-2,4-dioxo-pyrimidine-1-carboxamide |
| 26 | 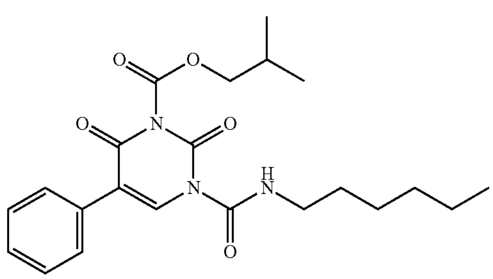 [SMILES: CCCCCCNC(=O)n1cc(-c2ccccc2)c(=O)n(C(=O)OCC(C)C)c1=O] | $C_{22}H_{29}N_3O_5$ | Isobutyl 3-(hexylcarbamoyl)-2,6-dioxo-5-phenyl-pyrimidine-1-carboxylate |
| 27 | 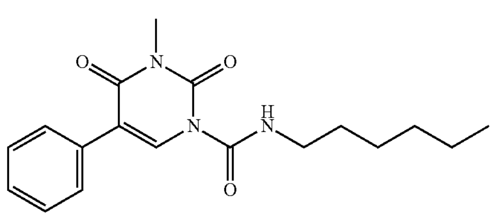 [SMILES: CCCCCCNC(=O)n1cc(-c2ccccc2)c(=O)n(C)c1=O] | $C_{18}H_{23}N_3O_3$ | N-Hexyl-3-methyl-2,4-dioxo-5-phenyl-pyrimidine-1-carboxamide |
| 28 | 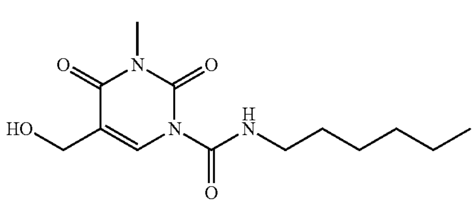 [SMILES: CCCCCCNC(=O)n1cc(CO)c(=O)n(C)c1=O] | $C_{13}H_{21}N_3O_4$ | N-hexyl-5-(hydroxymethyl)-3-methyl-2,4-dioxo-pyrimidine-1-carboxamide |

TABLE 2-continued

Examples of compounds of the invention

| Example | Structure | Formula | Name |
|---------|-----------|---------|------|
| 29 | 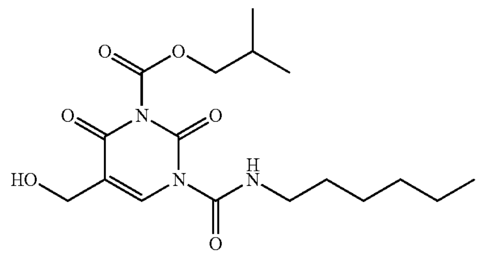 [SMILES: CCCCCCNC(=O)n1cc(CO)c(=O)n(C(=O)OCC(C)C)c1=O] | $C_{17}H_{27}N_3O_6$ | isobutyl 3-(hexylcarbamoyl)-5-(hydroxymethyl)-2,6-dioxo-pyrimidine-1-carboxylate |
| 30 | 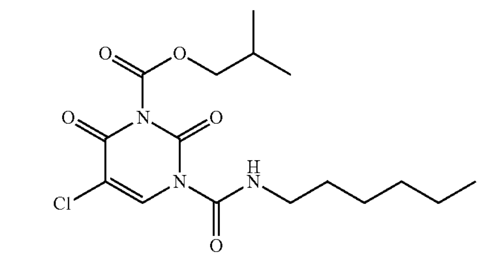 [SMILES: CCCCCCNC(=O)n1cc(Cl)c(=O)n(C(=O)OCC(C)C)c1=O] | $C_{16}H_{24}ClN_3O_5$ | isobutyl 5-chloro-3-(hexylcarbamoyl)-2,6-dioxo-pyrimidine-1-carboxylate |
| 31 | 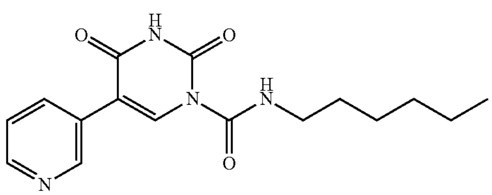 [SMILES: CCCCCCNC(=O)n1cc(-c2cccnc2)c(=O)[nH]c1=O] | $C_{16}H_{20}N_4O_3$ | N-hexyl-2,4-dioxo-5-(3-pyridyl)pyrimidine-1-carboxamide |
| 32 | 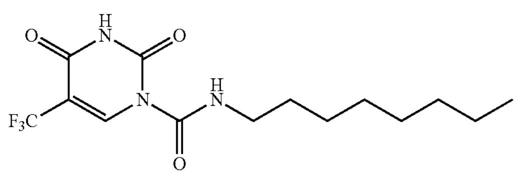 [SMILES: CCCCCCCCNC(=O)n1cc(C(F)(F)F)c(=O)[nH]c1=O] | $C_{14}H_{20}F_3N_3O_3$ | N-octyl-2,4-dioxo-5-(trifluoromethyl)pyrimidine-1-carboxamide |
| 33 | 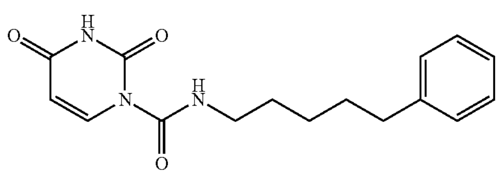 [SMILES: O=C(NCCCCCc1ccccc1)n1ccc(=O)[nH]c1=O] | $C_{16}H_{19}N_3O_3$ | 2,4-dioxo-N-(5-phenylpentyl)pyrimidine-1-carboxamide |
| 34 | 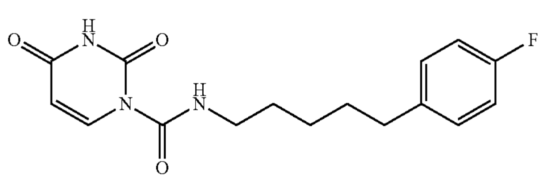 [SMILES: O=C(NCCCCCc1ccc(F)cc1)n1ccc(=O)[nH]c1=O] | $C_{16}H_{18}FN_3O_3$ | N-[5-(4-fluorophenyl)pentyl]-2,4-dioxo-pyrimidine-1-carboxamide |
| 35 | 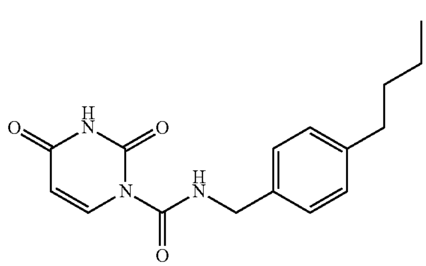 [SMILES: CCCCc1ccc(CNC(=O)n2ccc(=O)[nH]c2=O)cc1] | $C_{16}H_{19}N_3O_3$ | N-[(4-butylphenyl)methyl]-2,4-dioxo-pyrimidine-1-carboxamide |

TABLE 2-continued

Examples of compounds of the invention

| Example | Structure | Formula | Name |
|---|---|---|---|
| 36 | AND Enantiomer 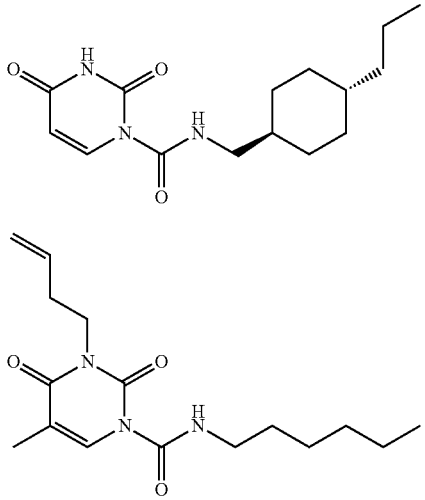 | $C_{15}H_{23}N_3O_3$ | N-[(4-propylcyclohexyl)methyl]-2,4-dioxo-pyrimidine-1-carboxamide |
| 37 | 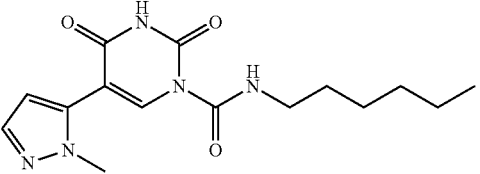 [SMILES: CCCCCCNC(=O)n1cc(-c2ccnn2C)c(=O)[nH]c1=O] | $C_{16}H_{25}N_3O_3$ | 3-but-3-enyl-N-hexyl-5-methyl-2,4-dioxo-pyrimidine-1-carboxamide |
| 38 | 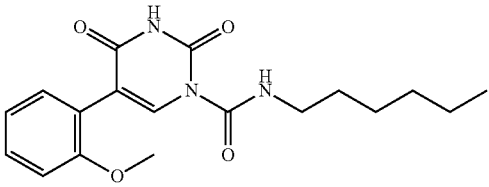 [SMILES: CCCCCCNC(=O)n1cc(-c2ccccc2OC)c(=O)[nH]c1=O] | $C_{15}H_{21}N_5O_3$ | N-hexyl-5-(2-methylpyrazol-3-yl)-2,4-dioxo-pyrimidine-1-carboxamide |
| 39 | 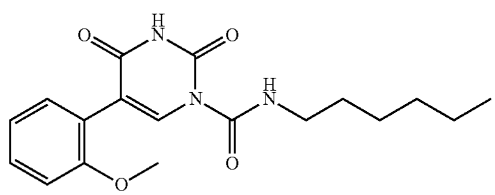 | $C_{18}H_{23}N_3O_4$ | N-hexyl-5-(2-methoxyphenyl)-2,4-dioxo-pyrimidine-1-carboxamide |

The compounds reported in Table 2 were synthesized as described below.

EXAMPLES

The following Examples provide illustrative embodiments. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

In the procedure that follows, after the starting materials, reference to a description is typically provided. The starting materials may not necessarily have been prepared from the description referred to.

Solvents and reagents used in the following examples were commercially available from various suppliers and were used without further purification. For simplicity, solvents and reagents were indicated as follows.

Acetonitrile (MeCN), ammonium chloride ($NH_4Cl$), 4-(dimethylamino)-pyridine(DMAP), N,N-di-isopropylethylamine (DIPEA), Diisopropyl azodicarboxylate (DIAD), N,N-dimethylformamide (DMF), dimethylsulfoxyde (DMSO), ethyl acetate (EtOAc), hydrochloric acid (HCl), iodine ($I_2$), lithium aluminum hydride ($LiAlH_4$), methanol (MeOH), silica (SI), sodium bicarbonate ($NaHCO_3$), sodium hydride (NaH), sodium hydroxide (NaOH), sodium sulfate ($Na_2SO_4$), tetrahydrofuran (THF), trifluoroacetic acid (TFA).

Example 1

2,4-dioxo-N-(4-phenylbutyl)pyrimidine-1-carboxamide

Uracil (0.10 g, 0.89 mmol) was dissolved in dry pyridine (4.4 mL). DMAP (0.12 g, 0.96 mmol) was added and the reaction mixture was stirred under nitrogen atmosphere at room temperature for 30 min. 4-Phenyl butyl isocyanate (0.27 mL, 1.60 mmol, 1.8 equiv) was then added and the resulting mixture was stirred for 12 hrs. The solvent was evaporated under reduced pressure and the crude was purified by column chromatography using a Teledyne ISCO apparatus (cyclohexane:EtOAc from 50:50 to 30:70) to afford the title compound (0.10 g, 59%) as white powder. $^1$H NMR (400 MHz, $CDCl_3$): δ 1.59-1.82 (m, 4H), 2.66 (t, J=7.2 Hz, 2H), 3.29-3.60 (m, 2H), 5.89 (d, J=8.5 Hz, 1H), 7.11-7.22 (m, 3H), 723-734 (m, 2H), 8.41 (d, J=8, 5 Hz, 2H), 8.66 (s, 1H), 9.06 (t, J=5.7 Hz, 1H). $^{13}$C NMR (101 MHz, CDCl$_3$): δ 28.69, 28.92, 35.56, 41.23, 77.16, 104.01, 126.06, 128.53, 139.08, 141.95, 149.84, 151.51, 162.30 MS (ESI) m/z: 310 [M-N]⁻.

Example 2

N-(2,2-diphenylethyl)-2,4-dioxo-pyrimidine-1-carboxamide

The title compound was obtained according to the procedure described for the synthesis of Example 1, starting from uracil (0.37 g, 3.34 mmol); 1.3 equivalents of 2,2-diphenylethyl isocyanate were used herein. The crude was taken up in dichloromethane; the title compound precipitated and was filtered off. The title compound (0.85 g, 76%) was isolated as white powder. $^1$H NMR (400 MHz, DMSO-d$_6$): δ 3.97 (dd, J=8, 0, 5.5 Hz, 2H), 4.32 (t, J=7.9 Hz, 1H), 5.78 (d, J=8.4 Hz, 1H), 7.17-7.25 (m, 2H), 7.27-7.39 (m, 8H), 8.19 (d, J=8.4 Hz, 1H), 9.20 (t, J=5.5 Hz, 1H), 11.66 (s, 1H). $^{13}$C NMR (101 MHz, DMSO-d$_6$): δ 44.93, 50.61, 103.98, 127.09, 127.18, 128.60, 138.79, 142.58, 142.91 150.27, 151.93, 161.03. MS (ESI) m/z: 334 [M-H]⁻.

Example 3

5-Chloro-N-hexyl-2,4-dioxo-pyrimidine-1-carboxamide

The title compound was obtained according to the procedure described for the synthesis of Example 1, starting from 5-chlorouracil (0.10 g, 0.68 mmol); 1.2 equivalents of hexyl isocyanate were used herein. The crude was purified by column chromatography using a Teledyne ISCO apparatus (petroleum ether:EtOAc from 70:30 to 50:50) to afford the title compound (0.06 g, 31%) as white powder. $^1$H NMR (400 MHz, DMSO-d$_6$): δ 0.86 (t, J=6.8 Hz, 3H), 1.21-1.35 (m, 6H), 1.46-1.54 (m, 2H), 3.24-3.29 (m, 2H), 8.41 (s, 1H), 9.07 (t, J=5.3 Hz, 1H), 12.24 (s, 1H). $^{13}$C NMR (101 MHz, DMSO-d$_6$) δ 13.85, 21.97, 25.81, 28.57, 30.82, 40.55, 109.55, 135.56, 149.21, 150.61, 158.78. MS (ESI) m/z: 272 [M-H]⁻.

Example 4

N-hexyl-2,4-dioxo-5-(trifluoromethyl)pyrimidine-1-carboxamide

The title compound was obtained according to the procedure described for the synthesis of Example 1, starting from 5-(trifluoromethyl)uracil (0.20 g, 1.11 mmol). The crude was purified by column chromatography using SI (5 g) cartridge (petroleum ether:EtOAc 90:10) to afford the title compound (0.12 g, 34%) as white powder. $^1$H NMR (400 MHz, CDCl$_3$): δ 0.90 (t, J=6, 7 Hz, 3H), 1.16-1.49 (m, 6H), 1.49-1.75 (m, 2H), 3.41 (dt, J=5.7, 7.1 Hz, 2H), 748 (s, 1H), 8.93 (m, 2H). $^{13}$C NMR (101 MHz, CDCl$_3$): δ 14.14, 22.56, 26.56, 31.33, 31.41, 41.71, 108.21, 121.27 (q, J=270.7 Hz), 140.13, 148.48, 150.25, 157.41. MS (ESI) m/z: 306 [M-H]⁻.

Example 5

5-bromo-N-hexyl-2,4-dioxo-pyrimidine-1-carboxamide

The title compound was obtained according to the procedure described for the synthesis of compound of Example 1, starting from 5-bromouracil (0.03 g, 1.57 mmol). The crude was purified by column chromatography using a Teledyne ISCO apparatus (petroleum ether:EtOAc from 60:40 to 100% EtOAc) to afford the title compound (0.31 g, 62%) as white powder. $^1$H NMR (400 MHz, DMSO-d$_6$): δ 0.87 (t, J=6.5 Hz, 3H), 1.24-1.32 (m, 6H), 1.40-1.61 (m, 2H), 3.26 (td, J=7.0, 5.7 Hz, 2H), 8.47 (s, 1H), 9.07 (t, J=5.7 Hz, 1H), 12.20 (s, 1H). $^{13}$C NMR (101 MHz, CDCl$_3$): δ 14.12, 22.65, 26.61, 29.23, 31.49, 41.63, 100.15, 138.41, 148.91, 150.70, 158.08. MS (ESI) m/z: 317 [M-H]⁻.

Example 6

5-cyano-N-hexyl-2,4-dioxo-pyrimidine-1-carboxamide

5-Cyanouracil (0.10 g, 0.73 mmol) was dissolved in dry pyridine (5.0 mL) and hexyl isocyanate (0.08 mL, 1.10 mmol) was added. The mixture was heated under microwave irradiation to 100° C. for 10 min and then was poured into water (50 mL). The product was extracted with dichloromethane (2×50 mL), the combined organic layers were dried over Na$_2$SO$_2$ and the solvent was concentrated under reduced pressure. The crude was purified by column chromatography using SI (2 g) cartridge (dichloromethane) and subsequently washed with warm heptane to afford the title compound (0.03 g, 16%) as white powder. $^1$H NMR (400 MHz, DMSO-d$_6$): δ 0.86-0.96 (m, 3H), 1.29-1.41 (m, 6H), 1.57-1.70 (m, 2H), 3.44 (q, J=6.4, 2H), 5.01 (s, 1H), 8.85 (br s, 1H), 9.05 (s, 1H). MS (ESI) m/z: 263 [M-H]⁻.

Example 7

N-hexyl-6-(hydroxymethyl)-2,4-dioxo-pyrimidine-1-carboxamide

The title compound was obtained according to the procedure described for the synthesis of Example 6, starting from 5-(hydroxymethyl)uracil (0.07 g, 0.49 mmol) and 1.1 equiv di hexyl isocyanate. The crude was purified by silica gel column chromatography (dichloromethane:acetone 60:40) to afford the title compound (0.04 g, 27%) as white powder. $^1$H NMR (400 MHz, CDCl$_3$): δ 0.90 (t, J=6.9 Hz, 3H), 1.31-1.39 (m, 6H), 1.56-1.64 (m, 2H), 2.40 (t, J=6.5 Hz, 1H), 3.39 (td, J=7.1, 5.6 Hz, 2H), 4.48 (d, J=6.6 Hz, 2H), 8.33 (s, 1H), 8.45 (s, 1H), 9.00 (s, 1H). $^{13}$C NMR (101 MHz, CDCl$_3$): δ 14.13, 22.66, 26.63, 29.27, 31.51, 41.47, 58.82, 115.26, 136.19, 149.74, 151.09, 162.49. MS (ESI) m/z: 292 [M-Na]⁺, 308 [M-K]⁺. MS (ESI) m/z: 268 [M-H]⁻.

Example 8

N-hexyl-6-iodo-2,4-dioxopyrimidine-1-carboxamide

The title compound was obtained according to the procedure described for the synthesis of Example 1, starting from 5-iodouracil (0.10 g, 0.42 mmol). The crude was purified by column chromatography using SI (5 g) cartridge (cyclohexane:EtOAc 90:10) to afford the title compound (0.30 g, 19%) as white powder. $^1$H NMR (400 MHz, CDCl$_3$): δ 0.77-0.95 (m, 3H), 1.22-1.46 (m, 6H), 1.55-1.66 (m, 2H), 3.41 (dt, J=5.6, 7.1 Hz, 2H), 8.49 (s, 1H), 8.86 (s, 1H), 8.96 (t, J=5.6 Hz, 1H). $^{13}$C NMR (101 MHz, CDCl$_3$): δ 13.98, 22.50, 26.46, 29.08, 31.34, 41.42, 134.64, 143.41, 148.71, 150.97, 159.06. MS (ESI) m/z: 366 [M-H]⁻.

Example 9

N-hexyl-6-methoxy-2,4-dioxopyrimidine-1-carboxamide

5-Methoxyuracil (0.05 g, 0.33 mmol) was dissolved in dry DMSO (1.6 mL) and hexyl isocyanate (0.09 mL, 0.59 mmol) was added. The mixture was heated at 50° C. for 4 hrs. The reaction was poured into water (5 mL), the precipitate formed was filtered and washed with water and hexane. The crude was triturated with cyclohexane to afford the title compound (0.05 g, 56%) as white powder. $^1$H NMR (400 MHz, DMSO-$d_6$): δ 0.86 (t, J=6.9 Hz, 3H), 1.26-1.31 (m, 6H), 1.47-1.54 (m, 2H), 3.27 (td, J=7.0, 5.7 Hz, 2H), 3.66 (s, 3H), 7.71 (s, 1H), 9.22 (t, J=5.6 Hz, 1H), 11.94 (s, 1H). $^{13}$C NMR (101 MHz, DMSO-$d_6$): δ 13.86, 21.97, 25.87, 28.67, 30.83, 40.35, 56.49, 116.17, 136.52, 150.13, 150.24, 158.78. MS (ESI) m/z: 270 [M-H]$^4$, 287 [M-NH$_4$]$^+$, 308 [M-K]$^+$. MS (ESI) m/z: 268 [M-H]$^-$.

Example 10

5-(benzyl(methyl)amino)-N-hexyl-2,4-dioxo-pyrimidine-1-carboxamide

Step 1. Preparation of 5-[benzyl(methyl)amino]-1H-pyrimidine-2,4-dione

5-Bromouracil (0.15 g, 0.78 mmol) was dispersed in N-benzylmethylamine (2.0 mL, 15.70 mmol) and heated at 120° C. for 1 hr under microwave irradiation. The reaction mixture was diluted with water (1 mL) and concentrated. The white solid obtained was washed with water (10 mL), MeOH (5 mL) and then collected by dispersion in EtOAc (10 mL). The solvent was removed by evaporation to afford the title compound (0.22 g, 86%) as white powder. Analytical data were consistent with those reported in the literature (Tetrahedron 2005, 61(12), 3107-3113). $^1$H NMR (400 MHz, DMSO-$d_6$): δ 2.42 (s, 3H), 4.07 (s, 2H), 6.62 (s, 1H), 7.15-7.39 (m, 5H), 10.40 (br s, 1H), 11.07 (s, 1H). MS (ESI) m/z: 232 [M-H]$^+$.

Step 2. Preparation of 5-(benzyl(methyl)amino)-N-hexyl-2,4-dioxo-pyrimidine-1-carboxamide The title compound was obtained according to the procedure described for the synthesis of Example 1, starting from 5-[benzyl(methyl)amino]-1H-pyrimidine-2,4-dione (0.12 g, 0.52 mmol). The crude was purified by column chromatography using SI (5 g) cartridge (petroleum ether EtOAc 60:40) to afford the title compound (0.14 g, 76%) as white powder. $^1$H NMR (400 MHz, CDCl$_3$): δ 0.84 (t, J=6.8 Hz, 3H), 1.20-1.35 (m, 6H), 1.48-1.58 (m, 2H), 2.58 (s, 3H), 3.31 (dt, J=5.7, 7.0 Hz, 2H), 4.21 (s, 2H), 7.19-7.32 (m, 5H), 7.65 (s, 1H), 8.85 (s, 1H), 9.11 (t, J=5.7 Hz, 1H). $^{13}$C NMR (101 MHz, CDCl$_3$): δ 13.99, 22.50, 26.52, 29.19, 31.39, 38.99, 41.23, 57.44, 122.21, 127.46, 128.41, 128.36, 128.88, 137.04, 150.22, 150.42, 160.32. MS (ESI) m/z: 357 [M-H]$^-$.

Example 11

N-hexyl-5-methylamino-2,4-dioxo-pyrimidine-1-carboxamide 5-(Benzyl(methyl)amino)-N-hexyl-2,4-dioxo-pyrimidine-1-carboxamide(0.10 g, 0.28 mmol) was dissolved in EtOAc (30 mL) and hydrogenated in an H-Cube apparatus (using 10% Pd/C as catalyst, 1 bar hydrogen pressure, at 40° C.). The reaction mixture was concentrated under reduced pressure. The crude was purified by column chromatography using SI (2 g) cartridge (cyclohexane:EtOAc 85:15) to afford the title compound (0.02 g, 27%) as white powder. $^1$H NMR (400 MHz, DMSO-$d_6$): δ 0.78-0.99 (m, 3H), 1.17-1.36 (m, 6H), 1.50 (dd, J=14.0, 7.0 Hz, 2H), 2.57 (s, 3H), 3.27 (dd, J=5.7, 6.9 Hz, 2H), 5.01 (s, 1H), 7.05 (s, 1H), 9.32 (t, J=5.7 Hz, 1H), 11.87 (s, 1H). $^{13}$C NMR (101 MHz, CDCl$_3$): δ 13.85, 21.96, 25.89, 28.71, 29.70, 30.82, 40.21, 106.74, 126.49, 150.01, 150.68, 160.01. MS (ESI) m/z: 267 [M-H]$^-$.

Example 12

N-hexyl-5-morpholino-2,4-dioxo-pyrimidine-1-carboxamide

Step 1. Preparation of 5-morpholino-1H-pyrimidine-2,4-dione

The title compound was obtained according to the procedure described for the synthesis of Example 10 (Step1), starting from 5-bromouracil (0.10 g, 052 mmol) and 20 equivalents of morpholine. The crude was purified by precipitation in acidic water (10 mL, pH 5) to afford the title compound (0.08 g, 76%) as white, powder. $^1$H NMR (400 MHz, DMSO-$d_6$): δ 2.74-2.84 (m, 4H), 3.64 (t, J=4.6 Hz, 4H), 6.72 (s, 1H), 10.47 (s, 1H), 11.05 (s, 1H).

Step 2. Preparation of N-hexyl-5-morpholino-2,4-dioxo-pyrimidine-1-carboxamide The title compound was obtained according to the procedure described for the synthesis of Example 1, starting from 5-morpholino-1H-pyrimidine-2,4-dione (0.06 g, 0.32 mmol). The crude product was purified by preparative HPLC-MS to afford the title compound (0.04 g, 60%) as white powder. $^1$H NMR (400 MHz, CDCl$_3$): δ 0.77-0.95 (m, 3H), 1.26-1.43 (m, 6H), 1.51-1.66 (m, 2H), 2.90-3.07 (m, 4H), 3.36 (dt, J=5.7, 7.1 Hz, 2H), 3.73-3.94 (m, 4H), 7.83 (s, 1H), 8.32 (s, 1H), 9.10 (t, J=5.7 Hz, 1H). $^{13}$C NMR (101 MHz, CDCl$_3$): δ 13.98, 22.50, 26.50, 29.18, 31.37, 41.28, 50.32, 66.54, 122.44, 128.33, 150.06, 150.14, 159.59. MS (ESI) m/z: 323 [M-H]$^-$.

Example 13

N-hexyl-S-(4-methylpiperazin-1-yl)-2,4-dioxo-pyrimidine-1-carboxamide

Step 1. Preparation of 5-(4-methylpiperazin-1-yl)-1H-pyrimidine-2,4-dione

The title compound was obtained according to the procedure described for the synthesis of Example 10 (Step1), starting from 5-bromouracil (0.10 g, 0.52 mmol) and 20 equivalents of 1-methyl piperazine. The crude was purified by washing with water (10 dichloromethane (5 mL) and then collected by dispersion in EtOAc. (10 mL). The solvent was removed by evaporation to afford the title compound (0.15 g, 91%) as white powder. $^1$H NMR (400 MHz, DMSO-$d_6$): δ 2.18 (s, 3H), 2.34-2.42 (m, 4H), 2.74-2.84 (m, 4H), 6.72 (s, 1H). 10.41 (br s, 1H), 11.04 (br s, 1H).

Step 2. Preparation of N-hexyl-5-(4-methylpiperazin-1-yl)-2,4-dioxo-pyrimidine-1-carboxamide The title compound was obtained according to the procedure described for the synthesis of Example 1, starting from 5-(4-methylpiperazin-1-yl)-1H-pyrimidine-2,4-dione (0.15 g, 0.71 mmol). The crude was purified by column chromatography using SI (5 g) cartridge (petroleum ether:EtOAc 60:40) to afford the title compound (0.04 g, 17%) as white powder. $^1$H NMR (400 MHz, DMSO-$d_6$) δ 0.83-0.94 (m, 3H), 1.20-1.37 (m, 6H), 1.45-1.55 (m, 2H), 2.27 (br s, 3H), 2.94 (br s, 4H), 3.23-3.36 (m, 6H), 7.55 (s, 1H), 9.22 (t, J=5.6 Hz, 1H), 11.79 (br s, 1H). $^{13}$C NMR (101 MHz, DMSO-$d_6$): δ 14.35, 22.45, 26.35, 29.14, 31.31, 40.80, 45.88, 49.37, 54.65, 121.17, 128.26, 150.72, 150.86, 160.61. MS (ESI) m/z: 336 [M-H]$^-$.

Example 14

N-hexyl-2,4-dioxo-5-phenyl-pyrimidine-1-carboxamide

Step 1. Preparation of 1-benzhydryl-5-iodo-pyrimidine-2,4-dione

5-Iodouracil (0.10 g, 0.42 mmol) was suspended in dry MeCN (2.1 mL) and N,O-bis(trimethylsilyl)acetamide (0.25 mL, 1.05 mmol) was added under nitrogen atmosphere. When the reaction mixture turned clear, bromodiphenyl methane (0.15 g, 0.63 mmol) and a catalytic amount of $I_2$ were added and the reaction mixture was heated at 84° C. for 4 hrs. After cooling to room temperature, the mixture was concentrated under reduced pressure, diluted with EtOAc and washed with water. The aqueous phase was extracted with EtOAc (3×15 mL), the combined organic layers were washed with brine, dried over $Na_2SO_4$ and the solvent was removed under reduced pressure. The crude was purified by column chromatography using a Teledyne ISCO apparatus (cyclohexane:EtOAc 60:40) to afford the title compound (0.15 g, 87%) as white solid. $^1$H NMR (400 MHz, CDCl$_3$): δ 7.02 (s, 1H), 7.14-7.18 (m, 4H), 7.38-7.45 (m, 6H), 7.46 (s, 1H), 8.58 (s, 1H). MS (ESI) in/Z: 405 [M-H]$^+$.

Step 2. Preparation of 1-benzhydryl-5-phenyl-pyrimidine-2,4-dione

1-Benzhydryl-5-iodo-pyrimidine-2,4-dione (0.06 g, 0.15 mmol) was suspended in a 1:1 toluene/ethanol mixture (1,6 Phenylboronic acid (0.03 g, 0.22 mmol) was added followed by 2M aqueous solution of sodium carbonate (0.082 mL, 0.16 mmol). The resulting suspension was degassed under nitrogen atmosphere for 10 min, then tetrakis(triphenylphosphine) palladium(0) (0.017 g, 0.015 mmol) was added. The reaction was heated under microwave irradiation at 100° C. for 30 min. The reaction mixture was diluted with EtOAc and water was added. The two phases were separated and the aqueous layer was extracted with EtOAc (3×15 mL). The combined organic phases were dried over $Na_2SO_4$ and the solvent was removed under reduced pressure. The crude was purified by column chromatography using a Teledyne ISCO apparatus (cyclohexane:EtOAc 60:40) to afford the title compound (0.03 g, 62%) as pale yellow solid. $^1$H NMR (400 MHz, CDCl$_3$): δ 7.13 (s, 1H), 7.20-7.24 (m, 5H), 7.25 (s, 1H), 7.32-7.35 (m, 5H), 7.37-7.44 (m, 5H), 8.19 (br s, 1H). MS (ESI) to/z: 355 [M-H]$^+$.

Step 3. Preparation of 5-phenyl-1H-pyrimidine-2,4-dione

1-Benzhydryl-5-phenyl-pyrimidine-2,4-dione (0.13 g, 0.35 mmol) was added to solution of triflic acid (0.09 mL, 0.99 mmol) in TFA (0.87 mL) cooled to 0° C. The reaction mixture was stirred for 2 hrs and then quenched by addition of ice. The white precipitate was filtered and dried. The filtrate was diluted with EtOAc and the two phases were separated. The aqueous layer was further extracted with EtOAc (3×15 mL), the combined organic phases were dried over $Na_2SO_4$ and the solvent was removed under reduced pressure. The crude was taken up with a 1:1 dichloromethane/diethyl ether mixture; the product precipitated as white solid that was filtered and combined to the first fraction isolated (0.06 g, 65%). Analytical data were consistent with those reported in the literature (J. Org. Chem. 1990, 55, 1396-1399); $^1$H NMR (400 MHz, DMSO-$d_6$) δ 7.25-7.30 (m 1H), 7.32-7.39 (m, 2H), 7.51-7.56 (m 2H), 7.60 (s 1H), 11.10 (br s, 1H), 11.22 (br s, 1H). MS (ESI) m/z: 187 [M-H]$^-$.

Step 4. Preparation of N-hexyl-2,4-dioxo-5-phenyl-pyrimidine-1-carboxamide

The title compound was obtained according to the procedure described for the synthesis of Example 1, starting from 5-phenyluracil (0.05 g, 0.26 mmol); 1.8 equivalents of hexyl isocyanate were used herein. The crude was purified by silica gel column chromatography (cyclohexane:EtOAc 70:30) to afford the title compound (0.04 g, 44%) as white powder. $^1$H NMR (400 MHz, DMSO-$d_6$): δ 0.87 (t, J=6.5 Hz, 3H), 1.16-1.37 (m, 6H), 1.43-1.61 (m, 2H), 3.23-3.32 (m, 2H), 7.30-7.46 (m, 3H), 7.48-7.57 (m, 2H), 8.28 (s, 1H), 9.19 (t, J=5.6, 1H), 11.94 (s, 1H). $^{13}$C NMR (101 MHz, CDCl$_3$): δ 14.14, 22.67, 26.66, 29.31, 31.53, 41.50, 116.87, 128.53, 128.76, 131.49, 136.05, 149.92, 151.03, 161.31. MS (ESI) m/z: 333 [M-NH$_4$]$^+$. MS (ESI) m/z: 314 [M-H]$^-$.

Example 15

N-hexyl-6,6-dimethyl-2,4-dioxo-pyrimidine-1-carboxamide

Triphosgene (0.12 g, 0.71 mmol) was added to dry pyridine (2.0 mL) at 0° C. The mixture was stirred for 10 min, then a solution of 5,6-dimethyluracil (0.10 g, 0.71 mmol) in dry pyridine (3.0 mL) was added dropwise. The pale yellow suspension formed was stirred at room temperature for 5 hrs, then cooled to 0° C. before adding hexylamine (0.10 mL, 0.71 mmol). The reaction mixture was stirred at room temperature for 18 hrs. Water (30 mL) was added, and the product extracted with EtOAc (3×30 mL). The combined organic layer was dried over $Na_2SO_4$ and the solvent removed under reduced pressure. The crude was purified by column chromatography using a Teledyne ISCO apparatus (cyclohexane:EtOAc 90:10) to afford the title compound (0.02 g, 6%) as white powder. $^1$H NMR (400 MHz, CDCl$_3$) δ 0.90 (t, J=6.6 Hz, 3H), 1.25-1.38 (m, 6H), 1.53-1.67 (m, 2H), 1.83 (br s, 3H), 2.19 (br s, 3H), 3.30 (dt, J=5.6, 70 Hz, 2H), 7.42-7.65 (m, 1H), 9.68 (br s, 1H). $^{13}$C NMR (101 MHz, CDCl$_3$): δ 9.00, 13.34, 15.77, 22.35, 26.12, 28.91, 31.30, 40.70, 104.68, 146.24, 149.35, 162.15, 164.20. MS (ESI) m/z: 266 [M-H]$^-$.

Example 16

3-(cyclopropylmethyl)-N-hexyl-6-methyl-2,4-dioxo-pyrimidine-1-carboxamide

Step 1. Preparation of tert-butyl 3-(cyclopropylmethyl)-5-methyl-2,4-dioxo-pyrimidine-1-carboxylate Tert-butyl 5-methyl-2,4-dioxo-pyrimidine-1-carboxylate (0.10 g, 0.44 mmol) was dissolved in dry MeCN (2.2 mL)

and cesium carbonate was added (0.22 g, 0.66 mmol), followed by (bromomethyl)cyclopropane (0.13 mL, 1.33 mmol). The reaction mixture was stirred under nitrogen atmosphere at room temperature for 18 hrs. The reaction was then diluted with EtOAc and saturated aqueous NH$_4$Cl solution was added. The aqueous layer was extracted with EtOAc (3×15 mL), the combined organic phases were washed with brine, dried over Na$_2$SO$_4$ and the solvent was removed under reduced pressure. The crude was purified by column chromatography using a Teledyne ISCO apparatus (petroleum ether:EtOAc 80:20) to afford the title compound (0.09 g, 72%) as white solid. $^1$H NMR (400 MHz, CDCl$_3$) δ 0.38-0.43 (m, 2H), 0.43-0.50 (m, 2H), 1.21-1.32 (m, 1H), 1.61 (s, 9H), 1.97 (s, 3H), 3.84 (d, J=7.2 Hz, 2H), 7.64 (s, 1H). MS (ESI) m/z: 303 [M-Na]$^-$.

Step 2. Preparation of 3-(cyclopropylmethyl)-5-methyl-1H-pyrimidine-2,4-dione The title compound was obtained according to the procedure described in the literature (*Synthetic Comm.* 2001, 31, 3739-3746) starting from tert-butyl 3-(cyclopropylmethyl)-5-methyl-2,4-dioxo-pyrimidine-1-carboxylate (0.09 g, 0.32 mmol). The crude product (0.06 g) was obtained as white powder, and it was used in the next step without further purification. $^1$H NMR (400 MHz, CDCl$_3$): δ 0.37-0.43 (m, 2H), 0.44-0.52 (m, 2H), 1.15-1.37 (m, 1H), 1.94 (s, 3H), 3.83 (d, J=7.2 Hz, 2H), 6.92-7.11 (m, 1H), 9.94 (s, 1H). MS (ESI) m/z 179 [M-H]$^-$.

Step 3. Preparation of 3-(cyclopropylmethyl)-N-hexyl-5-methyl-2,4-dioxo-pyrimidine-1-carboxamide The title compound was obtained according to the procedure described for the synthesis of Example 1, starting from 3-(cyclopropylmethyl)-5-methyl-1H-pyrimidine-2,4-dione (0.05 g, 0.30 mmol); 1.8 equivalents of hexyl isocyanate were used herein. The crude product was purified by preparative HPLC-MS to afford the title compound (0.02 g, 23%) as colorless oil. $^1$H NMR (400 MHz, CDCl$_3$): δ 0.36-0.44 (m, 2H), 0.44-0.53 (m, 2H), 0.89 (t, J=6.7 Hz, 3H), 1.17-1.48 (m, 6H), 1.50-1.77 (m, 3H), 2.00 (d, J=1.3 Hz, 3H), 3.38 (td, J=7.1, 5.5 Hz, 2H), 3.86 (d, J=7.2 Hz, 2H), 8.23 (q, J=1.3 Hz, 1H), 9.37 (t, J=5.5 Hz, 1H). $^{13}$C NMR (101 MHz, CDCl$_3$): δ 4.02, 9.76, 13.47, 14.15, 22.66, 26.70, 29.35, 31.55, 41.34, 46.25, 111.81, 132.62, 150.77, 152.71, 163.16. MS (ESI) m/z: 308 [M-H]$^+$.

Example 17

5-[benzoyl(methyl)amino]-N-hexyl-2,4-dioxo-pyrimidine-1-carboxamide

N-hexyl-5-methylamino-2,4-dioxo-pyrimidine-1-carboxamide (0.08 g, 0.30 mmol) was dissolved in dry pyridine (4 mL). To the resulting solution, benzoyl chloride (0.04 mL, 0.39 mmol) was added. The reaction was stirred at room temperature under nitrogen atmosphere for 18 hrs, then concentrated under reduced pressure. The crude was purified by column chromatography using SI (5 g) cartridge (cyclohexane:EtOAc 84:16) to afford the title compound (0.05 g, 45%) as colorless oil. $^1$H NMR (400 MHz, CDCl$_3$): δ 0.89 (t, J=6.9 Hz, 3H), 1.28-1.33 (m, 6H), 1.53-1.59 (m, 2H), 3.29 (s, 3H), 3.34 (dt, J=5.7, 7.0 Hz, 2H), 7.33-7.43 (m, 5H), 8.22 (br s, 1H), 8.31 (br s, 1H) 8.88 (t, J=5.7 Hz, 1H). $^{13}$C NMR (101 MHz, CDCl$_3$): δ 13.96, 22.48, 26.44, 29.04, 31.31, 37.17, 41.41, 121.47, 127.17, 128.43, 130.27, 135.29, 137.63, 149.03, 150.05, 159.01, 171.78. MS (ESI) m/z: 371 [M-H]$^-$.

Example 18

5-(4-fluorophenyl)-N-hexyl-2,4-dioxo-pyrimidine-1-carboxamide

Step 1. Preparation of 1-benzhydryl-5-(4-fluorophenyl)pyrimidine-2,4-dione

The title compound was obtained according to the procedure described for the synthesis of Example 14 (Step 2), starting from 1-benzhydryl-5-iodo-pyrimidine-2,4-dione (0.30 g, 0.74 mmol). The crude was purified by column chromatography using a Teledyne ISCO apparatus (cyclohexane:EtOAc 70:30) to afford the title compound (0.17 g, 63%) as white powder. $^1$H NMR (400 MHz, DMSO-d$_6$) δ 6.98 (s, 1H), 7.12-7.21 (m, 2H), 7.26-7.30 (m, 4H), 7.31 (s, 1H), 7.35-7.46 (m, 8H), 11.69 (s, 1H). MS (ESI) m/z: 373 [M-H]$^+$ 371 [M-H]$^-$.

Step 2. Preparation of 5-(4-fluorophenyl)-1H-pyrimidine-2,4-dione

The title compound was obtained according to the procedure described for the synthesis of Example 14 (Step 3), starting from 1-benzhydiyl-5-(4-fluorophenyl)pyrimidine-2,4-dione (0.17 g, 0.47 mmol). The crude product (0.10 g) was obtained as white powder, and it was used in the next step without further purification. $^1$H NMR (400 MHz, DMSO-d$_6$) δ 7.14-7.21 (m, 2H), 7.55-7.61 (m, 2H), 7.62 (s, 1H), 11.13 (s, 1H), 11.24 (s, 1H).

Step 3. Preparation of 5-(4-fluorophenyl)-N-hexyl-2,4-dioxo-pyrimidine-1-carboxamide The title compound was obtained according to the procedure described for the synthesis of Example 6, starting from 5-(4-fluorophenyl)-1H-pyrimidine-2,4-dione (0.10 g, 0.48 mmol); 4.5 equivalents of hexyl isocyanate were used herein, splitted into two aliquots (2.2 equiv each) and the reaction mixture was heated under microwave irradiation to 110° C. for 1 hr (2 cycles of 30 min each). The crude was purified by column chromatography using a Teledyne ISCO apparatus (cyclohexane:EtOAc 84:16) to afford the title compound (0.03 g, 22% over two steps) as white powder. $^1$H NMR (400 MHz, CDCl$_3$) δ 0.91 (d, J=6.3 Hz, 3H), 1.27-1.42 (m, 6H), 1.58-1.68 (m, 2H), 3.41 (td, J=7.1, 5.6 Hz, 2H), 7.06-7.17 (m, 2H), 7.45-7.63 (m, 2H), 8.35 (s, 1H), 8.55 (s, 1H), 8.93-9.16 (m, 1H). $^{13}$C NMR (101 MHz, CDCl$_3$) δ 14.41, 22.33, 26.62, 29.26, 31.38, 41.46, 115.62, 126.97, 130.27, 135.83, 149.57, 150.60, 160.93, 162.81 (d, J=250.5 Hz). MS (ESI) m/z: 207 [M-H]$^+$.

Example 19

N-hexyl-5-(4-methoxyphenyl)-2,4-dioxo-pyrimidine-1-carboxamide

Step 1. Preparation of 1-benzhydryl-5-(4-methoxyphenyl)pyrimidine-2,4-dione The title compound was obtained according to the procedure described for the synthesis of Example 14 (Step 2), starting from 1-benzhydryl-5-iodo-pyrimidine-2,4-dione (0.30 g, 0.74 mmol). The crude was purified by column chromatography using a Teledyne ISCO apparatus (cyclohexane:EtOAc 60:40) to afford the title compound (0.14 g, 49%) as white powder. $^1$H NMR (400 MHz, DMSO-$d_6$) δ 3.72 (s, 3H), 6.85-6.91 (m, 2H), 6.97 (s, 1H), 7.20 (s, 1H), 7.23-7.29 (m, 5H), 7.35-7.40 (m, 2H), 7.40-7.47 (m, 3H), 11.62 (s, 1H). MS (ESI) m/z: 385 [M-H]$^+$.

Step 2. Preparation of
5-(4-methoxyphenyl)-1H-pyrimidine-2,4-dione

The title compound was obtained according to the procedure described for the synthesis of Example 14 (Step 3), starting from 1-benzhydryl-5-(4-methoxyphenyl)pyrimidine-2,4-dione (0.14 g, 0.36 mmol). The crude product (0.06 g) was obtained as white powder, and it was used in the next step without further purification. $^1$H NMR (400 MHz, DMSO-$d_6$) 3.75 (s, 3H), 6.86-6.95 (m, 2H) 7.43-7.49 (m, 2H), 7.51 (d) J=5.9 Hz, 1H), 11.01 (d, J=5.7 Hz, 1H), 11.17 (s, 1H). MS (ESI) m/z: 219 [M-H]$^+$.

Step 3. N-hexyl-5-(4-methoxyphenyl)-2,4-dioxo-pyrimidine-1-carboxamide

The title compound was obtained according to the procedure described for the synthesis of Example 6, starting from 5-(4-methoxyphenyl)-1H-pyrimidine-2,4-dione (0.06 g, 0.27 mmol); 5.4 equivalents of hexyl isocyanate were used herein, splitted into three aliquots (1.8 equiv each) and the reaction mixture was heated under microwave irradiation to 100° C. for 1 hr (3 cycles of 20 min each). The crude was purified by column chromatography using a Teledyne ISCO apparatus (cyclohexane:EtOAc 80:20) to afford the title compound (0.02 g, 17% over two steps) as white powder. $^1$H NMR (400 MHz, CDCl$_3$) δ 0.90 (d, J=6.8 Hz, 3H), 1.29-1.43 (m, 6H), 1.58-1.67 (m, 2H), 3.41 (td, J=7.1, 5.5 Hz, 2H), 3.83 (s, 3H), 6.89-7.00 (m, 2H), 7.41-7.57 (m, 2H), 8.46 (s, 1H), 8.51 (s, 1H), 9.11 (t, J=5.5 Hz, 1H). $^{13}$C NMR (101 MHz, CDCl$_3$) δ 14.63, 22.47, 26.85, 29.26, 31.63, 41.34, 55.37, 11414, 116.32, 123.66, 129.39, 134.34, 149.83, 150.71, 159.87, 161.58.

Example 20

N-hexyl-2,4-dioxo-5-(p-tolyl)pyrimidine-1-carboxamide

Step 1. Preparation of
1-benzhydryl-5-(p-tolyl)pyrimidine-2,4-dione

The title compound was obtained according to the procedure: described for the synthesis of Example 14 (Step 2), starting from 1-benzhydryl-5-iodo-pyrimidine-2,4-dione (0.11 g, 0.27 mmol) and p-tolylboronic acid (0.06 g, 0.41 mmol). The crude was purified by column chromatography using a Teledyne ISCO apparatus (cyclohexane:EtOAc 75:25) to afford the title compound (0.05 g, 50%) as a white solid. $^1$H NMR (400 MHz, CDCl$_3$) δ 2.32 (s, 3H), 7.11-7.15 (m, 3H), 7.20-7.24 (m, 6H), 7.34-7.44 (m, 6H), 8.16 (s, 1H). MS (ESI) m/z: 369 [M-H]$^-$.

Step 2. Preparation of
5-(p-tolyl)-1H-pyrimidine-2,4-dione

The title compound was obtained according to the procedure described for the synthesis of Example 14 (Step 3), starting from 1-benzhydryl-5-(p-tolyl)pyrimidine-2,4-dione (0.05 g, 0.13 mmol). The orange reaction mixture was here stirred for 1 hr at 0° C. and then quenched by addition of ice cold water (15 mL) and addition of dichloromethane (20 mL). Ice-cold diethyl ether (50 mL) was added, and the product precipitated. After storage at −20° C. for 15 hrs the title compound was obtained (white solid) by filtration and used without further purification in the following step. $^1$H NMR (400 MHz, DMSO-$d_6$): δ2.30 (s, 3H), 7.15 (d, J=7.9 Hz, 2H), 7.42 (d, J=8.1 Hz, 2H), 7.55 (d, J=5.9 Hz, 1H), 11.10 (d, J=6.5 Hz, 1H), 11.18 (s, 1H).

Step 3. Preparation of N-hexyl-2,4-dioxo-5-(p-tolyl) pyrimidine-1-carboxamide

The title compound was obtained according to the procedure described for the synthesis of Example 1, starting from 5-(p-tolyl)-9H-pyrimidine-2,4-dione (0.03 g, 0.13 mmol). The reaction was here stirred for 66 hrs, and the crude was purified by column chromatography using a Teledyne ISCO apparatus (cyclohexane:EtOAc 80:20) to afford the title compound (0.013 g, 30% over 2 steps) as a white solid, $^1$H NMR (400 MHz, DMSO-$d_6$): δ 0.87 (t, J=6.9 Hz, 3H), 1.23-1.35 (m, 6H), 1.48-1.55 (m, 2H), 2.32 (s, 3H), 3.25-3.34 (m, 2H), 7.22 (d, J=8.0 Hz, 1H), 7.42 (d, J=8.1 Hz, 1H), 8.25 (s, 1H), 9.19 (t, J=5.6 Hz, 1H), 11.90 (s, 1H). $^{13}$C NMR (101 MHz, CDCl$_3$): δ 14.14, 21.38, 22.67, 26.66, 29.32, 31.53, 4148, 116.85, 128.39, 128.54, 129.45, 135.54, 138.74, 149.99, 151.12, 161.48 MS (ESI) m/z: 328 [M-H]$^-$.

Example 21

N-hexyl-2,4-dioxo-5-[4-(trifluoromethyl)phenyl] pyrimidine-1-carboxamide

Step 1. Preparation of 1-benzhydryl-5-[4-(trifluoromethyl)phenyl]pyrimidine-2,4-dione The title compound was obtained according to the procedure described for the synthesis of Example 14 (Step 2), starting from 1-benzhydryl-5-iodo-pyrimidine-2,4-dione (0.33 g, 0.82 mmol) and 4-(trifluoromethyl)phenylboronic acid (0.23 g, 1.22 mmol). The crude was purified by column chromatography using a Teledyne ISCO apparatus (cyclohexane:EtOAc 70:30) to afford the title compound (0.15 g, 45%) as a white powder. $^1$H NMR (400 MHz, DMSO-$d_6$) δ 6.99 (s, 1H), 7.27-7.33 (m, 4H), 7.35-7.46 (m, 6H), 7.47 (s, 1H), 7.55-7.63 (m, 2H), 7.65-7.73 (m, 2H), 11.78 (s, 1H). MS (ESI) m/z: 371 [M-H]$^-$. MS (ESI) m/z: 373 [M-H]$^+$, 390 [M-NH$_4$]$^+$.

Step 2. Preparation of 5-[4-(trifluoromethyl)phenyl]-1H-pyrimidine-2,4-dione

The title compound was obtained according to the procedure described for the synthesis of Example 14 (Step 3), starting from 1-benzhydryl-5-(4-methoxyphenyl)pyrimidine-2,4-dione (0.15 g, 0.37 mmol). The crude product (0.09 g) was obtained as brown powder, and it was used in the next step without further purification. $^1$H NMR (400 MHz, DMSO-$d_6$) δ 7.67-7.74 (m, 2H), 7.77-7.84 (m, 3H), 11.30 (d, J=6.3 Hz, 1H), 11.33-11.37 (m, 1H). MS (ESI) m/z: 255 [M-H]$^-$. MS (ESI) m/z: 257 [M-H]$^+$.

Step 3. Preparation of N-hexyl-2,4-dioxo-5-[4-(trifluoromethyl)phenyl]pyrimidine-1-carboxamide The title compound was obtained according to the procedure described for the synthesis of Example 1, from the crude 5-[4-(trifluoromethyl)phenyl]-1H-pyrimidine-2,4-dione (0.09 g, 0.35 mmol). The crude was purified by column chromatography using a Teledyne ISCO apparatus (cyclohexane:EtOAc 70:30) to afford the title compound (0.03 g, 22% over two steps) as white powder. $^1$H NMR (400 MHz, CDCl$_3$) δ 0.90 (t, J=8.0 Hz, 3H), 1.26-1.45 (m, 6H), 1.53-1.75 (m, 2H), 3.42 (td, J=7.1, 5.6 Hz, 2H), 7.64-7.74 (m, 4H), 8.66 (s, 1H), 8.93 (s, 1H) 9.10 (t, J=5.2 Hz, 1H). $^{13}$C NMR (101 MHz, CDCl$_3$): 14.31, 22.47, 26.62, 29.16, 31.47, 41.38, 115.36, 124.22 (q, J=271.5 Hz), 125.55, 128.70, 130.50, 134.93, 149.73, 150.97, 161.01. MS (ESI) m/z: 382 [M-H]$^-$.

Example 22

N-Hexyl-5-(2-naphthyl)-2,4-dioxo-pyrimidine-1-carboxamide

Step 1. Preparation of 1-benzhydryl-5-(2-naphthyl)pyrimidine-2,4-dione

The title compound: was obtained according to the procedure described for the synthesis of Example 14 (Step 2), starting from 1-benzhydryl-5-iodo-pyrimidine-2,4-dione (0.11 g, 0.27 mmol) and 2-naphthylboronic acid (0.07 g, 0.41 mmol). The crude was purified by column chromatography using a Teledyne ISCO apparatus (cyclohexane:EtOAc 70:30) to afford the title compound (0.09 g, 80%) as an off-white solid. $^1$H NMR (400 MHz, CDCl$_3$): 7.17 (s, 1H), 7.24-7.27 (m, 2H), 7.36 (s, 1H), 7.38-7.47 (m, 10H), 7.76-7.88 (m, 5H), 8.28 for s, 1H). MS (ESI) m/z: 405 [M-H]$^+$.

Step 2. Preparation of 5-(2-naphthyl)-1H-pyrimidine-2,4-dione

The title compound was obtained according to the procedure described for the synthesis of Example 14 (Step 3), starting from 1-benzhydryl-5-(2-naphthyl)pyrimidine-2,4-dione (0.09 g, 0.21 mmol). The orange reaction mixture was here stirred for 1 hr at 0° C. and then quenched by addition of ice cold water (15 mL) and addition of dichloromethane (20 mL). Ice-cold diethyl ether (50 mL) was added, and the product precipitated. After storage at –20° C. for 15 hrs, the title compound was obtained by filtration (light-green solid, 0.033 g, 65%) and used without further purification in the following step. $^1$H NMR (400 MHz, DMSO-d$_6$): δ7.46-7.53 (m, 2H), 7.70 (dd, J=8, 6, 1.7 Hz, 1H), 7.77 (d, J=5.9 Hz, 1H), 7.86-7.90 (m, 3H), 8.12 (d, J=1.4 Hz, 1H), 11.21 (d, J=4.8 Hz, 1H), 11.29 (s, 1H) MS (ESI) m/z: 237.0 [M-H]$^-$.

Step 3. Preparation of N-hexyl-5-(2-naphthyl)-2,4-dioxo-pyrimidine-1-carboxamide The title compound was obtained according to the procedure described for the synthesis of Example 1, starting from 5-(2-naphthyl)-1H-pyrimidine-2,4-dione (0.03 g, 0.13 mmol). The reaction was here stirred for 66 hrs and the crude was purified by column chromatography using a Teledyne ISCO apparatus (cyclohexane:EtOAc 80:20) to afford the title compound (0.013 g, 28%) as a white solid. $^1$H NMR (400 MHz, DMSO-d$_6$): δ 0.88 (t, J=6.8 Hz, 3H), 1.21-1.36 (m, 6H), 1.49-1.59 (m, 2H), 3.27-3.34 (m, 2H), 7.51-7.56 (m, 2H), 7.67 (dd, J=8.6, 1.5 Hz, 1H), 7.90-7.98 (m, 3H), 8.13 (br s, 1H), 8.43 (s, 1H), 9.22 (t, J=5.2 Hz, 1H), 12.00 (s, 1H). $^{13}$C NMR (101 MHz, CDCl$_3$): δ 14.15, 22.67, 26.67, 29.32, 31.54, 41.53, 116.81, 125.90, 126.56, 126.75, 127.77, 127.90, 128.37, 128.46, 128.95, 133.29, 133.37, 136.27, 149.98, 151.10, 161.47. MS (ESI) m/z: 364 [M-H]$^-$.

Example 23

Methyl 5-bromo-3-(hexylcarbamoyl)-2,6-dioxo-pyrimidine-f-carboxylate

5-Bromo-N-hexyl-2,4-dioxo-pyrimidine-1-carboxamide (Example 5) (0.18 g, 0.58 mmol) was dissolved in dichloromethane (12 mL) and pyridine (0.10 mL, 1.24 mmol). Methyl chloroformate (0.05 mL, 0.66 mmol) was added at 0° C., and the reaction was stirred at room temperature for 5 hrs allowing slowly heating to room temperature. Another portion of methyl chloroformate (0.20 mL, 2.69 mmol) was added at 0° C. and the reaction was stirred at room temperature for additional 15 hrs. The solvent was removed under reduced pressure, and the crude was purified by column chromatography using a Teledyne ISCO apparatus (cyclohexane:EtOAc 75:25) to afford the title compound (0.016 g, 7.4%) as a clear, yellowish oil. $^1$H NMR (400 MHz, CDCl$_3$): δ 0.89 (t, J=7.2 Hz, 3H), 1.27-1.38 (m, 6H), 1.57-1.64 (m, 2H), 3.39 (td, J=7.1, 5.6, 2H), 4.08 (s, 3H), 8.74 (s, 1H), 8.76 (br s, 1H). $^{13}$C NMR (101 MHz, CDCl$_3$): δ 14.13, 22.64, 26.59, 29.17, 31.48, 41.78, 56.92, 98.71, 137.79, 148.46, 149.05, 149.40, 155.99. MS (ESI) m/z: 393 [M-NH$_4$]$^+$.

Example 24

Isobutyl 5-bromo-3-(hexylcarbamoyl)-2,6-dioxo-pyrimidine-1-carboxylate

5-Bromo-N-hexyl-2,4-dioxo-pyrimidine-1-carboxamide (Example 5) (0.06 g, 0.18 mmol) was dissolved in dry pyridine (1.5 mL), and isobutyl chloroformate (0.03 mL, 0.21 mmol) was added at 0° C. The reaction was stirred at room temperature for 15 hrs, and the solvent was removed under reduced pressure. The crude was purified by column chromatography using a Teledyne ISCO apparatus (cyclohexane:EtOAc 85:15) to afford the title compound (0.10 g, 48%) as a clear, colorless oil. $^1$H, NMR (400 MHz, CDCl$_3$): δ 0.89 (t, J=6.8 Hz, 3H), 1.01 (d, J=6.7 Hz, 6H), 1.28-1.38 (m, 6H), 1.57-1.64 (m, 2H), 2.11 (h, J=6.7 Hz, 1H), 3.39 (td, J=7.1, 5.7, 2H), 4.25 (d, J=6.6, 2H), 8.74 (s, 1H), 8.80 (t, J=4.6 Hz, 1H). $^{13}$C NMR (101 MHz, CDCl$_3$): δ 14.12, 18.90, 22.63, 26.58, 27.81, 29.18, 31.47, 41.76, 76.84, 98.78, 137.72, 148.46, 148.55, 149.44, 156.04. MS (ESI) m/z: 289 [M-CONH(CH$_2$)$_5$CH$_3$]$^-$.

Example 25

5-Bromo-N-hexyl-3-methyl-2,4-dioxo-pyrimidine-1-carboxamide

Step 1. Preparation of tert-butyl 5-bromo-3-methyl-2,4-dioxo-pyrimidine-1-carboxylate The title compound was obtained according to the procedure described for Example 16 (Step 1), starting from tert-butyl 5-bromo-2,4-dioxo-pyrimidine-1-carboxylate (1.43 g, 4.92 mmol); iodomethane was used herein and the reaction was stirred under nitrogen for 1.5 hrs. The crude was purified by column chromatography using a Teledyne ISCO apparatus (cyclohexane:EtOAc 70:30) to afford the title compound (0.85 g, 57%) as a white solid. $^1$H NMR (400 MHz, CDCl$_3$): δ 1.62 (s, 9H), 3.40 (s, 3H), 8.18 (s, 1H).

Step 2. Preparation of
5-bromo-3-methyl-1H-pyrimidine-2,4-dione

The title compound was obtained according to the procedure described in the literature (*Synthetic Comm.* 2001, 31, 3739-3746) starting from tert-butyl 5-bromo-3-methyl-2,4-dioxo-pyrimidine-1-carboxylate (0.85 g, 2.80 mmol). The crude (0.50 g) was obtained as a white, powder, and it was used in the next step without further purification. $^1$H NMR (400 MHz, CD$_3$OD): δ 3.32 (s, 3H), 7.78 (s, 1H). MS (ESI) m/z: 205 [M-H]$^+$.

Step 3. Preparation of 5-bromo-N-hexyl-3-methyl-2,4-dioxo-pyrimidine-1-carboxamide The title compound was obtained according to the procedure described for the synthesis of Example 1, starting from 5-bromo-3-methyl-1H-pyrimidine-2,4-dione (0.17 g, 0.81 mmol). The crude compound was purified by column chromatography using a Teledyne ISCO apparatus (cyclohexane:EtOAc 80:20) to afford the title compound (0.14 g, 51%) as a clear, colorless oil. $^1$H NMR (400 MHz, CDCl$_3$): δ 0.89 (t, J=6.6 Hz, 3H), 1.28-1.39 (m, 6H), 1.55-1.64 (m, 2H), 3.37-3.42 (m, 2H), 3.43 (s, 3H), 8.75 (s, 1H), 9.16-9.22 (m, 1H). $^{13}$C NMR (101 MHz, CDCl$_3$): δ 14.14, 22.65, 26.64, 29.25, 29.49, 31.51, 41.60, 99.09, 136.31, 149.40, 151.80, 158.55. MS (ESI) m/z: 203 [M-CONH(CH$_2$)$_5$CH$_3$]$^+$.

Example 26

Isobutyl 3-(hexylcarbamoyl)-2,6-dioxo-5-phenyl-pyrimidine-1-carboxylate

The title compound was obtained according to the procedure described for the synthesis of Example 24, starting from N-hexyl-2,4-dioxo-5-phenyl-pyrimidine-1-carboxamide (Example 14) (0.05 g, 0.17 mmol); 9.0 equivalents of isobutyl chloroformate were used herein. Another portion of isobutyl chloroformate (9.0 equivalents) was added after 5 hrs and the reaction stirred at room temperature for 15 hrs. The crude was purified by column chromatography using a Teledyne ISCO apparatus (cyclohexane:EtOAc 90:10) to afford the title compound (0.043 g, 39%) as a clear, colorless oil. $^1$H NMR (400 MHz, CDCl$_3$): δ 0.90 (t, J=6.8 Hz, 3H), 1.02 (d, J=6.8 Hz, 6H), 1.29-1.41 (m, 6H), 1.57-1.65 (m, 2H), 2.12 (h, J=6.7 Hz, 1H), 3.41 (td, J=7.1, 5.7 Hz, 2H), 4.27 (d, J=6.7 Hz, 2H), 7.36-7.45 (m, 3H), 7.53-7.57 (m, 3H), 8.57 (s, 1H), 8.96 (t, J=5.0 Hz, 1H). $^{13}$C NMR (101 MHz, CDCl$_3$): δ 14.14, 18.96, 22.65, 26.63, 27.84, 29.26, 31.52, 41.65, 76.42, 116.58, 128.58, 128.78, 128.92, 131.19, 135.34, 149.45, 149.54, 149.78, 159.35. MS (ESI) m/z: 416 [M-H]$^+$.

Example 27

N-hexyl-3-methyl-2,4-dioxo-6-phenyl-pyrimidine-1-carboxamide

Step 1. Preparation of 1-benzhydryl-3-methyl-5-phenyl-pyrimidine-2,4-dione

The title compound was obtained according to the procedure described for the synthesis of Example 16 (Step 1) starting from 1-benzhydryl-5-phenyl-pyrimidine-2,4-dione (prepared as in Example 14, Step 2) (0.37 g, 1.01 mmol); a 1:1 mixture of was dry MeCN/THF and iodomethane were used herein. The crude was purified by column chromatography using a Teledyne ISCO apparatus (cyclohexane: EtOAc 80:20) to afford the title compound (0.16 g, 43%) as a light-red solid. $^1$H NMR (400 MHz, CDCl$_3$): δ 3.46 (s, 3H), 7.19-7.24 (m, 6H), 7.28-7.43 (m, 11H). MS (ESI) m/z: 369 [m-H]$^+$.

Step 2. Preparation of N-hexyl-3-methyl-2,4-dioxo-5-phenyl-pyrimidine-1-carboxamide The title compound was obtained according to the procedure described for the synthesis of Example 14 (Step 3), starting from 1-benzhydryl-3-methyl-5-phenyl-pyrimidine-2,4-dione(0.160 g, 0.43 mmol). The orange reaction mixture was stirred for 1 hr under nitrogen at 0° C. and then quenched by addition of ice (approx. 20 mL). Dichloromethane (30 mL) was added and the two phases were separated. The aqueous layer was further extracted with dichloromethane (2×15 mL), and the combined organic phases were dried over Na$_2$SO$_4$. The solvent was removed under reduced pressure to give 3-methyl-5-phenyl-1H-pyrimidine-2,4-dione as a crude red/brown solid (MS (ESI) m/z: 203 [M-H]$^+$). The crude 3-methyl-5-phenyl-1H-4-pyrimidine-2,4-dione was used to prepare the title compound according to the procedure described, for the synthesis of Example 1. The crude was purified by column chromatography using a Teledyne ISCO apparatus (cyclohexane:EtOAc 90:10) to afford the title compound (0.059 g, 42%) as a yellow, sticky solid. $^1$H NMR (400 MHz, CDCl$_3$): δ 0.91 (t, J=6.7 Hz, 3H), 1.30-1.42 (m, 6H), 1.58-1.67 (m, 2H), 3.39-3.45 (m, 2H), 3.45 (s, 3H), 7.34-7.44 (m, 3H), 7.53-7.56 (m, 2H), 8.57 (s, 1H), 9.38 (s, 1H). $^{13}$C NMR (101 MHz, CDCl$_3$): δ 14.15, 22.67, 26.69, 28.55, 29.33, 31.55, 41.48, 116.18, 128.52, 128.63, 128.74, 132.46, 134.03, 150.43, 152.20, 161.52. MS (ESI) m/z: 330 [M-H]$^+$.

Example 28

N-Hexyl-5-(hydroxymethyl)-3-methyl-2,4-dioxo-pyrimidine-1-carboxamide

Step 1. Preparation of 5-[[tert-butyl(dimethyl)silyl]oxymethyl]-1H-pyrimidine-2,4-dione Imidazole (0.20 g, 3.0 mmol) and tert-butyldimethylsilyl chloride (0.72 g, 4.8 mmol) were added to a solution of 5-(hydroxymethyl)-9H-pyrimidine-2,4-dione (0.284 g, 2 mmol) in dichloromethane (5 mL) and MeCN (5 mL) at 0° C. The white slurry was stirred at room temperature for 48 hrs, quenched with saturated aqueous NH$_4$Cl (10 mL) and diluted with EtOAc (10 mL). The aqueous phase was extracted with EtOAc (3×15 mL), the combined organic layers were washed with brine (10 mL) and the solvent was removed under reduced pressure. The crude compound (white solid, 0.28 g, 54%) was used in the next step without further purification. $^1$H NMR (400 MHz, CD$_3$OD): δ 0.13 (s, 6H), 0.94 (s, 9H), 4.44 (s, 2H), 7.32 (t, J=1.2 Hz, 1H) MS (ESI) m/z: 257 [M-H]$^+$.

Step 2. Preparation of 5-[[tert-butyl(dimethyl)silyl]oxymethyl]-N-hexyl-2,4-dioxo-pyrimidine-1-carboxamide The title compound: was obtained according to the procedure described for the synthesis of Example 1, starting from 5-[[tert-butyl(dimethyl)silyl]oxymethyl]-1H-pyrimidine-2,4-dione (0.28 g, 1.08 mmol); 2.2 equiv of DMAP and 2.2 equiv of hexyl isocyanate were used herein. The reaction was here stirred for 66 hrs, and the crude was purified by column chromatography using a Teledyne ISCO apparatus (cyclohexane:EtOAc 75:25) to afford the title compound (0.30 g, 73%) as a white solid. $^1$H NMR (400 MHz, CDCl$_3$); δ 0.12 (s, 6H), 0.89 (t, J=6.9 Hz, 3H), 0.94 (s, 9H), 1.29-1.39 (m, 6H), 1.58-1.63 (m, 2H), 3.39 (td, J=7.1, 5.7 Hz, 2H), 4.52 (d, J=1.7 Hz, 2H), 828 (s, 1H), 8.47 (t, J=1.7 Hz, 1H), 9.06 (t, J=4.8 Hz, 1H). MS (ESI) m/z: 384 [M-H]$^+$.

Step 3. Preparation of 5-[[tert-butyl(dimethyl)silyl]oxymethyl]-N-hexyl-3-methyl-2,4-dioxo-pyrimidine-1-carboxamide The title compound was obtained according to the procedure described for the synthesis of Example 16 (Step 1), starting from 5-[[tert-butyl(dimethyl)silyl]oxymethyl]-N-hexyl-2,4-dioxo-pyrimidine-1-carboxamide (0.14 g, 0.37 mmol); iodomethane was used herein and the reaction was stirred under nitrogen at room temperature for 45 minutes. The crude was purified by column chromatography using a Teledyne ISCO apparatus (cyclohexane:EtOAc 90:10) to afford the title compound (0.055 g, 37%) as a clear, colorless oil. $^1$H NMR (400 MHz, CDCl$_3$): δ 0.12 (s, 6H), 0.90 (t, J=6.6 Hz, 3H), 0.95 (s, 9H), 1.29-1.41 (m, 6H), 1.57-1.65 (m, 2H), 3.36 (s, 3H), 3.40 (td, J=7.1, 5.7 Hz, 2H), 4.53 (d, J=1.7 Hz, 2H), 8.47 (t, J=1.6 Hz, 1H), 9.32 (t, J=4.5 Hz, 1H). MS (ESI) m/z: 398 [M-H]$^+$.

Step 4. Preparation of N-hexyl-5-(hydroxymethyl)-3-methyl-2,4-dioxo-pyrimidine-1-carboxamide 5-[[tert-Butyl(dimethyl)silyl]oxymethyl]-N-hexyl-3-methyl-2,4-dioxo-pyrimidine-1-carboxamide (0.05 g, 0.13 mmol) was treated with AcOH/THF/H$_2$O (3 mL, 4:1:1) at room temperature. The reaction was stirred for 22 hrs. Water (3 mL) was added, and the solution extracted with EtOAc/cyclohexane 1:1 (3×6 mL). The combined organic phases were concentrated to approx. 1 mL, which was then diluted with dichloromethane (1.5 mL) and injected onto a 4 g SiO$_2$ column followed by purification by column chromatography using a Teledyne ISCO apparatus (cyclohexane:EtOAc 70:30) to afford the title compound (0.033 g, 88%) as a white solid. $^1$H NMR (400 MHz, CDCl$_3$): δ 0.90 (t, J=6.8 Hz, 3H), 1.28-1.38 (m, 6H), 1.55-1.65 (m, 2H), 2.53 (bs, 1H), 3.38 (s, 3H), 3.39 (td, J=6.9, 5.8 Hz, 2H), 4.48 (s, 2H), 8.44 (bs, 1H), 9.26 (t, J=4.5 Hz, 1H). $^{13}$C NMR (101 MHz, CDCl$_3$): δ 14.15, 22.66, 26.67, 28.06, 29.30, 31.53, 41.47, 59.62, 114.39, 133.97, 150.22, 152.31, 162.77. MS (ESI) m/z: 284 [M-H]$^+$.

Example 29

Isobutyl 3-(hexylcarbamoyl)-5-(hydroxymethyl)-2,6-dioxo-pyrimidine-1-carboxylate

Step 1. Preparation of isobutyl 5-[[tert-butyl(dimethyl)silyl]oxymethyl]-3-(hexylcarbamoyl)-2,6-dioxo-pyrimidine-1-carboxylate The title compound was obtained according to the procedure described for the synthesis of Example 24, starting from 5-[[tert-butyl(dimethyl)silyl]oxymethyl]-N-hexyl-2,4-dioxo-pyrimidine-1-carboxamide (Example 28, Step 2) (0.30 g, 0.78 mmol). The crude was purified by column chromatography using a Teledyne ISCO apparatus (cyclohexane:EtOAc 90:10) to afford the title compound (0.17 g, 45%) as a white solid. $^1$H NMR (400 MHz, CDCl$_3$): δ 0.12 (s, 6H), 0.89 (t, J=6.7 Hz, 3H), 0.94 (s, 9H), 1.00 (d, J=6.9 Hz, 6H), 1.28-1.38 (m, 6H), 1.55-1.63 (m, 2H), 2.11 (h, J=6.7 Hz, 1H), 3.38 (td, J=7.2, 5.5 Hz, 2H), 4.24 (d, J=6.7 Hz, 2H), 4.52 (d, J=1.7 Hz, 2H), 8.47 (t, J=1.5 Hz, 1H), 8.91 (t, J=5.1 Hz, 1H). MS (ESI) m/z: 484 [M-H]$^+$.

Step 2. Preparation of isobutyl 3-(hexylcarbamoyl)-5-(hydroxymethyl)-2,6-dioxo-pyrimidine-1-carboxylate The title compound was obtained according to the procedure described for the synthesis of Example 28 (Step 4), starting from isobutyl 5-[[tert-butyl(dimethyl)silyl]oxymethyl]-3-(hexylcarbamoyl)-2,6-dioxo-pyrimidine-1-carboxylate (0.16 g, 0.34 mmol). The crude was purified by column chromatography using a Teledyne ISCO apparatus (cyclohexane:EtOAc 70:30) to afford the title compound (0.11 g, 89%) as a clear, colorless oil. $^1$H NMR (400 MHz, CDCl$_3$): δ 0.89 (t, J=6.5 Hz, 3H), 1.01 (d, J=6.7 Hz, 6H), 1.28-1.38 (m, 6H), 1.55-1.63 (m, 2H), 2.11 (h, J=6.7 Hz, 1H), 2.15 (t, J=6.3 Hz, 1H), 3.38 (td, J=7.1, 5.6 Hz, 2H), 4.25 (d, J=6.6 Hz, 2H), 4.49 (br s, 2H), 8.45 (t, J=1.1 Hz, 1H), 8.87 (t, J=5.6 Hz, 1H). $^{13}$C NMR (101 MHz, CDCl$_3$): δ 14.13, 18.92 (2C), 22.65, 26.61, 27.83, 29.23, 31.50, 41.62, 58.77, 76.48, 115.01, 135.52, 149.08, 149.37, 149.89, 160.30. MS (ESI) m/z: 370 [M-H]$^+$.

Example 30

Isobutyl 5-chloro-3-(hexylcarbamoyl)-2,6-dioxopyrimidine-1-carboxylate

The title compound was obtained according to the procedure described for the synthesis of Example 24, starting from 5-chloro-N-hexyl-2,4-dioxo-pyrimidine-1-carboxamide (Example 3) (0.119 g, 0.431 mmol); 2.4 equivalents of isobutyl chloroformate were used herein. The crude was purified by column chromatography using a Teledyne ISCO apparatus (cyclohexane:EtOAc 85:15) to afford the title compound (0.047 g, 29%) as a white solid. $^1$H NMR (400 MHz, CDCl$_3$): δ 0.89 (t, J=6.8 Hz, 3H), 1.01 (d, J=6.7 Hz, 6H), 1.28-1.38 (m, 6H), 1.57-1.64 (m, 2H), 2.11 (h, J=6.7 Hz, 1H), 3.39 (td, J=7.1, 5.5, 2H), 4.26 (d, J=6.6, 2H), 8.62 (s, 1H), 8.80 (t, J=4.9 Hz, 1H). $^{13}$C NMR (101 MHz, CDCl$_3$): δ 14.12, 18.89 (2C), 22.63, 26.58, 27.81, 29.19, 31.48, 41.77, 76.77, 111.14, 135.14, 148.40, 148.58, 149.20, 156.04. MS (ESI) m/z: 391 [M-NH$_4$]$^+$.

Example 31

N-hexyl-2,4-dioxo-5-(3-pyridyl)pyrimidine-1-carboxamide

Step 1. Preparation of 1-benzhydryl-5-(3-pyridyl)pyrimidine-2,4-dione

The title compound was obtained according to the procedure described for the synthesis of Example 14 (Step 2), starting from 1-benzhydryl-5-iodo-pyrimidine-2,4-dione (0.81 g, 2 mmol) and 3-pyridylboronic acid (0.370 g, 3 mmol). The crude was purified by column chromatography using a Teledyne ISCO apparatus (cyclohexane:EtOAc 30:70) to afford the title compound (0.17 g, 24%) as a white solid. $^1$H NMR (400 MHz, CDCl$_3$): δ 7.14 (s, 1H), 7.20-7.24

(m, 4H), 7.29-7.33 (m, 2H), 7.36-7.46 (m, 6H), 7.93 (dt, J=8.1, 2.0 Hz, 1H), 8.41 (d, J=1.7 Hz, 1H), 8.45 (s, 1H), 8.52 (dd, J=4.9, 1.6 Hz, 1H). MS (ESI) m/z: 356 [M-H]+.

Step 2. Preparation of 5-(3-pyridyl)-1H-pyrimidine-2,4-dione

The title compound was obtained according to the procedure described for the synthesis of Example 14 (Step 3), starting from 1-benzhydryl-5-(3-pyridyl)pyrimidine-2,4-dione (0.085 g, 0.239 mmol). Herein, anisole (0.163 g, 1.5 mmol) was added together with the triflic acid/TFA mixture, and the orange reaction mixture was here stirred for 1 hr at 0° C. TFA was removed by a stream of nitrogen and remaining TFA removed by co-evaporating with diethyl ether (40 mL). Water (15 mL) and acetonitrile (15 mL) was added, solidified in a dry ice-acetone bath, and the crude title compound was obtained by lyophilization. The crude was purified by column chromatography using a Teledyne ISCO apparatus (Dichloromethane:20% methanol in dichloromethane 30:70) to afford the title compound as, a triflic salt (0.067 g, 81%) as a white solid. $^1$H NMR (400 MHz, DMSO-$d_6$): δ 7.91 (dd, J=6.2, 5.8 Hz, 1H), 8.07 (d, J=6.1 Hz, 1H), 8.60 (dt, J=8.2, 1.6 Hz, 1H), 8.72 (dd, J=5.4, 1.4 Hz, 1H), 9.06 (d, J=2.1 Hz, 1H), 11.55 (s, 1H), 11.58 (d, =5.5 Hz, 1H). MS (ESI) m/z: 190 [M-H]+.

Step 3. Preparation of N-hexyl-2,4-dioxo-5-(3-pyridyl)pyrimidine-1-carboxamide

The title compound was obtained according, to the procedure described for the synthesis of Example 1, starting from 5-(3-pyridyl)-1H-pyrimidine-2,4-dione (0.067 g, 0,198 mmol). Herein, 2 equivalents of DMAP and 2.7 equivalents of hexyl isocyanate in 4 mL pyridine were used. The crude was purified by column chromatography using a Teledyne ISCO apparatus (cyclohexane:EtOAc 40:60) to afford the title compound (0.04 g, 57%) as a white solid. $^1$H NMR (400 MHz, CDCl$_3$): δ 0.90 (t, J=6.0 Hz, 3H), 1.29-1.41 (m, 6H), 1.58-1.67 (m, 2H), 3.42 (dt, J=7.1, 5.5 Hz, 2H), 7.37 (ddd, J=8.0, 4.9, 0.9 Hz, 1H), 7.97 (td, J=8.0, 2.0 Hz, 1H), 8.64 (dd, J=4.9, 1.7 Hz, 1H), 8.66 (s, 1H), 8.80 (dd, J=2.4, 0.9 Hz, 1H), 9.11 (t, J=5.0 Hz, 1H), 9.21 (s, 1H). $^{13}$C NMR (101 MHz, CDCl$_3$): δ 14.13, 22.66, 26.64, 29.29, 31.51, 41.58, 77.16, 113.74, 123.50, 127.93, 136.39, 136.58, 148.70, 149.48, 149.74, 151.09, 161.30. MS (ESI) m/z: 317 (M-Hr.

Example 32

N-octyl-2,4-dioxo-5-(trifluoromethyl)pyrimidine-1-carboxamide

The title compound was obtained according to the procedure described for the synthesis of Example 1, starting from 5-(trifluoromethyl) uracil (0.10 g, 0.55 mmol); 3.0 equivalents of octyl isocyanate were used herein. The crude was purified by column chromatography using a Teledyne ISCO apparatus (gradient from cyclohexane:EtOAc 70:30 to cyclohexane:EtOAc 60:40) and then washed with n-heptane to afford the title compound (0.04 g, 22%) as a white powder. $^1$H NMR (400 MHz, CDCl$_3$) δ 0.88 (d, J=6.8 Hz, 3H), 1.18-1.44 (m, 10H), 1.53-1.70 (m, 2H), 3.41 (td, J=7.1, 5.5 Hz, 2H), 8.90-8.97 (m, 3H). $^{13}$C NMR (101 MHz, CDCl$_3$) δ 14.20, 22.75, 26.92, 29.20, 29.26, 31.89, 41.80, 121.16 (q, J=268.7 Hz), 139.73, 148.25, 150.83, 156.86, MS (ESI) m/z 334 [M-H]+.

Example 33

N-hexyl-2,4-dioxo-5-(3-pyridyl)pyrimidine-1-carboxamide

Step 1. Preparation of 2-(5-phenylpentyl)isoindoline-1,3-dione

5-Phenylpentan-1-ol (0.50 g, 3 mmol), triphenylphosphine (0.45 g, 3 mmol), and phthalimide (0.80 g, 3 mmol) were vigorously stirred in dry THE (5 mL) while cooling to 0° C. A solution of DEAD (0.62 g, 3 mmol) in 5 mL of dry THF was added dropwise to the cooled mixture. After stirring at room temperature for 12 his, the solvent was removed by reduced pressure. The crude was purified by column chromatography using a Teledyne ISCO apparatus (cyclohexane:EtOAc 90:10) to afford the title compound (0.68 g, 76%) as a white solid. $^1$H NMR (400 MHz, DMSO-$d_6$): δ 1.22-1.34 (m, 2H), 1.49-1.69 (m, 4H), 2.52-2.58 (m, 2H), 3.56 (t, J=7.06 Hz, 2H), 7.06-7.27 (m, 5H), 7.75-7.95 (m, 4H). MS (ESI) m/z: 334 [M-H]−.

Step 2. Preparation of 5-phenylpentan-1-amine

Hydrazine monohydrate (0.36 g, 7.2 mmol) was added to a solution of 2-(5-phenylpentyl)isoindoline-1,3-dione (0.68 g, 2.3 mmol) in 25 mL of EtOH. The solution was stirred under reflux for 5 hrs and then cooled to room temperature. The white precipitate was removed by filtration and the filtrate was concentrated under reduced pressure. The residue was dissolved in a 1N solution of NaOH (80 mL) and extracted with chloroform (3×70 mL). The combined organic layers were washed with brine, dried over Na$_2$SO$_4$ and the solvent was removed under reduced pressure. The crude was purified by column chromatography using a Teledyne ISCO apparatus (solid deposition with TEA, eluent: 20% MeOH in dichloromethane with 1% of TEA) to afford the title compound (0.28 g, 73%) as a white solid. $^1$H NMR (400 MHz, CDCl$_3$): 1.37-1.48 (m, 2H), 1.58-1.72 (m, 4H), 2.57-2.69 (m, 2H), 3.29 (t, J=6.70 Hz, 2H), 7.13-7.24 (m, 3H), 7.26-7.34 (m, 2H).

Step 3. Preparation of 2,4-dioxo-N-(5-phenylpentyl)pyrimidine-1-carboxamide 5-phenylpentan-1-amine (0.07 g, 0.43 mmol) was dissolved in dry dichloromethane (4.5 mL). The solution was cooled to 0° C. and saturated aqueous NaHCO$_3$ solution (4.5 mL) was added. The biphasic mixture was stirred for 10 min at 0° C., the layers were allowed to separate then a solution of triphosgene (0.51 g, 0.52 mmol) in dry toluene (2.5 mL) was added to the organic layer. After 15 min the aqueous layer was extracted with dichloromethane (3×10 mL). The combined organic layers were dried over Na$_2$SO$_4$ and the solvent was removed under reduced pressure. The resulting residue was added to a solution of uracil (0.05 g, 0.43 mmol) and DMAP (0.01 g, 0.01 mmol) in dry pyridine (5 mL). The suspension was stirred at room temperature for 18 hrs. The crude was purified by column chromatography using a Teledyne ISCO apparatus (cyclohexane:EtOAc 75:25) to afford the title compound (0.04 g, 32%) as a white solid. $^1$H NMR (400 MHz, DMSO-$d_6$): 1.25-1.42 (m, 2H), 1.46-1.64 (m, 5H), 2.54-2.60 (m, 2H), 3.21-3.28 (m, 2H), 5.79 (d, J=8.38 Hz, 1H), 7.06-7.36 (m, 5H), 8.20 (d, J=8.40 Hz, 1H), 9.11 (t, J=5.65 Hz, 1H), 11.71 (s, 1H). $^{13}$C NMR (101 MHz, DMSO-d₆) δ 26.18, 28.56, 30.79, 35.12, 41.81, 40.26, 103.48, 125.78, 128.11, 129.30, 139.70, 149.23, 151.13, 161.80.

Example 34

N-[5-(4-fluorophenyl)pentyl]-2,4-dioxo-pyrimidine-1-carboxamide

Step 1. Preparation of 5-(4-fluorophenyl)pentan-1-ol

Under nitrogen atmosphere, at 0° C., to a stirring mixture of LiAlH₄ (0.27 g, 7.1 mmol) in dry Et₂O (6 mL), 5-(4'-fluorophenyl)valeric acid (0.35 g, 1.8 mmol) in dry Et₂O (5 mL) was added dropwise. The mixture was left to react at room temperature for 4 hrs, then at 0° C. H₂O (0.35 mL), 3M KOH solution (0.35 mL) and N₂O (1 mL) were very slowly added. The mixture was stirred for 1 hr at 0° C., filtered to remove the solid residue, and the organic phase dried over Na₂SO₄. The organic solution was again filtered and concentrated to dryness affording the title compound (0.32 g, 97%) as a colorless oil. $^1$H NMR (400 MHz, CDCl₃): δ 1.34-1.47 (m, 2H), 1.55-1.72 (m, 4H), 2.49-2.68 (m, 2H), 3.64 (t, J=6.56 Hz, 2H), 6.86-7.03 (m, 2H), 7.06-7.17 (m, 2H).

Step 2. Preparation of 2-[5-(4-fluorophenyl)pentyl]isoindoline-1,3-dione

The title compound was obtained according to the procedure described for the synthesis of Example 33 (Step1), starting from 5-(4-fluorophenyl)pentan-1-ol (0.32 g, 1.75 mmol). The crude was purified by column chromatography using a Teledyne ISCO apparatus (cyclohexane:EtOAc 90:10) to afford the title compound (0.37 g, 66%) as a white solid. $^1$H NMR (400 MHz, DMSO-d₆): δ 1.22-1.34 (m, 2H), 1.49-1.69 (m, 4H), 2.52-2.58 (m, 2H), 3.56 (t, J=7.06 Hz, 2H), 6.86-7.03 (m, 2H), 7.06-7.17 (m, 2H), 7.75-7.95 (m, 4H). MS (ESI) m/z: 312 [M-H]⁺.

Step 3. Preparation of 5-(4-fluorophenyl)pentan-1-amine

The title compound was obtained according to the procedure described for the synthesis of Example 33 (Step2), starting from 2-[5-(4-fluorophenyl)pentyl]isoindoline-1,3-dione (0.37 g, 1.18 mmol). The crude was purified by column chromatography using a Teledyne ISCO apparatus (solid deposition with TEA, eluent: 20% MeOH in dichloromethane with 1% of TEA) to afford the title compound (0.15 g, 70%) as a white solid. $^1$H NMR (400 MHz, DMSO-d₆): δ 1.22-1.34 (m, 2H), 1.37-1.46 (m, 2H), 1.46-1.59 (m, 2H), 2.52-2.64 (m, 4H), 7.01-7.12 (m, 2H), 7.16-7.27 (m, 2H). MS (ESI) m/z: 182 DA-Hr.

Step 4. Preparation of N-[5-(4-fluorophenyl)pentyl]-2,4-dioxo-pyrimidine-1-carboxamide The title compound was obtained according to the procedure described for the synthesis of Example 33 (Step3), starting from 5-(4-fluorophenyl)pentan-1-amine (0.07 g, 0.39 mmol). The crude was purified by column chromatography using a Teledyne ISCO apparatus (cyclohexane:EtOAc 75:25) to afford the title compound (0.015 g, 13%) as a white solid. $^1$H NMR (400 MHz, CDCl₃): δ 1.29-1.46 (m, 2H), 1.56-1.72 (m, 4H), 2.50-2.56 (m, 2H), 3.38 (td, J=5.54, 7.09 Hz, 2H), 5.89 (dd, J=1.71, 8.40 Hz, 1H), 6.89-7.02 (m, 2H), 7.06-7.17 (m, 2H), 8.41 (d, J=8.49 Hz, 1H), 8.48 (s, 1H), 9.04 (s, 1H). $^{13}$C NMR (101 MHz, CDCl₃) δ 26.28, 29.00, 31.05, 34.88, 41.11, 103.87, 114.90, 115.11, 129.59, 129.67, 138.86, 149.58, 151.29, 161.85.

Example 36

N-[(4-butylphenyl)methyl]-2,4-dioxo-pyrimidine-1-carboxamide

The title compound was obtained according to the procedure described for the synthesis of Example 33 (Step3), starting from (4-butylphenyl)methanamine (0.12 g, 0.66 mmol). The crude was purified by column chromatography using a Teledyne ISCO apparatus (cyclohexane:EtOAc 75:25) to afford the title compound (0,072 g, 36%) as a white solid. $^1$H NMR (400 MHz, CDCl₃): δ 0.92 (t, J=7.33 Hz, 3H), 1.24-1.43 (m, 2H), 1.50-1.69 (m, 2H), 2.52-2.66 (m, 2H), 4.54 (d, J=5.60 Hz, 2H), 5.89 (dd, J=1.85, 8.52 Hz, 1H), 7.14-7.25 (m, 4H), 8.43 (d, J=8.52 Hz, 1H), 8.69 (s, 1H), 9.33-9.46 (m, 1H). $^{13}$C NMR (101 MHz, CDCl₃) δ 13.91, 22.31, 33.58, 35.28, 44.93, 103.98, 127.63, 128.88, 134.01, 138.88, 142.69, 149.80, 151.29, 162.11. MS (ESI) m/z: 286 [M-H]⁺.

Example 36

N-[(4-propylcyclohexyl)methyl]-2,4-dioxo-pyrimidine-1-carboxamide

Step 1. Preparation of (4-propylcyclohexyl)methanol

The title compound was obtained according to the procedure described for the synthesis of Example 34 (Step1), starting from 4-trans-N-propylcyclohexanecarboxylic acid (0.50 g, 2.9 mmol). The crude product (0.45 g, 99%) was obtained as a colorless oil, and it was used in the next step without further purification. $^1$H NMR (400 MHz, DMSO-d₆): δ 0.80-0.88 (m, 7H), 1.10-1.18 (m, 3H), 1.23-1.33 (m, 3H), 1.64-1.79 (m, 4H), 3.18 (t, J=5.52 Hz, 2H), 4.30 (t, J=5.52 Hz, 1H).

Step 2. Preparation of 2[(4-propylcyclohexyl)methyl]isoindoline-1,3-dione

The title compound was obtained according to the procedure described for the synthesis of Example 33 (Step1), starting from (4-propylcyclohexyl)methanal (0.45 g, 2.88 mmol). The crude was purified by column chromatography using a Teledyne ISCO apparatus (cyclohexane:EtOAc 90:10) to afford the title compound (0.69 g, 83%) as a white solid. $^1$H NMR (400 MHz, DMSO-d₆): δ 0.80-0.88 (m, 7H), 1.10-1.18 (m, 3H), 1.23-1.33 (m, 3H), 1.64-1.79 (m, 4H), 3.46 (d, J=5.52 Hz, 2H), 7.75-7.95 (m, 4H). MS (ESI) m/z: 286 [M-H]⁺.

Step 3. Preparation of (4-propylcyclohexyl)methanamine

The title compound was obtained according to the procedure described for the synthesis of Example 33 (Step2), starting from 2-[(4-propylcyclohexyl)methyl]isoindoline-1,3-dione (0.69 g, 2.4 mmol). The crude was purified by column chromatography using a Teledyne ISCO apparatus (solid deposition with TEA, eluent: 20% MeOH in dichloromethane with 1% of TEA) to afford the title compound (0.15 g, 70%) as a white solid. $^1$H NMR (400 MHz, DMSO-d$_6$): δ 0.77-0.90 (m, 7H), 1.08-1.19 (m, 4H), 1.22-1.35 (m, 2H), 1.66-1.79 (m, 4H), 2.38 (d, J=6.45 Hz, 2H).

Step 4. Preparation of N-[(4-propylcyclohexyl)methyl]-2,4-dioxo-pyrimidine-1-carboxamide The title compound was obtained according to the procedure described for the synthesis of Example 33 (Step3), starting from (4-propylcyclohexyl)methanamine (0.07 g, 0.45 mmol). The crude was purified by column chromatography using a Teledyne ISCO apparatus (cyclohexane:EtOAc 75:25) to afford the title compound (0,005 g, 4%) as a white solid. $^1$H NMR (400 MHz, CDCl$_3$): 0.77-1.04 (m, 7H), 1.10-1.38 (m, 6H), 1.71-1.82 (m, 4H), 3.24 (dd, J=5.72, 6.75 Hz, 2H), 5.82-5.95 (m, 1H), 8.08 (s, 1H), 8.41 (d, J=8.49 Hz, 1H), 9.07 (s, 1H). $^{13}$C NMR (101 MHz, CDCl$_3$): δ 14.26, 20.06, 30.78, 32.52, 37.38, 38.00, 40.03, 47.45, 103.57, 138.93, 149.70, 151.32, 161.49. MS (ESI) m/z: 311 [M-NH$_4$]$^+$.

Example 37

3-but-3-enyl-N-hexyl-5-methyl-2,4-dioxo-pyrimidine-1-carboxamide

The title compound was obtained as a side product in the preparation of Example 16, and was isolated as colorless oil, $^1$H NMR (400 MHz, CDCl3) δ 0.90 (t, J=6.8 Hz, 3H), 1.27-1.39 (m, 6H), 1.59-1.65 (m, 2H), 1.99 (d, J=1.2 Hz, 3H), 2.37-2.43 (m, 2H) 3.35-3.40 (m, 2H), 4.00-4.06 (m, 2H), 5.03-5.10 (m, 2H), 5.81 (ddt, J=17.1, 10.2, 7.0 Hz, 1H), 8.22 (d, 1H), 9.33 (s, 1H). $^{13}$C NMR (101 MHz, CDCl3) δ 13.40, 14.14, 22.66, 26.70, 29.34, 31.55, 31.98, 41.02, 41.37, 77.16, 111.70, 117.40, 132.62, 134.62, 150.69, 152.46, 162.88. MS (ESI) m/z: 308 [M-H]$^+$.

Example 38

N-hexyl-5-(2-methylpyrazol-3-yl)-2,4-dioxo-pyrimidine-1-carboxamide

Step 1. Preparation of 1-benzhydryl-5-(2-methylpyrazol-3-yl)pyrimidine-2,4-dione The title compound was obtained according to the procedure described for the synthesis of Example 14 (Step 2), starting from 1-benzhydryl-5-iodo-pyrimidine-2,4-dione (0.20 g, 0.50 mmol). The crude was purified by column chromatography using a Teledyne ISCO apparatus (cyclohexane:EtOAc 30:70) to afford the title compound (0.12 g, 34%) as white powder. $^1$H NMR (400 MHz, DMSO) δ 3.57 (s, 3H), 6.11 (d, J=1, 9 Hz, 1H), 6.95 (s, 1H), 7.25-7.30 (m, 4H), 7.30 (s, 1H), 7.33 (d, J=1.9 Hz, 1H), 7.35-7.46 (m, 6H), 11.79 (s, 1H). MS (ESI) m/z: 359 [M-H]$^+$, 381 [M-Na]$^+$.

Step 2. Preparation of 5-(2-methylpyrazol-3-yl)-1H-pyrimidine-2,4-dione

The title compound was obtained according to the procedure described for the synthesis of Example 14 (Step 3), starting from 1-benzhydryl-5-(2-methylpyrazol-3-yl)pyrimidine-2,4-dione (0.12 g, 0.33 mmol). The crude product (0.09 g) was obtained as pale orange powder, and it was used in the next step without further Purification. $^1$H NMR (400 MHz, DMSO) δ 3.67 (s, 3H), 6.22 (d, J=1.8 Hz, 1H), 7.38 (d, J=18 Hz, 1H), 7.58 (d, J=6.0 Hz, 1H), 11.20-11.32 (m, 1H), 11.32-11.45 (m, 1H). MS (ESI) m/z: 193 [M-H]$^+$.

Step 3. Preparation of N-hexyl-5-(2-methylpyrazol-3-yl)-2,4-dioxo-pyrimidine-1-carboxamide The title compound was obtained according to the procedure described for the synthesis of Example 1, starting from 5-(2-methylpyrazol-3-yl)-1H-pyrimidine-2,4-dione (0.05 g, 0.26 mmol). The crude was purified by column chromatography using a Teledyne ISCO apparatus (cyclohexane:EtOAc 50:50) to afford the title compound (0.02 g, 17% over two steps) as white powder. $^1$H NMR (400 MHz, CDCl$_3$) δ 0.90 (t, J=7.0 Hz, 3H), 1.28-1.42 (m, 6H), 1.58-1.69 (m, 2H), 3.41 (td, J=7.1, 5.5 Hz, 2H), 3.84 (s, 3H), 6.32 (d, J=1.9 Hz, 1H), 7.51 (d, J=1.9 Hz, 1H), 8.51-8.59 (m, 2H), 8.77 (s, 1H), 9.04 (t, J=5.2 Hz, 1H). $^{13}$C NMR (101 MHz, CDCl$_3$) δ 14.35, 22.45, 27.02, 29.13, 31.73, 37.84, 41.54, 108.32, 133.24, 133.40, 138.50, 149.24, 150.76, 160.11. MS (ESI) m/z: 320 [M-H]$^+$. MS (ESI) m/z: 318 [M-H]$^-$.

Example 39

N-hexyl-5-(2-methoxyphenyl)-2,4-dioxo-pyrimidine-1-carboxamide

Step 1. Preparation of 1-benzhydryl-5-(2-methoxyphenyl)pyrimidine-2,4-dione

The title compound was obtained according to the procedure described for the synthesis of Example 14 (Step 2), starting from 1-benzhydryl-5-iodo-pyrimidine-2,4-dione (0.30 g, 0.50 mmol). The crude was purified by column chromatography using a Teledyne ISCO apparatus (from cyclohexane:EtOAc 60:40 to EtOAc 100%) to afford the title compound (0.17 g, 61%) as brown powder. $^1$H NMR (400 MHz, DMSO) δ 3.57 (s, 3H), 6.91 (td, J=7.5, 1.1 Hz, 1H), 6.97 (dd, J=8, 4, 1.1 Hz, 1H), 7.00 (s, 1H), 7.17-7.28 (m, 5H), 7.28-7.32 (m, 2H), 7.35-7.48 (m, 6H), 11.60 (s, 1H). MS (ESI) m/z: 385 [M-H]$^+$, 407 [M-Na]$^+$.

Step 2. Preparation of 5-(2-methoxyphenyl)-1H-pyrimidine-2,4-dione

The title compound was obtained according to the procedure described for the synthesis of Example 14 (Step 3), starting from 1-benzhydryl-5-(2-methoxyphenyl) pyrimidine-2,4-dione (0.17 g, 0.80 mmol). The crude product (0.06 g) was obtained as grey powder, and it was used in the next step without further purification. $^1$H NMR (400 MHz, DMSO) δ 3.72 (s, 3H), 6.90-6.96 (m, 1H), 7.02 (m, 1H), 7.18-7.22 (m, 1H), 7.27-7.32 (m, 1H), 7.37 (d, J=5.9 Hz, 1H), 10.88-10.94 (m, 1H), 11.11 (s, 1H). MS (ESI) m/z: 219 [M-H]$^+$, 236 [M-NH$_4$]$^+$.

Step 3. Preparation of N-hexyl-5-(2-methoxyphenyl)-2,4-dioxo-pyrimidine-1-carboxamide The title compound was obtained according to the procedure described for the synthesis of Example 1, starting from 5-(2-methoxyphenyl)-1H-pyrimidine-2,4-dione (0.06 g, 0.30 mmol). The crude was purified by column chromatography using a Teledyne ISCO apparatus (cyclohexane:EtOAc 80:20) to afford the title compound (0.015 g, 6% over two steps) as white powder. $^1$H NMR (400 MHz, CDCl$_3$) δ 0.86-0.99 (m, 3H), 1.28-1.43 (m, 6H), 1.57-1.68 (m, 2H), 3.40 (td, J=7.1, 5.5 Hz, 2H), 3.82 (s, 3H), 6.96 (dd, J=8.4, 1.0 Hz, 1H), 7.00 (td, J=7.5, 1.1 Hz, 1H), 7.28 (dd, J=7.5, 1.8 Hz, 1H), 7.37 (ddd, J=8.3, 7.5, 1.8 Hz, 1H), 8.23 (s, 1H), 8.49 (s, 1H), 9.11 (t, J=5.1 Hz, 1H). $^{13}$C NMR (101 MHz, CDCl$_3$) δ 14.26, 22.16, 26.66, 29.10, 31.46, 40.58, 55.36, 110.74, 120.31, 120.70, 130.15, 131.16, 137.16, 150.60, 150.68, 157.29, 160.90. MS (ESI) m/z: 346 [M-H]$^+$.

What is claimed is:

1. A compound of Formula Ib or pharmaceutically acceptable salt thereof

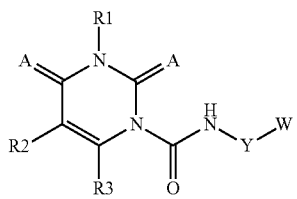

Formula Ib wherein

A represents O;

Y represents $C_1$-$C_8$ alkyl;

W represents hydrogen;

$R_1$ represents hydrogen;

$R_2$ represents trifluoromethyl, an optionally substituted heterocyclyl, an optionally substituted aryl, an optionally substituted heteroaryl, or a group selected from O—$R_6$ and $NR_7R_8$;

$R_3$ represents hydrogen;

$R_6$ represents an optionally substituted $C_1$-$C_8$ alkyl; and $R_7$ and $R_8$ independently represent hydrogen, an optionally substituted $C_1$-$C_6$ alkyl, a group (C=O) aryl, or, when taken together with the nitrogen atom to which they are bound, an optionally substituted heterocyclyl.

2. The compound of Formula Ib according to claim 1, wherein $R_2$ represents an optionally substituted heteroaryl selected from pyridine and pyrazole or an optionally substituted aryl selected from phenyl and naphthyl.

3. The compound of Formula Ib according to claim 1, wherein

A represents O;

$R_2$ represents trifluoromethyl, or a group selected from O—$R_6$ and $NR_7R_8$;

$R_7$ and $R_8$ independently represent: (a) hydrogen, (b) an optionally substituted C1-C6 alkyl, (c) a group (C=O) aryl or (d), when taken together with the nitrogen atom to which they are bound, an optionally substituted heterocyclyl selected from piperazine and morpholine.

4. The compound according to claim 1, wherein the compound of Formula Ib is selected from the group consisting of:

N-hexyl-2,4-dioxo-5-(trifluoromethyl)pyrimidine-1-carboxamide;

N-hexyl-5-morpholino-2,4-dioxo-pyrimidine-1-carboxamide;

5-[benzyl(methyl)amino]-N-hexyl-2,4-dioxo-pyrimidine-1-carboxamide;

N-hexyl-5-methylamino-2,4-dioxo-pyrimidine-1-carboxamide;

N-hexyl-5-(4-methylpiperazin-1-yl)-2,4-dioxo-pyrimidine-1-carboxamide;

N-hexyl-2,4-dioxo-5-phenyl-pyrimidine-1-carboxamide;

5-[benzoyl(methyl)amino]-N-hexyl-2,4-dioxo-pyrimidine-1-carboxamide;

N-hexyl-5-methoxy-2,4-dioxo-pyrimidine-1-carboxamide;

5-(4-fluorophenyl)-N-hexyl-2,4-dioxo-pyrimidine-1-carboxamide;

N-hexyl-5-(4-methoxyphenyl)-2,4-dioxo-pyrimidine-1-carboxamide;

N-hexyl-2,4-dioxo-5-(p-tolyl)pyrimidine-1-carboxamide;

N-hexyl-2,4-dioxo-5-[4-(trifluoromethyl) phenyl]pyrimidine-1-carboxamide;

N-hexyl-5-(2-naphthyl)-2,4-dioxo-pyrimidine-1-carboxamide;

N-hexyl-2,4-dioxo-5-(3-pyridyl)pyrimidine-1-carboxamide;

N-octyl-2,4-dioxo-5-(trifluoromethyl)pyrimidine-1-carboxamide;

N-hexyl-5-(2-methylpyrazol-3-yl)-2,4-dioxo-pyrimidine-1-carboxamide;

N-hexyl-5-(2-methoxyphenyl)-2,4-dioxo-pyrimidine-1-carboxamide; and.

5. A pharmaceutical composition comprising: an effective amount of a compound of Formula Ib according to claim 1, or a pharmaceutically salt thereof, and a pharmaceutically acceptable carrier.

* * * * *